(12) United States Patent
Sorge et al.

(10) Patent No.: US 7,678,541 B2
(45) Date of Patent: Mar. 16, 2010

(54) METHODS AND COMPOSITIONS FOR THE DETECTION OF A NUCLEIC ACID USING A NON-INVASIVE CLEAVAGE REACTION

(75) Inventors: Joseph A. Sorge, Wilson, WY (US); Scott Happe, Austin, TX (US); Andrew Firmin, Jackson, WY (US)

(73) Assignee: HoLogic, Inc., Marlborough, MA (US)

( * ) Notice: Subject to any disclaimer, the term of this patent is extended or adjusted under 35 U.S.C. 154(b) by 249 days.

(21) Appl. No.: 11/639,781

(22) Filed: Dec. 15, 2006

(65) Prior Publication Data

US 2008/0299549 A1 Dec. 4, 2008

Related U.S. Application Data

(60) Continuation-in-part of application No. 11/198,762, filed on Aug. 5, 2005, which is a continuation-in-part of application No. 10/981,942, filed on Nov. 5, 2004, which is a division of application No. 09/717,602, filed on Nov. 21, 2000, now Pat. No. 6,893,819.

(60) Provisional application No. 60/783,633, filed on Mar. 17, 2006, provisional application No. 60/794,628, filed on Apr. 24, 2006.

(51) Int. Cl.
*C12Q 1/68* (2006.01)
*C12P 19/34* (2006.01)
*C07H 21/04* (2006.01)

(52) U.S. Cl. .................. 435/6; 435/91.1; 435/91.2; 536/24.3

(58) Field of Classification Search ............ 435/6, 435/91.1, 91.2; 536/24.3
See application file for complete search history.

(56) References Cited

U.S. PATENT DOCUMENTS

| 5,654,143 | A | 8/1997 | Mallet et al. |
| 5,994,069 | A | 11/1999 | Hall et al. |
| 6,143,496 | A | * 11/2000 | Brown et al. ............ 435/6 |
| 6,458,535 | B1 | 10/2002 | Hall et al. |
| 6,759,226 | B1 | 7/2004 | Ma et al. |
| 2006/0110748 | A1 | 5/2006 | Sorge |
| 2008/0038734 | A1* | 2/2008 | Sorge et al. ............ 435/6 |

OTHER PUBLICATIONS

International Search Report and Written Opinion dated May 23, 2008 in corresponding PCT/US2007/087685, filed Dec. 15, 2007.
U.S. Appl. No. 11/442,525, filed May 25, 2006 Non-Final Office Action mailed Apr. 14, 2008.
Jeff G. Hall, et al., "Sensitive Detection Of DNA Polymorphisms By The Serial Invasive Signal Amplification Reaction," In: Proc. Natl. Acad. Sci. USA 97(15) Jul. 18, 2007, 8272-8277.

* cited by examiner

*Primary Examiner*—Kenneth R. Horlick
(74) *Attorney, Agent, or Firm*—Theodore Allen; Paul Nuzzi

(57) ABSTRACT

The invention provides methods, compositions and kits for generating a signal indicative of the presence of a target nucleic acid sequence in a sample comprising forming a cleavage structure by incubating a sample comprising a target nucleic acid sequence with upstream and downstream oligonucleotides, and cleaving the cleavage structure with a nuclease to generate a signal. The presence of a detectable signal is indicative of the presence of a target nucleic acid sequence and a non-invasive cleavage structure.

37 Claims, 19 Drawing Sheets

SEQUENCE LISTING

```
<160> NUMBER OF SEQ ID NOS: 23

<210> SEQ ID NO 1
<211> LENGTH: 43
<212> TYPE: DNA
<213> ORGANISM: Artificial Sequence
<220> FEATURE:
<223> OTHER INFORMATION: Synthetic sequence template

<400> SEQUENCE: 1
aaaataaata aaaaaaatac tgttgggaag ggcgatcggt gcg                       43

<210> SEQ ID NO 2
<211> LENGTH: 18
<212> TYPE: DNA
<213> ORGANISM: Artificial Sequence
<220> FEATURE:
<223> OTHER INFORMATION: Cleavage product of FEN cleavage of SEQ ID NO:1
      template

<400> SEQUENCE: 2
aaaataaata aaaaaaat                                                   18

<210> SEQ ID NO 3
<211> LENGTH: 23
<212> TYPE: DNA
<213> ORGANISM: Artificial Sequence
<220> FEATURE:
<223> OTHER INFORMATION: Synthetic primer that binds to M13
      bacteriophage
```

<400> SEQUENCE: 3
ccattcgcca ttcaggctgc gca                                          23

<210> SEQ ID NO 4
<211> LENGTH: 49
<212> TYPE: DNA
<213> ORGANISM: Artificial Sequence
<220> FEATURE:
<223> OTHER INFORMATION: Synthetic oligo for amplification of Pfu FEN

<400> SEQUENCE: 4
gacgacgaca agatgggtgt cccaattggt gagattatac caagaaaag              49

<210> SEQ ID NO 5
<211> LENGTH: 56
<212> TYPE: DNA
<213> ORGANISM: Artificial Sequence
<220> FEATURE:
<223> OTHER INFORMATION: Synthetic oligo for amplification of Pfu FEN

<400> SEQUENCE: 5
ggaacaagac ccgtttatct cttgaaccaa ctttcaaggg ttgattgttt tccact      56

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
tgtttcgacc tagcttgcca t                                            21

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
tgtttcgacc tagcttgcca gt                                           22

<210> SEQ ID NO 8
<211> LENGTH: 59
<212> TYPE: DNA
<213> ORGANISM: Artificial Sequence
<220> FEATURE:
<223> OTHER INFORMATION: Synthetic test template

<400> SEQUENCE: 8
acaaagctgg atcgaacggt caagcgtctt aaacaacgag cagtcagcag ccgccaaaa   59

<210> SEQ ID NO 9
<211> LENGTH: 47
<212> TYPE: DNA
<213> ORGANISM: Artificial Sequence
<220> FEATURE:
<223> OTHER INFORMATION: Synthetic probe

<400> SEQUENCE: 9
gagcgatgcg aaacggatcg agagtcgcag aatttgttgc tcgtcag                47

<210> SEQ ID NO 10

```
<211> LENGTH: 55
<212> TYPE: DNA
<213> ORGANISM: Artificial Sequence
<220> FEATURE:
<223> OTHER INFORMATION: Synthetic probe

<400> SEQUENCE: 10
ttgaaggtgt gcagtggaaa tagtaaccgg tactaattcc tctgcactcc ttcat         55

<210> SEQ ID NO 11
<211> LENGTH: 50
<212> TYPE: DNA
<213> ORGANISM: Artificial Sequence
<220> FEATURE:
<223> OTHER INFORMATION: Synthetic template

<400> SEQUENCE: 11
ctcgctacgc tttgcctagc tctggatgat taaggagacg tgaggaagta              50

<210> SEQ ID NO 12
<211> LENGTH: 24
<212> TYPE: DNA
<213> ORGANISM: Artificial Sequence
<220> FEATURE:
<223> OTHER INFORMATION: Synthetic probe

<400> SEQUENCE: 12
gagcgatgcg aaacggatcg agag                                          24

<210> SEQ ID NO 13
<211> LENGTH: 57
<212> TYPE: DNA
<213> ORGANISM: Artificial Sequence
<220> FEATURE:
<223> OTHER INFORMATION: Key probe

<400> SEQUENCE: 13
acctacaaca gaaccatcgc aaccctaaaa aagggtagcg atcgttctct tgtagga      57

<210> SEQ ID NO 14
<211> LENGTH: 55
<212> TYPE: DNA
<213> ORGANISM: Artificial Sequence
<220> FEATURE:
<223> OTHER INFORMATION: Probe

<400> SEQUENCE: 14
ccgacagaat tgatccgcac agaatggaat tcagcaatgg aaacacacga cgcct         55

<210> SEQ ID NO 15
<211> LENGTH: 63
<212> TYPE: DNA
<213> ORGANISM: Artificial Sequence
<220> FEATURE:
<223> OTHER INFORMATION: Synthetic target

<400> SEQUENCE: 15
gccgtaccgg gcagataagg taagtcgtta cctttgtgtg ctgcggaggc ggcgtcgtgc    60
gct                                                                 63

<210> SEQ ID NO 16
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 16
cggcatggcc cgtctattcc                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
cggcatggcc cgtctattca                                              20

<210> SEQ ID NO 18
<211> LENGTH: 14
<212> TYPE: DNA
<213> ORGANISM: Artificial Sequence
<220> FEATURE:
<223> OTHER INFORMATION: Reverse primer

<400> SEQUENCE: 18
cggcgtcgtg cgct                                                    14

<210> SEQ ID NO 19
<211> LENGTH: 54
<212> TYPE: DNA
<213> ORGANISM: Artificial Sequence
<220> FEATURE:
<223> OTHER INFORMATION: Synthetic probe

<400> SEQUENCE: 19
gccaagcgag agatgcgcgt cgtatttttt taccacgggc aactgtcggt tggg         54

<210> SEQ ID NO 20
<211> LENGTH: 28
<212> TYPE: DNA
<213> ORGANISM: Artificial Sequence
<220> FEATURE:
<223> OTHER INFORMATION: Synthetic primer

<400> SEQUENCE: 20
ccgacagaat tgatccgcac agaatgga                                     28

<210> SEQ ID NO 21
<211> LENGTH: 53
<212> TYPE: DNA
<213> ORGANISM: Artificial Sequence
<220> FEATURE:
<223> OTHER INFORMATION: Synthetic template

<400> SEQUENCE: 21
ggctgtctta actaggcgtg tcttaccaga tggtgcccga agacagccaa ccc          53

<210> SEQ ID NO 22
<211> LENGTH: 30
<212> TYPE: DNA
<213> ORGANISM: Artificial Sequence
<220> FEATURE:
<223> OTHER INFORMATION: Synthetic probe

<400> SEQUENCE: 22
gccaagcgag agatgcgcgt cgtatttttt                                   30

<210> SEQ ID NO 23

-continued

```
<211> LENGTH: 24
<212> TYPE: DNA
<213> ORGANISM: Artificial Sequence
<220> FEATURE:
<223> OTHER INFORMATION: Cleaved probe

<400> SEQUENCE: 23
taccacgggc aactgtcggt tggg                                            24
```

METHODS AND COMPOSITIONS FOR THE DETECTION OF A NUCLEIC ACID USING A NON-INVASIVE CLEAVAGE REACTION

RELATED APPLICATIONS

This application is a continuation-in-part which claims priority under 35 U.S.C. §120 to U.S. patent application Ser. No. 11/198,762 filed Aug. 5, 2005, now U.S. Pat. No. 7,309,573, which is a continuation-in-part of U.S. patent application Ser. No. 10/981,942 filed Nov. 5, 2004, now U.S. Pat. No. 7,276,597, which is a divisional of U.S. patent application Ser. No. 09/717,602 filed Nov. 21, 2000, now U.S. Pat. No. 6,893,819. This application also claims the benefit of U.S. Provisional Application No. 60/783,633, filed Mar. 17, 2006 and U.S. Provisional Application No. 60/794,628, filed on Apr. 24, 2006. The entire teachings of the above applications are incorporated herein by reference.

BACKGROUND OF THE INVENTION

The fidelity of DNA replication, recombination, and repair is essential for maintaining genome stability, and all of these processes depend on 5'→3' exonuclease enzymes which are present in all organisms. For DNA repair, these enzymes are required for damaged fragment excision and recombinational mismatch correction. For replication, these nucleases are critical for the efficient processing of Okazaki fragments during lagging strand DNA synthesis. In *Escherichia coli*, this latter activity is provided by DNA polymerase I (PolI); *E. coli* strains with inactivating mutations in the PolI 5'□3' exonuclease domain are not viable due to an inability to process Okazaki fragments. Eukaryotic DNA polymerases, however, lack an intrinsic 5'→3' exonuclease domain, and this critical activity is provided by the multifunctional, structure-specific metallonuclease FEN-1 (five' exonuclease-1 or flap endonuclease-1), which also acts as an endonuclease for 5' DNA flaps (Reviewed in Hosfield et al., 1998a, *Cell*, 95:135).

U.S. Pat. Nos. 5,843,669, 5,719,028, 5,837,450, 5,846,717 and 5,888,780 disclose a method of cleaving a target DNA molecule by incubating a 5' labeled target DNA with a DNA polymerase isolated from *Thermus aquaticus* (Taq polymerase) and a partially complementary oligonucleotide capable of hybridizing to sequences at the desired point of cleavage. The partially complementary oligonucleotide directs the Taq polymerase to the target DNA through formation of a substrate structure containing a duplex with a 3' extension opposite the desired site of cleavage wherein the non-complementary region of the oligonucleotide provides a 3' arm and the unannealed 5' region of the substrate molecule provides a 5' arm. The partially complementary oligonucleotide includes a 3' nucleotide extension capable of forming a short hairpin either when unhybridized or when hybridized to a target sequence at the desired point of cleavage. The release of labeled fragment is detected following cleavage by Taq polymerase.

U.S. Pat. Nos. 5,843,669, 5,719,028, 5,837,450, 5,846,717 and 5,888,780 disclose the generation of mutant, thermostable DNA polymerases that have very little or no detectable synthetic activity, and wild type thermostable nuclease activity. The mutant polymerases are said to be useful because they lack 5' to 3' synthetic activity; thus synthetic activity is an undesirable side reaction in combination with a DNA cleavage step in a detection assay.

U.S. Pat. Nos. 5,843,669, 5,719,028, 5,837,450, 5,846,717 and 5,888,780 disclose that wild type Taq polymerase or mutant Taq polymerases that lack synthetic activity can release a labeled fragment by cleaving a 5' end labeled hairpin structure formed by heat denaturation followed by cooling, in the presence of a primer that binds to the 3' arm of the hairpin structure. Further, U.S. Pat. Nos. 5,843,669, 5,719,028, 5,837,450, 5,846,717 and 5,888,780 teach that the mutant Taq polymerases lacking synthetic activity can also cleave this hairpin structure in the absence of a primer that binds to the 3' arm of the hairpin structure.

U.S. Pat. Nos. 5,843,669, 5,719,028, 5,837,450, 5,846,717 and 5,888,780 also disclose that cleavage of this hairpin structure in the presence of a primer that binds to the 3' arm of the hairpin structure by mutant Taq polymerases lacking synthetic activity yields a single species of labeled cleaved product, while wild type Taq polymerase produces multiple cleavage products and converts the hairpin structure to a double stranded form in the presence of dNTPs, due to the high level of synthetic activity of the wild type Taq enzyme.

U.S. Pat. Nos. 5,843,669, 5,719,028, 5,837,450, 5,846,717 and 5,888,780 also disclose that mutant Taq polymerases exhibiting reduced synthetic activity, but not wild type Taq polymerase, can release a single labeled fragment by cleaving a linear nucleic acid substrate comprising a 5' end labeled target nucleic acid and a complementary oligonucleotide wherein the complementary oligonucleotide hybridizes to a portion of the target nucleic acid such that 5' and 3' regions of the target nucleic acid are not annealed to the oligonucleotide and remain single stranded.

U.S. Pat. Nos. 5,846,717, 6,090,543, 6,001,567, 6,090,606, 5,985,557 and 5,994,069 relate to methods for forming a nucleic acid cleavage structure on a target sequence and cleaving the nucleic acid cleavage structure in a site specific manner. These patents also relate to using the 5' nuclease activity of a variety of enzymes to cleave the target-dependent cleavage structure, thereby indicating the presence of a specific nucleic acid sequence or variations thereof.

U.S. Pat. No. 5,843,669 discloses a method of detecting polymorphisms by cleavase fragment length polymorphism analysis using a thermostable FEN-1 nuclease in the presence or absence of a mutant Taq polymerase exhibiting reduced synthetic activity. According to this method, double stranded Hepatitis C virus (HCV) DNA fragments are labeled by using 5' end labeled primers (labeled with TMR fluorescent dye) in a PCR reaction. The TMR labeled PCR products are denatured by heating to 95° C. and cooled to 55° C. to generate a cleavage structure. U.S. Pat. No. 5,843,669 discloses that a cleavage structure comprises a region of a single stranded nucleic acid substrate containing secondary structure. Cleavage is carried out in the presence of CleavaseBN nuclease, FEN-1 nuclease derived from the archaebacteria *Methanococcus jannaschii* or both enzymes. Labeled reaction products are visualized by gel electrophoresis followed by fluoroimaging. U.S. Pat. No. 5,843,669 discloses that CleavaseBN nuclease and *Methanococcus jannaschii* FEN-1 nuclease produce cleavage patterns that are easily distinguished from each other, and that the cleavage patterns from a reaction containing both enzymes include elements of the patterns produced by cleavage with each individual enzyme but are not merely a composite of the cleavage patterns produced by each individual enzyme. This indicates that some of the fragments that are not cleaved by one enzyme (and which appear as a band in that enzyme's pattern) can be cleaved by a second enzyme in the same reaction mixture.

Lyamichev et al. disclose a method for detecting DNAs wherein overlapping pairs of oligonucleotide probes that are partially complementary to a region of target DNA are mixed with the target DNA to form a 5' flap region, and wherein cleavage of the labeled downstream probe by a thermostable FEN-1 nuclease produces a labeled cleavage product. Lyamichev et al. also disclose reaction conditions wherein multiple copies of the downstream oligonucleotide probe can be cleaved for a single target sequence in the absence of temperature cycling, so as to amplify the cleavage signal and allow quantitative detection of target DNA at sub-attomole levels (Lyamichev et al., 1999, *Nat. Biotechnol.*, 17:292).

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science*, 230:1350.

U.S. Pat. Nos. 5,210,015 and 5,487,972 disclose a PCR based assay for releasing labeled probe comprising generating a signal during the amplification step of a PCR reaction in the presence of a nucleic acid to be amplified, Taq polymerase that has 5' to 3' exonuclease activity and a 5', 3' or 5' and 3' end-labeled probe comprising a region complementary to the amplified region and an additional non-complementary 5' tail region. U.S. Pat. Nos. 5,210,015 and 5,487,972 disclose further that this PCR based assay can liberate the 5' labeled end of a hybridized probe when the Taq polymerase is positioned near the labeled probe by an upstream probe in a polymerization independent manner, e.g. in the absence of dNTPs.

U.S. Pat. Nos. 5,843,669, 5,719,028, 5,837,450, 5,846,717 and 5,888,780 also disclose a method of cleaving a labeled nucleic acid substrate at naturally occurring areas of secondary structure. According to this method, biotin labeled DNA substrates are prepared by PCR, mixed with wild type Taq polymerase or CleavaseBN (a mutant Taq polymerase with reduced synthetic activity and wild type 5' to 3' nuclease activity), incubated at 95° C. for 5 seconds to denature the substrate and then quickly cooled to 65° C. to allow the DNA to assume its unique secondary structure by allowing the formation of intra-strand hydrogen bonds between the complementary bases. The reaction mixture is incubated at 65° C. to allow cleavage to occur and biotinylated cleavage products are detected.

SUMMARY OF THE INVENTION

The invention provides methods, compositions and kits for generating a signal indicative of the presence of a target nucleic acid sequence in a sample comprising forming a cleavage structure by incubating a sample comprising a target nucleic acid sequence with upstream and downstream oligonucleotides, and cleaving the cleavage structure with a nuclease to generate a signal. The presence of a detectable signal is indicative of the presence of a target nucleic acid sequence and a non-invasive cleavage structure. The selective placement of a pair of interactive labels (e.g., fluorophore and a quencher) on the downstream oligonucleotide are selected to discriminate between an invasive and non-invasive cleavage reaction. Only non-invasive cleavage events are detectable.

The method may be performed as a single or sequential cleavage reaction. In a single cleavage reaction, a detectable signal indicative of the presence of a target nucleic acid is only produced if the cleavage reaction is non-invasive. In a sequential cleavage reaction a released flap from a first cleavage reaction serves as an upstream oligonucleotide in a second cleavage reaction. In a sequential cleavage reaction, the detectable signal is only produced when both the first and second cleavage reactions are non-invasive. In the event an invasive structure is formed, no signal is produced. The cleavage structure is invasive when the upstream oligonucleotide is complementary to the same region of the target/template nucleic acid as the downstream oligonucleotide.

In one aspect, the invention provides a method of detecting a target nucleic acid in a sequential detection reaction. In this aspect, a detectable signal is only produced when both the first and second cleavage reactions are non-invasive. In the event an invasive cleavage structure is formed, no signal is produced or detected. The method includes providing a target nucleic acid (FIG. 1; A'C'), a template nucleic acid (FIG. 1; H'F'), a first oligonucleotide (FIG. 1; A-1), a second oligonucleotide (FIG. 1; FC), a third oligonucleotide (FIG. 1; F2H), a cleavage agent and an agent with polymerization activity. The target and template nucleic acids have, in 3' to 5' order, a first region (A' or F'), and a second region (C' or H'). The first oligonucleotide is at least partially complementary to the first region of the target nucleic acid. The 3' region of the second oligonucleotide is at least partially complementary to the second region of the target nucleic acid and has a 5' region that is non-complementary to the target nucleic acid, but is at least partially complementary to the first region of the template nucleic acid. The 3' region of the third oligonucleotide is complementary to the second region of the template nucleic acid and has a 5' region that is non-complementary to the template nucleic acid. The third oligonucleotide is operatively coupled to a pair of interacting labels that produce a signal when they are separated upon a non-invasive cleavage of the third oligonucleotide (e.g., cleavage at the elbow of the third oligonucleotide). In the event an invasive cleavage structure is formed, no signal is produce as the third oligonucleotide is cleaved downstream of both labels (e.g., when the released flap is cleaved in an invasive cleavage reaction).

The reagents are mixed under reaction conditions that permit formation of a first and second duplex and first and second cleavage structure. The reaction conditions permit formation of a first duplex between the target nucleic acid and each of the first oligonucleotide and the second oligonucleotide (FIG. 1). In some embodiments, the 3' nucleotide of the first oligonucleotide is non-complementary to the target. The first and second oligonucleotides anneal to the target so that at least a nick separates the 3' end of the first oligonucleotide and the complementary portion of the second oligonucleotide. The second oligonucleotide forms a 5' non-complementary first flap when annealed to the target. This non-complimentary flap has a portion that is complementary, however, to a portion of the template nucleic acid. In some embodiments, the 3' terminal nucleotide of the released flap is non-complementary to the template. The second oligonucleotide is not detectably labeled.

The first cleavage structure is formed by the first oligonucleotide and the 5' non-complementary portion (first flap) of the second oligonucleotide when the oligonucleotides are annealed to the target. The first and second oligonucleotides anneal to the target so that at least a nick separates the target complementary portions of the first oligonucleotide and the second oligonucleotide. The cleavage structure may be cleaved at the elbow of the second oligonucleotide, thereby permitting release of the first flap (FIG. 1).

A second duplex is formed with the released first flap of the second oligonucleotide, the template nucleic acid, and the third oligonucleotide (FIG. 1). The third oligonucleotide has a 5' non-complementary second flap when annealed to the template nucleic acid. The released flap and third oligonucleotides anneal to the template so that at least a nick separates the template complementary portions of the released flap and the third oligonucleotide (FIG. 1).

The second cleavage structure is formed by the released flap and the 5' non-complementary portion (second flap) of the third oligonucleotide when the oligonucleotides are annealed to the template. The cleavage structure is cleaved at or upstream of the elbow of the third oligonucleotide by the nuclease, thereby generating a signal by the separation of a pair of interactive labels on the third oligonucleotide (FIG. 1). In the event an invasive cleavage reaction occurs in either the first or second cleavage reaction (e.g., cleavage created by overlapping complementary nucleotides), the pair of interactive labels will not separate and no signal is produced.

The placement of a pair of interactive labels (e.g., fluorophore and a quencher) on the third oligonucleotide can be selected to discriminate between an invasive and non-invasive cleavage reaction. In the event either the first or second cleavage reactions are invasive the pair of interactive labels are not separated and no detectable signal is produced. Accordingly, one embodiment of the invention contemplates the placement of a quencher (e.g., BHQ) at position +1 of the complementary region of the third oligonucleotide and a fluorophore (e.g., FAM) upstream of the elbow. In another embodiment, the position of the quencher and fluorophore are reversed. Thus, the fluorophore and quencher are only separated to produce a detectable signal when a non-invasive cleavage structure is formed in both the first and second cleavage reactions.

In the event the first cleavage reaction is invasive, the second oligonucleotide is cleaved downstream of the elbow downstream of both interactive labels. Therefore, the labels do not separate and no signal is produced.

In some embodiments, the reaction is performed in two distinct mixing steps. For example, a first reaction mixture is prepared by mixing the target nucleic acid, the first oligonucleotide, the second oligonucleotide, the cleavage agent and the polymerization agent under conditions that allow the first duplex to form and first cleavage reaction to occur. A second reaction mixture is then prepared by adding the third oligonucleotide and template nucleic acid to the first reaction mixture under reaction conditions which allow the formation of the second duplex and second cleavage reaction to occur.

The polymerization activity and cleavage means/agent may be present in a single enzyme. Such enzymes providing both activities include *E. coli* DNA polymerase I, T7 DNA polymerase, Tth DNA polymerase, or Taq DNA polymerase. In an alternative embodiment, the polymerization activity and cleavage means are each provided by a separate enzyme, e.g., a Pfu DNA polymerase and a FEN-1 nuclease. The polymerase activity is provided by a polymerase that may be a DNA polymerase and/or thermostable. The polymerase may lack a 5' to 3' exonuclease activity. The cleavage means can include a 5' nuclease activity. Such 5' nuclease activity is present in a FEN-1 nuclease. The FEN-1 nuclease may be a flap specific nuclease. In one embodiment, the FEN-1 nuclease is thermostable.

In yet another embodiment of any of the last three aspects of the invention, the series of reaction conditions are nucleic acid polymerization reaction conditions. In a further embodiment, the nucleic acid polymerization reaction conditions are polymerase chain reaction conditions.

In some embodiments of the invention, the 5' portion of the second and/or third oligonucleotide is at least partially complementary to the 3' portion of the second oligonucleotide. In yet a further embodiment, the 3' portion and the 5' portion of the second and/or third oligonucleotide form a stem structure when the second oligonucleotide is not hybridize to the target nucleic acid. The second and/or third oligonucleotide may include a linker sequence between the 5' portion and the 3' portion of the second oligonucleotide. The linker portion may not be complementary to the target nucleic acid but can be complementary to the first portion of the template nucleic acid. The 3' end of any of the first, second or third oligonucleotides or the template nucleic acid may be blocked.

In yet another aspect of the invention, the invention is directed to a composition including a target nucleic acid, a template nucleic acid, a first oligonucleotide, a second oligonucleotide and a third oligonucleotide. The target and template nucleic acids have, in 3' to 5' order, a first region and a second region. In some embodiments, the template and/or target further include an extension region between the first and second regions. The first oligonucleotide is at least partially complementary to the first region of the target nucleic acid and as a 3' terminal nucleotide which is non-complementary to the target. The second oligonucleotide's 3' region is at least partially complementary to the second region of the target nucleic acid and its 5' region is not complementary to the target nucleic acid but is at least partially complementary to the first region of the template nucleic acid. The third oligonucleotide's 3' region is at least partially complementary to the second region of the template nucleic acid, while its 5' region is not complementary to the template nucleic acid. The third oligonucleotide has a 5' region and a 3' region, the 3' region is at least partially complimentary to the second region of the template and the 5' region is non-complimentary to the template. A first member of a pair of interactive labels is operatively coupled to the 5' region and a second member of the pair of interactive labels is operatively coupled to the 3' region of the third oligonucleotide. In yet another aspect, the second member of the pair of interactive labels is operatively coupled to position +1 of the third oligonucleotide. In yet another embodiment, the composition includes a pair of primers.

In another aspect, the invention provides a method of detecting a target nucleic acid with a single cleavage reaction. In this aspect, a detectable signal is only produced when both the cleavage reaction is non-invasive. In the event an invasive cleavage structure is formed, no signal is produced. The method includes providing a target nucleic acid (FIG. 1; A'C'), a first oligonucleotide (FIG. 1; A-1), a second oligonucleotide (FIG. 1; FC but with a pair of interacting labels), a cleavage agent and optionally an agent with polymerization activity. The target nucleic acid has, in 3' to 5' order, a first region (A'), and a second region (C'). The first oligonucleotide is at least partially complementary to the first region of the target nucleic acid. The 3' region of the second oligonucleotide is at least partially complementary to the second region of the target nucleic acid and has a 5' region that is non-complementary to the target nucleic acid. The second oligonucleotide is operatively coupled to a pair of interacting labels that produce a signal when they are separated upon cleavage of the second oligonucleotide (e.g., cleavage at the elbow of the second oligonucleotide), but which do not produce a signal when the second oligonucleotide is cleaved downstream of both labels (e.g., is the first oligonucleotide overlaps the complementary portion of the second oligonucleotide).

The reagents are mixed under reaction conditions that permit formation of a first duplex and first cleavage structure.

The reaction conditions permit formation of a first duplex between the target nucleic acid and each of the first oligonucleotide and the second oligonucleotide (FIG. 1). In some embodiments, the 3' nucleotide of the first oligonucleotide is non-complementary to the target. The first and second oligonucleotides anneal to the target so that at least a nick separates the target complementary portion of the first oligonucleotide and the complementary portion of the second oligonucleotide. The second oligonucleotide forms a 5' non-complementary flap when annealed to the target.

The first cleavage structure is formed by the first oligonucleotide and the 5' non-complementary portion (first flap) of the second oligonucleotide when the oligonucleotides are annealed to the target. The first and second oligonucleotides anneal to the target so that at least a nick separates the target complementary portions of the first oligonucleotide and the second oligonucleotide. The cleavage structure is cleaved at or upstream of the elbow of the second oligonucleotide by the nuclease, thereby generating a signal by the separation of a pair of interactive labels on the second oligonucleotide. In the event an invasive cleavage reaction occurs (e.g., cleavage created by overlapping complementary nucleotides), the pair of interactive labels will not separate and no signal is produced.

In still another aspect, the invention is directed to a composition having a first oligonucleotide, a second oligonucleotide and a third oligonucleotide. The first oligonucleotide is at least partially complementary to a first region of a target nucleic acid and has a 3' terminal nucleotide which is non-complementary to the target. The second oligonucleotide has a 5' region and 3' region, the 3' region is at least partially complementary to a second region of the target and the 5' region is non-complementary to the target, but is at least partially complementary to the first region of a template nucleic acid. The third oligonucleotide has a 5' region and a 3' region, the 3' region is at least partially complimentary to the second region of the template and the 5' region is non-complimentary to the template. A first member of a pair of interactive labels is operatively coupled to the 5' region and a second member of the pair of interactive labels is operatively coupled to the 3' region. In yet another aspect, the second member of the pair of interactive labels is operatively coupled to position +1 of the third oligonucleotide. In yet another embodiment, the composition includes a pair of primers.

In still another aspect, the invention is directed to a composition having a first oligonucleotide, and a second oligonucleotide. The first oligonucleotide is at least partially complementary to a first region of a target nucleic acid and has a 3' terminal nucleotide which is non-complementary to the target. The second oligonucleotide has a 5' region and 3' region, the 3' region is at least partially complementary to a second region of the target and the 5' region is non-complementary to the target. A first member of a pair of interactive labels is operatively coupled to the 5' region and a second member of the pair of interactive labels is operatively coupled to the 3' region of the second oligonucleotide. In yet another aspect, the second member of the pair of interactive labels is operatively coupled to position +1 of the third oligonucleotide. In yet another embodiment, the composition includes a pair of primers.

In one embodiment, the compositions further include a cleavage means. In yet a further embodiment, the compositions also include a polymerase. The polymerase and cleavage means may be present in a single enzyme. Such enzymes providing both activities include E. coli DNA polymerase I, T7 DNA polymerase, Tth polymerase, or Taq DNA polymerase. In an alternative embodiment, the polymerization activity and cleavage means are each provided by a separate enzyme, e.g., a Pfu DNA polymerase and a FEN-1 nuclease. The polymerase activity is provided by a polymerase that may be a DNA polymerase and/or thermostable. The polymerase may lack a 5' to 3' exonuclease activity. The cleavage means can include a 5' nuclease activity. Such 5' nuclease activity is present in a FEN-1 nuclease. The FEN-1 nuclease may be a flap specific nuclease. The cleavage means may be a FEN-1 nuclease and the polymerase may be a Pfu DNA Polymerase.

In another embodiment of the compositions, the 3' end of the first, second or third oligonucleotide or template nucleic acid is blocked. The 3' blocking will prevent extension of the 3' end of the oligonucleotide by a polymerase.

The block may comprise a base that is non-complementary to the target nucleic acid or a modification that inhibits addition of a nucleotide triphosphate under conditions which permit nucleic acid synthesis or extension. Preferably, the blocked 3' end comprises:

a) a dideoxynucleotide;
b) a nucleotide wherein the 3' hydroxyl has been replaced with a phosphate group; or
c) a nucleotide with a reporter moiety attached to the 3' carbon or to the 3' oxygen.

In yet another embodiment, the 5' portion of the second oligonucleotide is at least partially complementary to the 3' portion of the second oligonucleotide. In yet another embodiment, the 5' portion of the third oligonucleotide is at least partially complementary to the 3' portion of the third oligonucleotide. In a further embodiment, the 3' portion and the 5' portion of the second and/or third oligonucleotide form a stem structure when the second and/or third oligonucleotide is not hybridize to the target or template nucleic acid. The second and/or third oligonucleotide may include a linker sequence between the 5' portion and the 3' portion of the second oligonucleotide. In some embodiments, the linker sequence is not complementary to the target nucleic acid but is complementary to the first portion of the template nucleic acid.

A kit may comprise any one of the compositions as described hereinabove, and packaging materials therefore.

Further features and advantages of the invention will become more fully apparent in the following description of the embodiments and drawings thereof, and from the claims.

DESCRIPTION

Figure 1A:
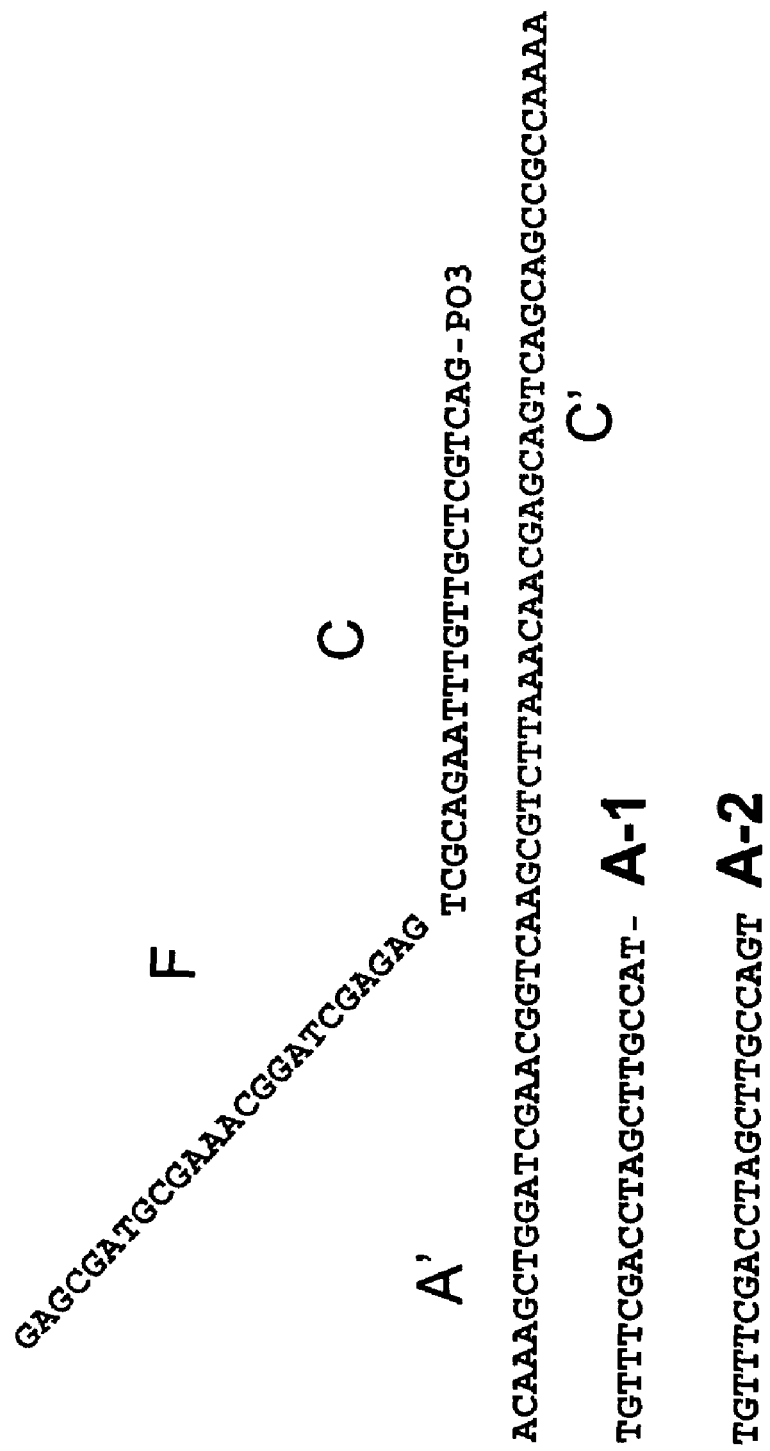
FIG. 1 demonstrates FEN nuclease cleavage structures.

The invention provides a method wherein, a target nucleic acid is detected by forming and cleaving a cleavage structure comprising a target nucleic acid, and an upstream and downstream oligonucleotide. The method may be performed sequentially with two or more cleavage reactions. In a sequential cleavage reaction a first cleavage structure comprising a target nucleic acid, a first oligonucleotide and a second oligonucleotide is formed. The first cleavage structure is formed when the first and second oligonucleotides hybridize to the target nucleic acid. A 5' flap of the second oligonucleotide is cleaved and released. The released flap serves as an upstream oligonucleotide in a second cleavage structure. The second cleavage structure comprises a template nucleic acid, the released flap of the second oligonucleotide and a third oligonucleotide. The second cleavage structure is formed when the released flap and third oligonucleotide hybridize to the template nucleic acid. If both the first and second cleavage events are non-invasive the third oligonucleotide is cleaved between a pair of interactive labels. Cleavage between the pair of interactive labels produces a detectable signal. The presence and/or amount of the target nucleic acid is determined by detecting the signal generated. In the event either the first or second cleavage events are invasive no signal is produced.

As used herein, a "target nucleic acid" refers to a polynucleotide which comprises in 3' to 5' order a first region that is complementary to at least a portion of a first oligonucleotide and a second region that is complementary to at least a portion of a second oligonucleotide. In some embodiments, the target may have an extension region between the first and second regions of the target. The target nucleic acid may comprise single or double-stranded DNA or RNA.

As used herein, a "first region" as it refers to a target nucleic acid, means a length of nucleotides sufficient to permit hybridization of a first oligonucleotide wherein the "first region" is complementary to at least a portion of a first oligonucleotide, defined herein. A "first region" is in the range of about 6 nucleotides to about 1000 nucleotides in length, with a preferred range of about 8 to 30 nucleotides, and optimally, a range of 10 to 25 nucleotides.

As used herein, a "first region" as it refers to a template nucleic acid, described herein below, means a length of nucleotides sufficient to permit hybridization of a released flap of a second oligonucleotide wherein the "first region" is complementary to at least a portion of a released flap of the second oligonucleotide, defined herein. A "first region" is in the range of about 6 nucleotides to about 1000 nucleotides in length, with a preferred range of about 8 to 30 nucleotides, and optimally, a range of 10 to 25 nucleotides.

As used herein, "extension region" refers to a length of nucleotides sufficient to permit extension of an oligonucleotide (e.g., forward primer or the released flap of a second oligonucleotide) via a nucleic acid polymerization activity. An "extension region" is present in some embodiments of the target and template nucleic acids. When present the "extension region" is between the first and second regions of the target or template nucleic acid. The "extension region" is about 1 nucleotide to about 1000 nucleotides in length, with a preferred range of about 1-100 nucleotides, a more preferred range of 3 to 50, and optimally, a range of 3-10 nucleotides in length.

As used herein, a "second region" as it refers to a target nucleic acid, means a length of nucleotides that is sufficient to permit hybridization of a second oligonucleotide, wherein the "second region" is complementary to at least a portion of a second oligonucleotide, defined herein. A "second region" is in the range of about 6 nucleotides to about 1000 nucleotides in length, with a preferred range of about 8 to 30 nucleotides, and optimally, a range of 10 to 25 nucleotides.

As used herein, a "second region" as it refers to a template nucleic acid, described herein below, means a length of nucleotides that is sufficient to permit hybridization of a third oligonucleotide, wherein the "second region" is complementary to at least a portion of a third oligonucleotide, defined herein. A "second region" is in the range of about 6 nucleotides to about 1000 nucleotides in length, with a preferred range of about 8 to 30 nucleotides, and optimally, a range of 10 to 25 nucleotides.

As used herein, "at least a portion of", as it refers to a first, second, third or fourth oligonucleotide, means less than 100%, (e.g., 99%, 90%, 75%, 50%, 25% etc. . . . ) of the nucleotides of the first, second, third or fourth oligonucleotide.

As used herein, a "template nucleic acid" refers to a polynucleotide which comprises in 3' to 5' order a first region that is complementary to at least a portion of the released flap of the second oligonucleotide and a second region that is complementary to at least a portion of a third oligonucleotide. A template nucleic acid may also include an "extension region" between the first and second regions of the template. The template nucleic acid may comprise single or double-stranded DNA or RNA or chemical modifications or unnatural variants of such.

As used herein, "oligonucleotide" refers to a nucleic acid comprising a region that is complementary to a target nucleic acid sequence and/or a template nucleic acid sequence.

As used herein, the term "oligonucleotide" also refers to primers, probes, upstream oligonucleotides (e.g., first oligonucleotide and first released flap), downstream oligonucleotide (e.g., second oligonucleotide and third oligonucleotide) and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). The term "oligonucleotide" includes double- and single-strand DNA, as well as double- and single-strand RNA. The term "oligonucleotide" intends a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature. Where the oligonucleotide is used as a primer for the polymerizing activity to polymerize nucleotides from its 3' end complementary to the extension region, the oligonucleotide also may be referred to as a primer. An "oligonucleotide" according to the invention also refers to peptide nucleic acids (PNA) or hybrids of nucleic acids and peptide nucleic acids.

Oligonucleotides useful in the invention are generally in the range of about 8 nucleotides to about 200 nucleotides in length.

A "first oligonucleotide" according to the invention is preferably 6 to 100, more preferably 8 to 30 and most preferably 20 nucleotides in length. A "first" oligonucleotide is at least partially complementary to the target nucleic acid. The first oligonucleotide may have a 3' end which is non-complementary to the target nucleic acid.

A "second oligonucleotide" according to the invention is preferably 20-120, more preferably 25-45 and most preferably 35 nucleotides in length. A "second oligonucleotide" comprises a 3' and a 5' region. The 3' region of a "second oligonucleotide" is at least partially complementary to the target nucleic acid and is preferably 8-80 and most preferably 10-20 nucleotides. A 5' region of a "second oligonucleotide" is preferably 0 to 80 and most preferably 10 to 20 nucleotides in length for embodiments wherein a duplex structure comprises a preformed flap. In another embodiment of the invention, the 5' region of the second oligonucleotide according to the invention is not complementary to a target nucleic acid.

A "third oligonucleotide" according to the invention is preferably 20-120, more preferably 25-45 and most preferably 35 nucleotides in length. A "third oligonucleotide" comprise a 3' and a 5' region. Third oligonucleotides according to the invention comprise a 3' region that is at least partially complementary to a region of a template nucleic acid and is preferably 8 to 80 and most preferably 10-20 nucleotides. A 5' region of a "third oligonucleotide" is preferably 0 to 80, most preferably 10 to 20 nucleotides in length for embodiments wherein a duplex structure comprises a preformed flap. In another embodiment of the invention, the 5' region of the "third oligonucleotide" according to the invention is not complementary to a template nucleic acid.

In one embodiment, the invention utilizes a cleavage resistant oligonucleotide. In a preferred embodiment, the second and/or third oligonucleotide is a cleavage resistant probe.

As used herein, "cleavage resistant probe" or "cleavage resistant oligonucleotide" according to the invention is a probe that forms a cleavage structure that is susceptible to cleavage by a cleavage agent upon formation of a non-overlapping (non-invasive) cleavage structure, but which cannot be cleaved by a cleavage agent upon formation of an overlapping (invasive) cleavage structure. This resistance to cleavage is accomplished by including one or more modifications that renders the portion of the probe targeted by an overlapping structure resistant to cleavage. Thus, the cleavage resistant probe has at least a portion which is resistant to cleavage by a cleavage agent of the invention.

In one embodiment, the cleavage resistant probe comprises one or more modifications downstream of the +1 and/or +2 position that renders the probe resistant to cleavage by a cleavage agent of the invention. These modifications render the probe resistant to cleavage in a region targeted for cleavage by an overlapping (invasive) cleavage structure. However, the cleavage resistant probe is susceptible to cleavage in a region targeted for cleavage by a non-overlapping (non-invasive) cleavage structure. Suitable modifications include, but are not limited to, replacing the nucleic acid phosphates with a thiophosphates and/or the 2' hydroxyls with 2'-O-methoxys. Other suitable modifications include 2'-deoxy-2'-fluoro-β-D-arabinonucleic acid (2'F-ANA) nucleotides, locked-nucleic acids (LNAs) and ENAs: 2'-O,4'-C-ethylene-bridged nucleic acids. U.S. patent application Ser. No. 11/607,341, filed Nov. 30, 2006 describes how to make and use cleavage resistant oligonucleotides that are suitable in the invention and is herein incorporated by reference in its entirety.

When referring to a downstream probe with a 5' flap the nucleotides of the downstream probe that hybridize to the target are defined to be nucleotides +1 through +X, position +1 is defined as the 5' terminal nucleotide of the hybridized region of the downstream probe, region +2 is defined as the nucleotide which is immediately downstream of position +1 and so on. The nucleotides of the 5' flap are defined to be nucleotides −1 through —X. Position −1 is defined as the 3' terminal nucleotide of the flap region.

As used herein, a "forward primer" according to the invention is preferably 6 to 100, more preferably 8 to 30 and most preferably 20 nucleotides in length. A "forward primer" is at least partially complementary to the target nucleic acid and/or the template nucleic acid at a length of its 3' terminus sufficient to permit its use as a primer for nucleic acid synthesis using the target nucleic acid or the template nucleic acid as a template.

As used herein, an "upstream oligonucleotide" according to the invention is any oligonucleotide which is upstream of a downstream oligonucleotide when annealed to a target or template nucleic acid. For example, an "upstream oligonucleotide" can be the "first oligonucleotide" or "released flap".

As used herein, a "downstream oligonucleotide" according to the invention is any oligonucleotide which is downstream of an upstream oligonucleotide when annealed to the target or template nucleic acid. For example, a "downstream oligonucleotide" can be the "second" or "third" oligonucleotides of the invention.

As used herein, "fully complementary" means that 100% of the nucleotides of an oligonucleotide can hydrogen bond to the corresponding complementary nucleotides of the target of template nucleic acid.

As used herein, "at least partially complementary" as it refers to an oligonucleotide, means that less than 100%, (e.g., 99%, 90%, 75%, 50%, 25% etc. . . . ) of the nucleotides of the oligonucleotide can hybridize (that is form hydrogen bonds) with nucleotides of the target or template nucleic acid under standard stringent conditions. Where an oligonucleotide is "partially complementary", the region of complementary nucleotides may or may not be contiguous nucleotides.

For a "second oligonucleotide", as defined herein, which does not serve as a primer for nucleic acid synthesis, but rather provides a flap at its 5' region, "partial complementarity" refers to a region of nucleotides of non-complementarity with respect to the target nucleic acid, followed by a region of sufficient complementarity to permit hydrogen bonding to the target nucleic acid under standard stringent conditions, wherein the second oligonucleotide is capable of forming a duplex and/or cleavage structure according to the invention. In one embodiment, the region of sufficient complementarity may be 10 contiguous nucleotides or longer (e.g., 20, 30, 40, 50, 100, etc.). In another embodiment, the region of sufficient complementarity includes a sufficient number of non-contiguous nucleotides that are complementary with the target nucleic acid, to permit formation of a hybrid with the target nucleic acid. The 3' terminus of the "second oligonucleotide" can be but is not required to be complementary to the target nucleic acid. Where the 3' terminus is not complementary to the target nucleic acid (for example, in such instances where the 3' terminus is labeled and/or serves a function in detection of the hybridized or non/hybridized oligonucleotide), the region of non-complementary may or may not be contiguous.

In one embodiment, the region of non-complementarity may be contiguous for 1 nucleotide, 2 nucleotides, 3, 4, 5 nucleotides, etc., or over a longer stretch of 10 or greater contiguous nucleotides (20, 30, 40, 50, etc.). In another embodiment, the region of non-complementarity includes a sufficient number of non-contiguous nucleotides that are non-complementary with the target nucleic acid.

A "first flap", "second flap", or a "first released flap", "second released flap" according to the invention, is preferably 6 to 80 and most preferably 10-25 nucleotides in length.

For a "released flap", as defined herein, may serve as an upstream oligonucleotide for a second cleavage reaction. The released flap may hybridize to the first region of a template nucleic acid, however the 3' terminus of the flap may or may not be complementary with the template. In one embodiment, the 3' terminus of the flap is complementary with the template for a length of 10 nucleotides or greater (20, 30, 40, 50, etc.), over contiguous nucleotides. In another embodiment, the 3' terminus of the flap comprises a region of complementarity with the template nucleic acid that includes a sufficient number of non-contiguous nucleotides that are complementary to the template nucleic acid. The region of complementarity must include a sufficient number of contiguous nucleotides to permit formation of a hybrid. In some embodiments, the released flap has one or more 3' terminal nucleotides which are non-complementary to the template nucleic acid.

For a "third oligonucleotide", as defined herein, provides a flap at its 5' region, "partial complementarity" refers to a region of at least 10 contiguous nucleotides (20, 30, 40, 50 nucleotides, etc.) of non-complementarity with respect to the template nucleic acid, followed by a region of sufficient complementarity to permit hydrogen bonding to the template nucleic acid under standard stringent conditions. This region of sufficient complementarity may be 10 contiguous nucleotides or longer (e.g., 20, 30, 40, 50, 100, etc.). The 3' terminus of the "third oligonucleotide" can be but is not required to be complementary to the template nucleic acid. Where the 3' terminus is not complementary to the template nucleic acid (for example, in such instances where the 3' terminus is labeled and/or serves a function in detection of the hybridized or non/hybridized oligonucleotide), it may be non-complementary for 1 nucleotide, 2 nucleotides, 3, 4, 5 nucleotides, etc., or over a longer stretch of 10 or greater contiguous nucleotides (20, 30, 40, 50, etc.) so long as the complementarity of the third oligonucleotide with the template nucleic acid is not disrupted.

A "third oligonucleotide", as defined herein, may provide a 5' flap which may be cleaved and released from a cleavage structure. The region of complementarity with the template must include a sufficient number of contiguous nucleotides to permit formation of a hybrid with the template nucleic acid.

As used herein, "mixing" means combining, in any order.

As used herein, "conditions which permit formation of a duplex" refer to a buffer (i.e., of a specified salt and organic solvent concentration), a temperature, an incubation time, and the concentrations of the components of the duplex (for example a target nucleic acid, a first oligonucleotide and a second oligonucleotide) that are possible and preferably optimal for the formation of a duplex of the invention. For example, in one embodiment of the invention, under "conditions which permit formation of a duplex", a target nucleic acid, a first oligonucleotide and a second oligonucleotide will hybridize such that the 5' region of the second oligonucleotide is a flap.

As used herein, "duplex" refers to a complex comprising a target or template nucleic acid, an upstream oligonucleotide or an upstream primer and at least a 3' region of a downstream. The complementary nucleotide bases of the target or template nucleic acid and each of the upstream oligonucleotide or upstream primer and, at least a 3' region of the downstream oligonucleotide are hybridized due to the formation of hydrogen bonds.

As used herein, "first duplex" refers to a complex comprising a target, a first oligonucleotide and at least a 3' region of a second oligonucleotide, wherein the complementary nucleotide bases of the target or template nucleic acid and each of the first oligonucleotide and, at least a 3' region of a second oligonucleotide are hybridized due to the formation of hydrogen bonds. In some embodiments, the 5' region of a second oligonucleotide and the extension region of the target nucleic acid are not complementary and thus do not form a hybrid in the duplex. The extension region may thus be single-stranded.

As used herein, "first duplex" also refers to a complex comprising a target nucleic acid, an upstream primer and at least a 3' region of a downstream oligonucleotide, wherein the complementary nucleotide bases of the template nucleic acid and each of the upstream primer and at least a 3' region of the downstream oligonucleotide are hybridized due to the formation of hydrogen bonds, wherein the 5' region of the downstream oligonucleotide is a flap.

As used herein, "second duplex" refers to a complex comprising a template nucleic acid, the released flap of the second oligonucleotide, and at least a 3' region of a third oligonucleotide, wherein the complementary nucleotide bases of the template nucleic acid and each of the released flap of the second oligonucleotide, and the at least a 3' region of a third oligonucleotide are hybridized due to the formation of hydrogen bonds with the template nucleic acid.

A "flap" or an "arm" of a branched DNA or DNA/RNA hybrid refers to a 5' polynucleotide that is not hydrogen-bonded to the branched DNA or hybrid DNA/RNA, but is phosphate-bonded to a hydrogen-bonded member of the branched DNA or DNA/RNA hybrid. A flap thus is a nucleic acid strand which hangs off of (i.e., is the branch off of) a double stranded portion of the structure. A "flap" of a cleavage structure according to the invention is preferably about 1-80 nucleotides, more preferably about 5-25 nucleotides and most preferably about 10-20 nucleotides, and is preferably cleaved at a position located at the phosphate positioned at the "elbow" of the branched structure or at any of one to ten phosphates located proximal and/or distal to the elbow of the flap strand. The cleavage position depends on the placement of the upstream oligonucleotide with respect to the downstream oligonucleotide.

As used herein, "elbow" refers to the phosphate bond between the first single stranded nucleotide of the 5' flap and the first double stranded (e.g., hybridized to the target or template nucleic acid) nucleotide. A "flap", according to the invention can be labelled with a detectable label. A "flap" or "arm" according to the invention is cleaved by a cleavage means when it is part of a "cleavage structure", as defined herein, and is released to form a "released arm" or "released flap".

The term "single strand", with respect to a nucleic acid, refers to one polynucleotide strand which may not be hydrogen-bonded to any other nucleic acid, or it may be hydrogen-bonded internally to itself (to form a secondary or tertiary structure) or to another nucleic acid molecule.

The term "single-stranded", with respect to a nucleic acid, refers to a polynucleotide strand which is not hydrogen-bonded to another nucleic acid, and which preferably contains no or little (less than 10%, for example 9%, 5%, 4%, etc. . . . ) internal complementarity.

As used herein, "extension" refers to the addition of nucleoside triphosphates to the 3' end of a first oligonucleotide or the released single-stranded arm of the second oligonucleotide in a conventional DNA polymerization reaction. Thus, the 3' end of the first oligonucleotide and the 3' end of the released single-stranded arm of the second oligonucleotide are not blocked, and are also referred to herein as primers.

Generally the 3' terminus of the template, the first, second and third oligonucleotides will be "blocked" to prohibit creation of an extension product. "Blocking" can be achieved by using non-complementary bases or by adding a chemical moiety such as biotin or a phosphate group to the 3' hydroxyl of the last nucleotide. Blocking can also be achieved by removing the 3'-OH or by using a nucleotide that lacks a 3'-OH such as dideoxynucleotide, or by other methods known to one skilled in the art.

As used herein, "nucleic acid polymerization activity" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyze intervening, annealed probe to release both labeled and unlabeled probe fragments, until synthesis terminates. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase. If the nucleic acid template is RNA, then "nucleic acid polymerization activity" refers to an RNA-dependent polymerization activity, such as reverse transcriptase.

As used herein, "5' to 3' exonuclease activity" or "5'→3' exonuclease activity" refers to that activity of a template-specific nucleic acid polymerase e.g. a 5'→3' exonuclease activity traditionally associated with some DNA polymerases whereby mononucleotides or oligonucleotides are removed from the 5' end of a polynucleotide in a sequential manner, (i.e., *E. coli* DNA polymerase I has this activity whereas the Klenow (Klenow et al., 1970, Proc. Natl. Acad. Sci., USA, 65:168) fragment does not, (Klenow et al., 1971, Eur. J. Biochem., 22:371)), or polynucleotides are removed from the 5' end by an endonucleolytic activity that may be inherently present in a 5' to 3' exonuclease activity.

As used herein, the phrase "substantially lacks 5' to 3' exonuclease activity" or "substantially lacks 5'→3' exonuclease activity" means having less than 10%, 5%, 1%, 0.5%, or 0.1% of the activity of a wild type enzyme. The phrase "lacking 5' to 3' exonuclease activity" or "lacking 5'→3' exonuclease activity" means having undetectable 5' to 3' exonuclease activity or having less than about 1%, 0.5%, or 0.1% of the 5' to 3' exonuclease activity of a wild type enzyme. 5' to 3' exonuclease activity may be measured by an exonuclease assay which includes the steps of cleaving a nicked substrate in the presence of an appropriate buffer, for example 10 mM Tris-HCl (pH 8.0), 10 mM $MgCl_2$ and 50 µg/ml bovine serum albumin) for 30 minutes at 60° C., terminating the cleavage reaction by the addition of 95% formamide containing 10 mM EDTA and 1 mg/ml bromophenol blue, and detecting nicked or un-nicked product.

According to methods of the invention that include two polymerization steps, each of the polymerization steps can be performed by the same nucleic acid polymerization activity or by different nucleic acid polymerization activities.

As used herein, "polymerization", "polymerization activity" or "polymerase activity" refers to the addition of nucleoside triphosphates to the 3' end of an oligonucleotide wherein the 3' end of the oligonucleotide is not blocked.

As used herein, "nucleoside" refers to any purine or pyrimidine base, or modified purine or pyrimidine base, linked to a sugar (e.g. 2-deoxyribose in DNA or ribose in RNA).

As used herein, "nucleotide" refers to any purine or pyrimidine base, or modified purine or pyrimidine base, linked to a sugar, wherein the sugar is linked to a phosphate group.

As used herein, "polymerase chain reaction" or "PCR" refers to an in vitro method for amplifying a specific polynucleotide template sequence. The PCR reaction involves a repetitive series of temperature cycles and is typically performed in a volume of 50-100 µl. The reaction mix comprises dNTPs (each of the four deoxyribonucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule. The PCR process is described in U.S. Pat. Nos. 4,683,195 and 4,683,202, the disclosures of which are incorporated herein by reference.

As used herein, "polymerase chain reaction conditions" or "PCR conditions" refer to a buffer, a set of temperature incubation steps and times that are possible and preferably optimal for conducting PCR. The set of temperature incubation steps and times preferably allow for denaturation, annealing, and extension of the nucleic acids of the invention. PCR reaction conditions are known in the art and described herein.

A "nucleic acid amplification reaction" means an increase in number of a particular nucleic acid sequence and may be accomplished, without limitation, by the in vitro methods of polymerase chain reaction or ligase chain reaction.

As used herein, "nucleic acid amplification reaction conditions" refer to a buffer, a set of temperature incubation steps and times that are possible and preferably optimal for conducting amplification of a nucleic acid. Amplification means an increase in the number of a particular nucleic acid sequence and may be accomplished, without limitation, by the in vitro methods of polymerase chain reaction or ligase chain reaction. Such reaction conditions are known in the art and are described herein. Nucleic acid reaction conditions encompass PCR conditions.

A "nucleic acid amplification reaction mixture" refers to a mixture comprising the components necessary for nucleic acid amplification, such as buffer, dNTPs, water, a target nucleic acid, and a polymerase. Depending on methods for nucleic acid amplification, the necessary components may differ. For example, ligase chain reactions require the presence of a ligase, which may not be needed in certain polymerase chain reactions.

As used herein, a "cleavage structure" refers to a polynucleotide structure comprising at least a duplex nucleic acid having a flap. A "cleavage structure" according to the invention may comprise a target nucleic acid sequence or a template nucleic acid sequence, and also includes an upstream oligonucleotide that is at least partially and may be fully complementary to the target sequence (for example, A-1 of FIG. 1), and a downstream oligonucleotide that is complementary to the target sequence and may comprise a flap (for example FC or F2H in FIG. 1). In one embodiment, a "first cleavage structure" is formed by a first oligonucleotide annealing to the target so that at least a gap separates the complementary portions of the first oligonucleotide and second oligonucleotide. In another embodiment, a "first cleavage structure" is formed by polymerization from the 3' end of the upstream oligonucleotide (primer) to the duplex formed by hydrogen bonding of the second oligonucleotide (i.e., at the junction of the duplex and the flap). In another embodiment, a "second cleavage structure" is formed by a first released flap annealing to the template nucleic acid so that at least a nick separates the complementary portions of the released flap and third oligonucleotide. In another embodiment, a "second cleavage structure" is formed by polymerization from the 3' end of the upstream oligonucleotide (i.e., the released arm of the second oligonucleotide) to the duplex formed by hydrogen bonding of the downstream third oligonucleotide and the template nucleic acid (i.e., at the junction of the duplex and the flap Preferably, the 3' terminus of the upstream oligonucleotide is blocked; blocking the terminus prevents extension of the 3' end of the upstream oligonucleotide.

As used herein, the alternative term "adjacent to" also may be used.

In those reactions where polymerization of a newly synthesized nucleic acid continues completely through the extension region, the distance referred to above would of course be no nucleotides.

Thus, a "cleavage structure" according to the invention may be a second oligonucleotide which is hybridized to a template nucleic acid, and a third oligonucleotide which includes a flap which is the 5' portion of the downstream oligonucleotide.

A "cleavage structure", as used herein, includes a 5' flap and would not encompass a structure which does not include a 5' flap, for example, a double stranded nucleic acid which contains only a 3' flap. As used herein, a "cleavage structure" comprises ribonucleotides or deoxyribonucleotides and thus can be RNA or DNA.

As used herein a "cleavage means" refers to an agent, preferably an enzyme that is specific for, that is, cleaves a cleavage structure according to the invention.

The term "cleavage means" or "cleavage agent" includes an enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). The term "cleavage means" includes agents that cleave a cleavage structure according to the invention comprising an extension region single stranded gap (that is a portion of the extension region that is unhybrized to an upstream primer and/or a downstream probe) of 0-2 nucleotides, 2-20 nucleotides, 20-50 nucleotides or more than 50 nucleotides. The term "cleavage means" also embodies FEN nucleases. The term "FEN nuclease" is an enzyme that possesses 5' exonuclease and/or an endonuclease activity. The term "FEN nuclease" also embodies a 5' flap-specific nuclease. The term "cleavage means" includes a FEN nuclease that cleaves a cleavage structure according to the invention comprising an extension region single stranded gap (that is a portion of the extension region that is unhybrized to an upstream primer and/or a downstream probe) of 0-2 nucleotides, 2-20 nucleotides, 20-50 nucleotides or more than 50 nucleotides.

A "cleavage means" or "cleavage agent" according to the invention includes but is not limited to a FEN nuclease enzyme derived from *Archaeglobus fulgidus, Methanococcus jannaschii, Pyrococcus furiosus*, human, mouse or *Xenopus laevis*. A nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologs of FEN including but not limited to T5 5' to 3' exonuclease, T7 gene 6 exonuclease and T3 gene 6 exonuclease. Preferably, only the 5' to 3' exonuclease domains of Taq, Tfl and Bca FEN nuclease are used. A "cleavage means" according to the invention also includes an agent, preferably an enzyme, that cleaves a cleavage structure according to the invention comprising an RNA/DNA complex wherein the RNA is the template or target nucleic acid. The term "cleavage means" does not include RNAse H.

"Cleavage means" also includes enzymes that can cleave a cleavage structure comprising an upstream oligonucleotide (for example, A-2, FIG. 1) and one or more downstream oligonucleotides (for example, FC, FIG. 1) wherein polymerization has occurred from the 3' end of the upstream oligonucleotide such that the extended 3' end of the upstream oligonucleotide is adjacent to, but does not overlap, the complementary portion of the downstream oligonucleotide (for example C, FIG. 1).

"Cleavage means" also includes enzymes that can cleave a cleavage structure comprising an upstream oligonucleotide (for example A-1, FIG. 1) and a downstream oligonucleotide (for example FC, FIG. 1) which are annealed to a target or template nucleic acid so that at least a nick separates the complementary portions of the oligonucleotides.

As used herein, "adjacent" refers to separated by less than 20 nucleotides, e.g., 15 nucleotides, 10 nucleotides, 5 nucleotides, or 0 nucleotides.

"Cleavage means" or "cleavage agent" also includes enzymes that can cleave a cleavage structure comprising an upstream oligonucleotide (for example A-2, FIG. 1) and one or more downstream oligonucleotides (for example FC, FIG. 1) wherein polymerization has occurred from the 3' end of the upstream oligonucleotide such that the extended 3' end of the upstream oligonucleotide is less than 50 nucleotides from the complementary region of the downstream oligonucleotide (for example C, FIG. 1), but does not overlap the downstream oligonucleotide. According to this embodiment of the invention, the distance between the 3' end of the upstream oligonucleotide across the extension region and sufficiently close to the junction of the flap of the downstream oligonucleotide is of a length that permits a sufficient amount of polymerization to occur from the 3' end of the upstream oligonucleotide to form a cleavage structure according to the invention.

According to methods of the invention that include two cleavage steps, each of the cleavage steps can be performed by the same cleavage means or by a different cleavage means.

A "cleavage means" according to the invention can be a single enzyme that possesses both polymerase and nuclease activity or an enzyme that possesses nuclease activity but lacks polymerase activity.

As used herein, "permitting" means allowing a reaction to proceed such that a duplex or a second duplex, as defined herein, is formed if all of the components required for duplex formation (e.g., the first and second oligonucleotide and the target nucleic acid, or the released flap of the second oligonucleotide, the template nucleic acid and the third oligonucleotide) are present. "Permitting" also means adding any required components (e.g., the released flap of the second oligonucleotide) to a mixture comprising the template and the third oligonucleotide, and allowing the reaction to proceed such that a "second duplex", as defined herein, is formed. "Permitting" also means adding any required components (e.g., the released flap of the second oligonucleotide) to a mixture comprising the template the third oligonucleotide, and the fourth oligonucleotide, and allowing the reaction to proceed such that a "second duplex", as defined herein, is formed. "Permitting" also means adding any required components (e.g., template and third oligonucleotide) to the released flap of the second oligonucleotide and allowing the reaction to proceed such that a duplex or a second duplex, as defined herein, is formed.

As used herein, "detecting a target nucleic acid sequence" or "measuring a target nucleic acid sequence" refers to determining the presence of a particular target nucleic acid sequence in a sample or determining the amount of a particular target nucleic acid sequence in a sample as an indication of the presence of a target nucleic acid sequence in a sample. The amount of a target nucleic acid sequence that can be measured or detected is preferably about 1 molecule to $10^{20}$ molecules, more preferably about 100 molecules to $10^{17}$ molecules and most preferably about 1000 molecules to $10^{14}$ molecules. According to one embodiment of the invention, the detected nucleic acid is derived from the labelled downstream oligonucleotide, defined herein (for example F2H in FIG. 1). According to the present invention, a first member of a pair of interactive labels is attached to the 5' flap of the downstream oligonucleotide and a second member of the pair of interactive labels is attached to the 3' region of the downstream oligonucleotide.

An oligonucleotide according to the invention (e.g., a first, second, or third oligonucleotide) can be labelled by attaching a label to the 5' end, the 3' end or by labelling the oligonucleotide internally.

In another embodiment, the probe (downstream oligonucleotide) is labeled with a FRET pair. The members of this interactive pair of labels interact when the probe (e.g., downstream oligonucleotide) is not cleaved or cleaved by an invasive cleavage reaction. Cleavage of the probe by a non-invasive cleavage reaction generates a detectable signal (e.g. fluorescence). The pair of interactive labels may be placed anywhere along the probe so long as the pair of interactive labels interact and produce a detectable signal when the probe is cleaved by a non-invasive cleavage reaction but do not produce a detectable signal when the oligonucleotide is cleaved by an invasive cleavage reaction.

In one embodiment the second or third oligonucleotide comprises a pair of interactive labels. In a further embodiment, a first member of the pair of interactive labels is operatively coupled to the 5' flap of said second or third oligonucleotide. In yet a further embodiment, a second member of the pair of interactive labels is operatively coupled to position +1 of the second or third oligonucleotide. Alternatively, the second member of the pair of interactive labels is operatively coupled to position +2, +3, +4 or +5 of the second or third oligonucleotide. The pair of interactive labels may be a fluorophore and a quencher.

As used herein "detection of a signal generated by the cleavage of a third oligonucleotide" refers to determining the presence of a cleaved labeled third oligonucleotide in a sample or determining the amount of the cleaved labeled third oligonucleotide. Methods well known in the art and described herein can be used to detect or measure the cleavage of the labelled third oligonucleotide. The presence or amount of a cleaved labelled third oligonucleotide may be determined by detecting a change in fluorescence. For example, upon cleavage of the third oligonucleotide and separation of the pair of interactive labels present on the third oligonucleotide. The detection methods described herein are operative for detecting a cleaved third oligonucleotide wherein any amount of a cleaved third oligonucleotide is detected whether that is a small or large proportion of the cleaved third oligonucleotides generated in the reaction. A method of detecting or measuring cleavage of the third oligonucleotide will be appropriate for measuring or detecting the labelled moiety that is present on the cleaved third oligonucleotide.

As used herein, "labelled flaps" refers to cleaved mononucleotides or small oligonucleotides or oligonucleotides derived from the labelled cleavage structure according to the invention wherein the cleaved oligonucleotides are preferably between about 6-80 nucleotides, and more preferably between 10-25 nucleotides, which are cleaved from a cleavage structure by a nuclease and can be detected by methods well known in the art and described herein.

In one embodiment, the first oligonucleotide and the second oligonucleotide hybridize to non-overlapping regions of the target nucleic acid, and the released flap of the second oligonucleotide and the third oligonucleotide hybridize to non-overlapping regions of the template nucleic acid.

As used herein, a cleavage structure may be referred to as "overlapping" or "invasive" when one or more nucleotides of an upstream oligonucleotide (e.g., primer) are complementary to the same region of the target as a downstream oligonucleotide (e.g., probe). In this embodiment, the two oligonucleotides will compete for binding to the same region of the target.

As used herein, "non-overlapping" or "non-invasive" means that if two oligonucleotides are hybridized to the target (or template) nucleic acid, then the two oligonucleotides will not compete with each other with respect to hybridization with the target (or template) nucleic acid. Thus, the two respective hybridization regions of the target (or template) nucleic acid do not involve one or more nucleotides in common.

As used herein, "gap" means a portion of the target or template of at least one nucleotide between the 3' terminal complementary nucleotide of the upstream oligonucleotide and the most 5' complementary nucleotide of a downstream oligonucleotide.

As used herein, "nick" means a portion of the target or template that is between the 3' terminal complementary nucleotide of the upstream oligonucleotide and the most 5' complementary nucleotide of the downstream oligonucleotide when they are directly abutting. A nick is present when the oligonucleotides do not overlap and have less than a gap between them, e.g., 0 nucleotides, directly abutting.

Nucleic acid polymerases exhibiting strand displacement activity and useful according to the invention include but are not limited to archaeal DNA polymerases with "temperature activated" strand displacement activity (exo plus and exo minus versions of Vent, Deep Vent, Pfu, JDF-3, KOD (LTI's tradename Pfx), Pwo, 9 degrees North, *Thermococcus aggregans, Thermococcus gorgonarius*), and eubacterial DNA polymerases with strand displacement activity (exo minus Bst, exo minus Bca, Genta, Klenow fragment, exo minus Klenow fragment exo minus T7 DNA polymerase (Sequenase).

In one embodiment, the cleavage means comprises a 5' nuclease activity for which cleavage of a flap from a cleavage structure is dependent upon the formation of duplex DNA at the site of cleavage.

In another embodiment, a single enzyme comprises a polymerization activity and a cleavage means.

In another embodiment, a single enzyme comprising a polymerization activity and a cleavage means is selected from the group consisting of *E. coli* DNA polymerase I, T7 DNA polymerase, Tth DNA polymerase, or Taq DNA polymerase.

In yet another embodiment, a first enzyme comprises a polymerization activity and a second enzyme comprises a cleavage means.

In another embodiment, the cleavage means comprises a FEN-1 nuclease.

In another embodiment, the method is carried out isothermally.

As used herein, "isothermally" refers to a temperature that supports, and is preferably optimal, for the activity of a cleavage means and a polymerization means according to the invention.

In yet another embodiment, the method is carried out under a series of reaction conditions.

As used herein, "a series of reaction conditions" refers to two or more temperature incubations that are optimal for the steps of duplex formation, and cleavage according to the invention. For example, a series of reaction conditions include PCR reaction and nucleic acid reaction conditions.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference.

The methods of the invention can be performed isothermally or performed under conditions of thermal cycling, e.g., PCR, nucleic acid amplification.

The invention provides for a method of generating a signal indicative of the presence of a target nucleic acid sequence in a sample comprising the steps of forming a labeled cleavage structure by incubating a target nucleic acid sequence with upstream and downstream oligonucleotides, and cleaving the cleavage structure with a nuclease. The invention also provides for methods of generating a signal indicative of the presence of a target nucleic acid sequence in a sample in a sequential cleavage reaction. The method of the invention can be used in a PCR based assay as described below and in the examples.

A labeled cleavage structure comprising an upstream oligonucleotide (for example A-1, FIG. 1), labeled downstream oligonucleotide probe having a 5' non-complementary flap (for example FC, FIG. 1) and a target nucleic acid sequence (for example A'C', FIG. 1) is formed as described in the section entitled "Cleavage Structure". The downstream oligonucleotide is labeled with a pair of interactive moieties positioned so that only non-invasive cleavage structures are detectable.

Briefly, a cleavage structure is formed and cleaved in the presence of a target nucleic acid sequence, an upstream oligonucleotide (for example A-1, FIG. 1), a labeled downstream probe (for example FC, FIG. 1 (shown unlabeled in FIG. 1) amplification primers (A-2 and R, FIG. 1, optional) specific for the target nucleic acid sequence, a nucleic acid polymerase (optional), a FEN nuclease and an appropriate buffer (for example 1× Pfu buffer, Stratagene, or probe buffer with 15 mM of Tris-HCL (pH8), 50 mM KCL, 5.5 mM $MgCl_2$, 8% glycerol, 1% DMSO) in a PCR reaction with the following thermocycling parameters: 95° C. for 2 minutes and 40 cycles of 95° C. for 15 sec (denaturation step), 60° C. for 60 sec (annealing/extension step). The forward and reverse primers may be extended to amplify the target. The upstream oligonucleotide and labeled downstream oligonucleotide anneal to the target so as to form a cleavage structure. The resulting labeled structure is cleaved with a FEN nuclease according to the invention. The downstream oligonucleotide is cleaved at or upstream of the elbow, resulting in the separation of the pair of interactive labels. This will produce a detectable cleavage event. In the event the cleavage structure is invasive (e.g., extension of the forward primer into the region of the downstream oligonucleotide which is complementary with the target) the downstream oligonucleotide is cleaved downstream of position +1. Thus, a pair of interactive labels appropriately spaced to distinguish between invasive and non-invasive cleavage reactions (e.g., FAM on the 5' flap and BHQ at the +1 position) will be cleaved downstream of both labels and no detectable signal will be produced.

FIG. 1 illustrates the one embodiment of the invention utilizing a sequential cleavage reaction under PCR conditions. Both a first and a second cleavage reaction include a target (template) nucleic acid, upstream oligonucleotide (first oligonucleotide of the first cleavage reaction or released flap of the second cleavage reaction) and downstream oligonucleotide (second oligonucleotide of the first cleavage reaction or third oligonucleotide of the second cleavage reaction).

In this embodiment, a sequential detection reaction produces a detectable signal indicative of the presence of a target nucleic acid. The detectable signal is only produced when both the first and second cleavage reactions are non-invasive. In the event the cleavage reaction is invasive, no signal is produced. The cleavage structure is invasive when the complementary portions of both (1) the upstream and downstream oligonucleotides are adjacent (no non-complementary target/template nucleotides between them) and (2) the upstream oligonucleotide has a 3' region which overlaps the complementary portion of the downstream oligonucleotide. If either of these two requirements is not met, the reaction is non-invasive. Thus, if the upstream oligonucleotide overlaps the complementary portion of the downstream oligonucleotide.

The first cleavage reaction (FIG. 1A) includes a target nucleic acid (A'C'), a first oligonucleotide (A-1), a second oligonucleotide (FC), a reverse primer (R), a forward primer (A-2), a polymerase and a cleavage agent. The second cleavage reaction (FIG. 1B) utilizes a template nucleic acid (F'H'), the released flap generated in the first cleavage reaction (F), a third oligonucleotide (F2H), and a cleavage agent.

The target and template nucleic acids have, in 3' to 5' order, a first region (A' or F'), and a second region (C' or H').

The first oligonucleotide (A-1) is complementary to the first region of the target (A') and has a 3' terminal nucleotide which is non-complementary to the target. The second oligonucleotide (FC) has a 5' flap (F) which is non-complementary to the target and a 3' region which is complementary to the second region (C') of the target. However, the 5' flap (F) is complementary to the first region of the template nucleic acid (F') and includes a single nucleotide at the 3' end of the flap which is non-complementary to the template nucleic acid. The 3' non-complementary nucleotide acts as a block that inhibits the extension of the oligonucleotide by a polymerase.

The third oligonucleotide (F2H) has a 5' flap (F2) which is non-complementary to the template and a 3' region which is complementary to the second region (H') of the template. The hinge or elbow region is where the complementary and non-complementary regions of the third oligonucleotide meet. The third oligonucleotide is operatively coupled to a pair of interacting labels. The labels produce a signal when they are separated upon cleavage of the third oligonucleotide (e.g., cleavage at the elbow of the third oligonucleotide), but do not produce a signal when the third oligonucleotide is cleaved downstream of the labels. In some embodiments, the detectable labels are FAM and BHQ. In one embodiment, FAM is operatively coupled to the 5' flap of the third oligonucleotide and BHQ is operatively coupled to the first nucleotide of the complementary portion of the third oligonucleotide (+1).

The first reaction includes a mixture of two sets of upstream oligonucleotides, the first oligonucleotide and the primer. In this embodiment, both the primer and first oligonucleotide are complementary to the same general region of the target, so that annealing of one precludes annealing of the other. The first oligonucleotide forms a non-invasive cleavage structure while the primer serves to amplify the target. In the event the primer forms an invasive cleavage structure, the second oligonucleotide is cleaved downstream of the elbow so as to prevent any detectable signal from being produced in the second cleavage reaction.

In a reaction utilizing the first oligonucleotides, a single non-complementary template nucleic acid separates the complementary portions of the upstream oligonucleotide from the complementary portion of the downstream oligonucleotide. The 3' non-complementary nucleotide inhibits extension of the first oligonucleotide and directs FEN to cleave the second oligonucleotide at the elbow. This cleavage generates a released flap which is complementary to the first region of the template nucleic acid and which includes a 3' nucleotide which is non-complementary to the template.

The reverse primer anneals to the complementary strand of the target and is extended by the polymerase.

Cleavage of the second oligonucleotide during the first cleavage reaction produces a released flap which is essential for the second cleavage reaction. The released flap anneals to the first region of the template and the third oligonucleotide anneals to the second region of the template.

The released flap anneals to the target so that one or two non-complementary template nucleotides separate the complementary portions of the released flap and third oligonucleotide when they are annealed to the template. The released flap has a 3' non-complementary nucleotide which inhibits its extension by a polymerase and favors formation of a second non-invasive cleavage structure. The third oligonucleotide is cleaved by FEN at the elbow, separating the fluorescer and quencher to produce a detectable signal.

In a sequential cleavage reaction, preferably the first oligonucleotide has a single 3' terminal non-complementary nucleotide. In further embodiments, when annealed to the target the complementary portion of the first oligonucleotide and of the second oligonucleotide are separated by one non-complementary target nucleic acid. The released flap will also preferably have a single 3' terminal non-complementary nucleotide. Furthermore the complementary portions of the released flap and third oligonucleotide will be separated by preferably two non-complementary template nucleic acids.

The methods of the invention can also be used in non-PCR based applications to detect a target nucleic acid sequence. In some embodiments, the may be immobilized on a solid support. Methods of immobilizing a nucleic acid sequence on a solid support are known in the art and are described in Ausubel F M et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports useful according to the invention, CPG, Inc. A solid support useful according to the invention includes but is not limited to silica based matrices, membrane based matrices and beads comprising surfaces including, but not limited to styrene, latex or silica based materials and other polymers. Magnetic beads are also useful according to the invention. Solid supports can be obtained from the above manufacturers and other known manufacturers.

The invention also provides for a non-PCR based assay for detecting a target nucleic acid sequence in solution. The method of the invention can be used to detect naturally occurring target nucleic acid sequences in solution including but not limited to RNA and DNA that is isolated and purified from cells, tissues, single cell organisms, bacteria or viruses. The method of the invention can also be used to detect synthetic targets in solution, including but not limited to RNA or DNA oligonucleotides, and peptide nucleic acids (PNAs). Non-PCR assays include but are not limited to detection assays involving isothermal amplification, where the amount of nucleic acid synthesized by the 3'-5' synthetic activity increases linearly or exponentially, and a FEN nuclease is used to cleave the downstream probe.

I. Nucleic Acids

A. Nucleic Acid Sequences Useful in the Invention

The invention provides for methods of detecting or measuring a target nucleic acid sequence utilizing oligonucleotides, primers and probes. As used herein, the terms "nucleic acid", "polynucleotide" and "oligonucleotide" refer to primers, probes (upstream and downstream oligonucleotides), and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites) or analogs such as protein nucleic acid (PNA). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The complement of a nucleic acid sequence as used herein refers to an oligonucleotide which, when aligned with the nucleic acid sequence such that the 5' end of one sequence is paired with the 3' end of the other, is in "antiparallel association."

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semi synthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

Because mononucleotides are reacted to make oligonucleotides in a manner such that the 5' phosphate of one mononucleotide pentose ring is attached to the 3' oxygen of its neighbor in one direction via a phosphodiester linkage, an "end" or "terminus" of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence which is internal within a larger oligonucleotide, may be said to be a 5' or a 3' region, depending upon whether it is located closer to the 5' or 3' terminus of the molecule.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

B. Oligonucleotides Useful According to the Invention

The invention provides for oligonucleotide primers, oligonucleotide probes (upstream and downstream oligonucleotides), and template nucleic acids useful for detecting or measuring a target nucleic acid, for amplifying a target nucleic acid sequence, and for forming a cleavage structure according to the invention.

As used herein, "amplifying" refers to producing additional copies of a nucleic acid sequence by isothermal methods or by methods that require thermal cycling, including the method of the polymerase chain reaction.

1. Primers

The invention provides for forward and reverse primers that are extended by polymerization.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Conditions suitable for synthesis of a primer extension product include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier.

Primers useful according to the invention are also designed to have a particular melting temperature (Tm) by the method of melting temperature estimation. Commercial programs, including Oligo™, Primer Design and programs available on the internet, including Primer3 and Oligo Calculator can be used to calculate a Tm of a nucleic acid sequence useful according to the invention. Preferably, the Tm of an amplification primer useful according to the invention, as calculated for example by Oligo Calculator, is preferably between about 15 and 80° C. and more preferably between about 50 and 60°

C. Oligonucleotide primers can be designed with these considerations in mind and synthesized according to the following methods.

a. Oligonucleotide Primer Design Strategy

The design of a particular oligonucleotide primer according to the invention, involves selecting a sequence that is capable of recognizing the target sequence, but has a minimal predicted secondary structure. Furthermore, the Tm of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GenBank database (or other available databases).

The design of a primer is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and AMPLIFY (described in Ausubel et al., 1995, Short Protocols in Molecular Biology, 3rd Edition, John Wiley & Sons). In one embodiment, primers are designed with sequences that serve as targets for other primers to produce a PCR product that has known sequences on the ends which serve as targets for further amplification (e.g. to sequence the PCR product). If many different target nucleic acid sequences are amplified with specific primers that share a common 'tail' sequence', the PCR products from these distinct genes can subsequently be sequenced with a single set of primers. Alternatively, in order to facilitate subsequent cloning of amplified sequences, primers are designed with restriction enzyme site sequences appended to their 5' ends. Thus, all nucleotides of the primers are derived from a target nucleic acid sequence or sequences adjacent to a target nucleic acid sequence, except for the few nucleotides necessary to form a restriction enzyme site. Such enzymes and sites are well known in the art. If the genomic sequence of a target nucleic acid sequence and the sequence of the open reading frame of a target nucleic acid sequence are known, design of particular primers is well within the skill of the art.

b. Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

C. Probes

The invention provides for oligonucleotides probes useful for forming a cleavage structure or a labeled cleavage structure as defined herein. Methods of preparing a labeled cleavage structure according to the invention are provided in the section entitled "Cleavage Structure". The invention provides for first, second, and third oligonucleotides (all defined herein) that are components of one or more of a first or second duplex, according to the invention, or a first or second cleavage structure, according to the invention. As used herein, "probe" refers to any one of a first, second or third oligonucleotide according to the invention.

A "first oligonucleotide" according to the invention is preferably 10-120, more preferably 15-40 and most preferably 20-30 nucleotides in length. A "first oligonucleotide" is at least partially complementary to the first region of a target nucleic acid. In one embodiment, the first oligonucleotide has a single 3' terminal nucleotide which is non-complementary to the target. In another embodiment, the first oligonucleotide has two or more 3' terminal nucleotides which are non-complementary to the target.

A "second oligonucleotide" according to the invention is preferably 20-120, more preferably 25-45 and most preferably 25-35 nucleotides in length. A "second oligonucleotide" comprises a 3' and a 5' region. The 3' region of a "second oligonucleotide" is at least partially complementary to the target nucleic acid. A 5' region of a "second oligonucleotide" is preferably 8 to 80 and most preferably 10 to 20 nucleotides in length. In one embodiment of the invention, a 5' region of a "second oligonucleotide" is at least partially complementary to a region of a template nucleic acid. In another embodiment of the invention, the 5' region of the second oligonucleotide according to the invention is not complementary to a target nucleic acid.

A "third oligonucleotide" according to the invention is preferably 20-120, more preferably 25-45 and most preferably 25-35 nucleotides in length. A "third oligonucleotide" comprises a 3' and a 5' region. Third oligonucleotide according to the invention comprises a 3' region that is at least partially complementary to a region of a template nucleic acid and is preferably 8 to 80 and most preferably 10-20 nucleotides. A 5' region of a "third oligonucleotide" is preferably 8 to 80 and most preferably 10 to 20 nucleotides in length. In an embodiment of the invention, the 5' region of the "third oligonucleotide" according to the invention is not complementary to a template nucleic acid.

Generally the 3' terminus of the probe will be "blocked" to prohibit incorporation of the probe into a primer extension product.

1. Labels

A probe according to the invention can be labeled (e.g., by the attachment of a radiolabel, a fluorescent label a quencher or any of the labels recited in the section entitled "Cleavage Structure"). A labeled oligonucleotide probe is prepared according to methods well known in the art and described herein (see Sambrook et al., supra; Ausubel et al., supra).

2. Probes Comprising a Secondary Structure

A "probe" according to one embodiment of the invention can be a single stranded nucleic acid comprising a region or regions that are complementary to a target or a template nucleic acid sequence (e.g., target or template nucleic acid binding sequences). A "probe" according to this embodiment of the invention has a secondary structure that changes upon binding of the probe to the target or template nucleic acid sequence and can further comprise a binding moiety. A "probe" according to this embodiment of the invention binds to a target or template nucleic acid sequence to form a cleavage structure that can be cleaved by a cleavage means, wherein cleaving is performed at a cleaving temperature, and wherein the secondary structure of the probe when not bound to the target or template nucleic acid sequence is preferably stable at or below the cleaving temperature. A probe according to the invention cannot be cleaved to generate a signal by a "cleavage means", as defined herein, prior to binding to a target or template nucleic acid. In one embodiment of the invention, a probe may comprise a region that cannot bind or is not complementary to a target or template nucleic acid sequence. In another embodiment of the invention, a probe does not have a secondary structure when bound to a target or template nucleic acid.

Figure 5:
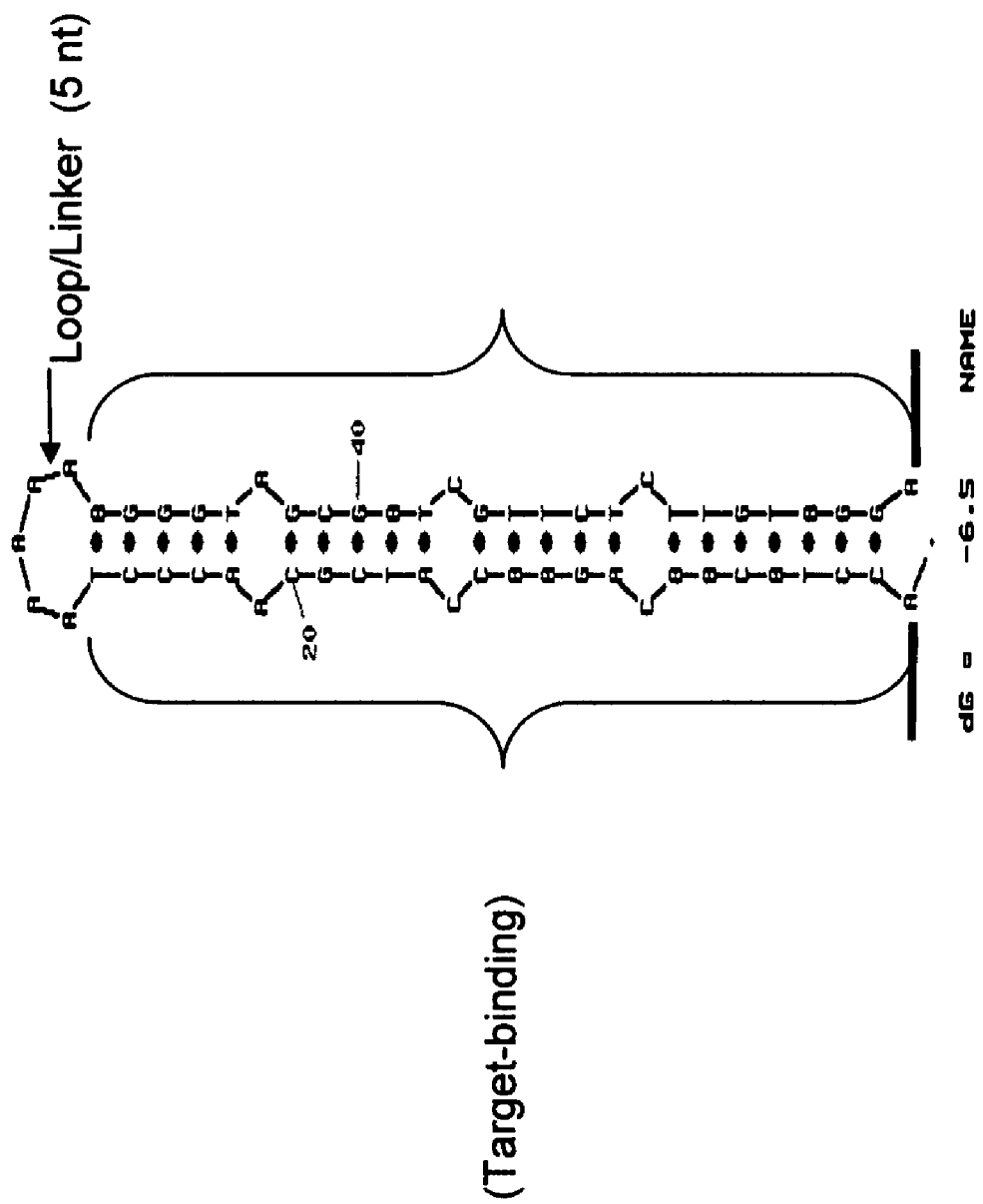
FIG. 5 is a representation of a key probe.

As used herein, "secondary structure" refers to a three-dimensional conformation (for example a hairpin, a stem-loop structure (e.g., FIG. 5), an internal loop, a bulge loop, a branched structure or a pseudoknot; multiple stem loop structures, cloverleaf type structures or any three dimensional structure. As used herein, "secondary structure" includes tertiary, quaternary etc. ... structure. A probe comprising such a three-dimensional structure binds to a target or template nucleic acid sequence to form a cleavage structure that can be cleaved by a cleavage means at a cleaving temperature. The three dimensional structure of the probe when not bound to the target or template nucleic acid sequence is preferably stable at or below the cleaving temperature. "Secondary structure" as used herein, means a sequence comprising a first single-stranded sequence of bases (referred to herein as a "complementary nucleic acid sequence") followed by a second complementary sequence either in the same molecule, or in a second molecule comprising the probe, folds back on itself to generate an antiparallel duplex structure, wherein the single-stranded sequence and the complementary sequence (that is, the complementary nucleic acid sequences) anneal by the formation of hydrogen bonds. Oligonucleotide probes, as used in the present invention include oligonucleotides comprising secondary structure, including, but not limited to key probes (FIG. 5).

As used herein, first and second "complementary" nucleic acid sequences are complementary to each other and can anneal by the formation of hydrogen bonds between the complementary bases.

A "probe" according to this embodiment of the invention can be unimolecular. As used herein, a "unimolecular" probe comprises a single molecule that binds to a target or template nucleic acid sequence to form a cleavage structure that can be cleaved by a cleavage means, wherein cleaving is performed at a cleaving temperature, and wherein the secondary structure of the "unimolecular" probe when not bound to the target or template nucleic acid sequence is preferably stable at or below the cleaving temperature. Unimolecular probes useful according to the invention include but are not limited to key probes.

As used herein, a "molecule" refers to a polynucleotide.

A "probe" or a "molecule" comprising a probe, according to this embodiment of the invention, is 5-10,000 nucleotides in length, ideally from 17-40 nucleotides in length, although probes or a molecule comprising a probe of different lengths are useful.

A "probe" according to this embodiment of the invention has a target or template nucleic acid binding sequence that is from about 5 to about 10,000 nucleotides, and preferably from 10 to about 140 nucleotides. In one embodiment of the invention, a "probe" according to the invention comprises at least first and second complementary nucleic acid sequences or regions that are 3-250, preferably 4-50, and more preferably 17-40 nucleotides long. The first and second complementary nucleic acid sequences may or may not have the same length. The invention provides for a probe wherein either the first or second complementary nucleic acid sequences is complementary to the target or template nucleic acid. In another embodiment the first and/or second complementary nucleic acid sequences are located upstream (5') of the target or template nucleic acid binding site. Alternatively, the first and/or second complementary nucleic acid sequences can be located downstream (3') of the target or template nucleic acid binding site. The actual length will be chosen with reference to the target or template nucleic acid binding sequence such that the secondary structure of the probe is stable when the probe is not bound to the target or template nucleic acid at the temperature at which cleavage of a cleavage structure comprising the probe bound to a target or template nucleic acid is performed. As the target or template nucleic acid binding sequence increases in size up to 500 nucleotides, the length of the complementary nucleic acid sequences may increase up to 15-125 nucleotides. For a target or template nucleic acid binding sequence greater than 100 nucleotides, the length of the complementary nucleic acid sequences are not increased further. If the probe is also an allele-discriminating probe, the lengths of the complementary nucleic acid sequences are more restricted, as is discussed below.

As used herein, the "target nucleic acid binding sequence" refers to the region of the probe that binds specifically to the target nucleic acid.

As used herein, the "template nucleic acid binding sequence" refers to the region of the probe that binds specifically to the template nucleic acid.

A probe according to the invention is capable of forming a secondary structure, as defined herein, (including a stem loop, a hairpin, an internal loop, a bulge loop, a branched structure and a pseudoknot) or multiple secondary structures or any three-dimensional structure as defined herein.

For example, according to one embodiment of the present invention, a probe can be an oligonucleotide with secondary structure such as a hairpin or a stem-loop, and includes, but is not limited to molecular beacons, safety pins, scorpions, sunrise/amplifluor probes, and key probes.

Molecular beacon probes comprise a hairpin, or stem-loop structure which possesses a pair of interactive signal generating labeled moieties (e.g., a fluorophore and a quencher) effectively positioned to quench the generation of a detectable signal when the beacon probe is not hybridized to the target nucleic acid sequence. The loop comprises a region that is complementary to a target nucleic acid. The loop is flanked by 5' and 3' regions ("arms") that reversibly interact with one another by means of complementary nucleic acid sequences when the region of the probe that is complementary to a nucleic acid target sequence is not bound to the target nucleic acid. Alternatively, the loop is flanked by 5' and 3' regions ("arms") that reversibly interact with one another by means of attached members of an affinity pair to form a secondary structure when the region of the probe that is complementary to a nucleic acid target sequence is not bound to the target nucleic acid. As used herein, "arms" refers to regions of a molecular beacon probe that a) reversibly interact with one another by means of complementary nucleic acid sequences when the region of the probe that is complementary to a nucleic acid target sequence is not bound to the target nucleic acid or b) regions of a probe that reversibly interact with one another by means of attached members of an affinity pair to form a secondary structure when the region of the probe that is complementary to a nucleic acid target sequence is not bound to the target nucleic acid. When a molecular beacon probe is not hybridized to target, the arms hybridize with one another to form a stem hybrid, which is sometimes referred to as the "stem duplex". This is the closed conformation. When a molecular beacon probe hybridizes to its target the "arms" of the probe are separated. This is the open conformation. In the open conformation an arm may also hybridize to the target. Such probes may be free in solution, or they may be tethered to a solid surface. When the arms are hybridized (e.g., form a stem) the quencher is very close to the fluorophore and effectively quenches or suppresses its fluorescence, rendering the probe dark. Such probes are described in U.S. Pat. No. 5,925,517 and U.S. Pat. No. 6,037,130.

As used herein, a molecular beacon probe can also be an "allele-discriminating" probe as described herein.

An additional oligonucleotide probe useful in the present invention is the key probe. The key probe is described in U.S. application Ser. No. 11/351,129, filed Feb. 9, 2006 which is herein incorporated by reference in its entirety. The key probe can be formed from a target binding oligonucleotide joined to its complementary sequence, optionally through a linker oligonucleotide sequence, to form a hairpin structure comprising stem and, optionally, loop portions (See FIG. 5). The loop portion contains the optional linker sequence, or just a covalent bond joining the ends of the first and second sequences. The linker sequence, which forms the loop structure, may or may not hybridize to the target sequence. The stem portion optionally contains one or more mismatches between the first and second sequences; the number of mismatches can be used to adjust the melting temperature of the probe. The stem portion may also contain modified nucleotides, for example minor groove binders or LNA, which can alter the affinity of the probe for the target sequence and also can be used to adjust the melting temperature. The key probe may also contain an interactive pair of labels, for example a fluorophore/quencher pair, attached at or near the ends of the probe such that a detectable signal, e.g., increased fluorescence emission of the fluorophore, is produced when the probe hybridizes to the target sequence.

For key probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long. The stability of the interaction between the regions of a probe that reversibly interact with one another by means of complementary nucleic acid sequences is determined by routine experimentation to achieve proper functioning. In addition to length, the stability of the interaction between the regions of a probe that reversibly interact with one another by means of complementary nucleic acid sequences between the regions of a probe that reversibly interact with one another by means of complementary nucleic acid sequences can be adjusted by altering the G—C content and inserting destabilizing mismatches. One of the regions of a probe that reversibly interact with one another by means of complementary nucleic acid sequences can be designed to be partially or completely complementary to the target.

A wide range of fluorophores may be used in probes according to this invention. Available fluorophores include coumarin, fluorescein, tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges.

Suitable quenchers described in the art include particularly DABCYL and variants thereof, such as DABSYL, DABMI and Methyl Red. Fluorophores can also be used as quenchers, because they tend to quench fluorescence when touching certain other fluorophores. Preferred quenchers are either chromophores such as DABCYL or malachite green, or fluorophores that do not fluoresce in the detection range when the probe is in the open conformation.

In one embodiment the downstream probe includes a pair of interactive labels. In a further embodiment, a first member of the pair of interactive labels is operatively coupled to the 5' flap of said downstream oligonucleotide. In a further embodiment, a second member of the pair of interactive labels is operatively coupled to position +1 of the downstream oligonucleotide. In yet another embodiment, the second member of the pair of interactive labels is operatively coupled to position +2 of said downstream oligonucleotide. In yet a further embodiment, the pair of interactive labels comprises a fluorophore and a quencher.

Generally the 3' terminus of the probe will be "blocked" to prohibit incorporation of the probe into a primer extension product if an active polymerase is used in the reaction. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

The term probe encompasses an allele-discriminating probe. As used herein, an "allele-discriminating" probe preferentially hybridizes to perfectly complementary target nucleic acid sequences and discriminates against sequences that vary by at least one nucleotide. A nucleic acid sequence which differs by at least one nucleotide, as compared to a target nucleic acid sequence, hereafter referred to as a "target-like nucleic acid sequence", is thus not a target nucleic acid sequence for an allele-discriminating probe according to the invention.

Allele-discriminating probes do not hybridize sufficiently to a target-like nucleic acid sequence that contains one or more nucleotide mismatches as compared to the target nucleic acid complementary sequence, at a particular temperature or within a range of temperatures determined by experimental optimization according to methods well known in the art, and thus do not undergo a change in secondary structure upon binding to a target-like nucleic acid sequence in the presence of only a target-like nucleic acid sequence, and under conditions that would support hybridization of the allele discriminating probe to a target nucleic acid sequence.

In one embodiment, an "allele-discriminating probe" according to the invention refers to a probe that hybridizes to a target-like nucleic acid sequence that varies by at least one nucleotide from the target nucleic acid sequence, wherein the variant nucleotide(s) is/are not located in the allele-discriminating site. According to this embodiment of the invention, "an allele-discriminating probe" cannot bind to a target-like nucleic acid sequence that also varies by at least one nucleotide in the allele-discriminating site at a particular temperature or within a range of temperatures determined by experimental optimization according to methods well known in the art. Single nucleotide differences only affect the percentage of a probe that is bound to a target or target-like nucleic acid sequence. For example, the invention provides for a perfectly matched probe, wherein as much as 100% of the target or template is in a probe-target or probe-template complex (e.g., is bound by probe), in the presence of excess probe. The invention also provides for probes comprising at least a single base mismatch wherein at least 1-5% and preferably 5-10% of the target-like or template-like sequence is bound by the probe under the same conditions used to form a complex comprising a target or template sequence and a perfectly matched probe.

As used herein, "allele-discriminating site" refers to a region of a target nucleic acid sequence that is different (i.e., by at least one nucleotide) from the corresponding region in all possible alleles comprising the target nucleic acid sequence.

Allele-discriminating probes useful according to the invention also include probes that bind less effectively to a target-like sequence, as compared to a target sequence. The effectiveness of binding of a probe to a target sequence or a target-like sequence is measured in a FRET assay, performed at a temperature that is below (at least 5° C. and preferably 10° C. or more) the Tm of the secondary structure of probe, in the presence of a target-like sequence or a target sequence. The change in the level of fluorescence in the presence or absence of a target sequence compared to the change in the level of fluorescence in the presence or absence of a target-like sequence, provides an effective measure of the effectiveness of binding of a probe to a target or target-like sequence.

In a method according to the invention, a probe that binds less effectively to a target-like sequence as compared to a target sequence would undergo a smaller (e.g., preferably 25-50%, more preferably 50-75% and most preferably 75-90% of the value of the change in fluorescence upon binding to a target nucleic acid sequence) change in secondary structure, as determined by measuring fluorescence in a FRET assay as described herein, upon hybridization to a target-like sequence as compared to a target nucleic acid sequence. In a method according to the invention, a probe that binds less effectively to a target-like sequence as compared to a target sequence would generate a signal that is indicative of the presence of a target-like nucleic acid sequence in a sample. However, the intensity of the signal would be altered (e.g., preferably 25-50%, more preferably 50-75% and most preferably 75-90% less than or more than the value of the change in fluorescence upon binding to a target nucleic acid sequence) the intensity of a signal generated in the presence of a target sequence, as described hereinabove for a smaller change.

A "signal that is indicative of the presence of a target nucleic acid sequence" or a "target-like nucleic acid sequence" refers to a signal that is equal to a signal generated from 1 molecule to $10^{20}$ molecules, more preferably about 100 molecules to $10^{17}$ molecules and most preferably about 1000 molecules to $10^{14}$ molecules of a target nucleic acid sequence or a target-like nucleic acid sequence.

D. Target Nucleic Acid

The invention provides for a "target nucleic acid" that is a polynucleotide which comprises, in 3' to 5' order, a first region that is at least partially complementary to a first oligonucleotide, an extension region and a second region that is at least partially complementary to a second oligonucleotide. The target nucleic acid may comprise single or double-stranded DNA or RNA.

The invention also provides for a "target nucleic acid" that is a polynucleotide which comprises in 3' to 5' order a first region that is at least partially complementary to a first oligonucleotide and a second region that is at least partially complementary to a second oligonucleotide.

A target nucleic acid according to the invention comprises a "first region" that is a length of nucleotides sufficient to permit hybridization of a first oligonucleotide as defined herein, wherein the "first region" is at least partially complementary to the first oligonucleotide. A "first region" is in the range of about 6 nucleotides to about 1000 nucleotides in length, with a preferred range of about 8-30 nucleotides, and optimally, a range of 10-25 nucleotides.

In some embodiments, a target nucleic acid according to the invention also comprises an "extension region" that is a length of nucleotides sufficient to permit extension of an oligonucleotide (e.g., a first oligonucleotide) via a nucleic acid polymerization activity. An "extension region" is in the range of about 1 nucleotide to about 1000 nucleotides in length, with a preferred range of about 3-100 nucleotides, and optimally, a range of 3-30 nucleotides in length.

The second region of a target nucleic acid is a length of nucleotides that is at least partially complementary to a probe (e.g., a second oligonucleotide, defined herein). A "second region" is in the range of about 6 nucleotides to about 1000 nucleotides in length, with a preferred range of about 8-30 nucleotides, and optimally, a range of 10-25 nucleotides.

E. Template Nucleic Acid

The invention also provides for a "template nucleic acid" that is a polynucleotide which comprises, in 3' to 5' order, a first region that is at least partially complementary to a released flap of a second oligonucleotide, defined herein, an extension region and a second region that is at least partially complementary to a probe (e.g., a third oligonucleotide, as defined herein).

The invention also provides for a "template nucleic acid" that is a polynucleotide which comprises in 3' to 5' order a first region that is at least partially complementary to a released flap of a second oligonucleotide and a second region that is at least partially complementary to a probe (e.g., a third oligonucleotide, as defined herein). The template nucleic acid may comprise single or double-stranded DNA or RNA.

A template nucleic acid according to the invention comprises a "first region" that is a length of nucleotides sufficient to permit hybridization of the released flap of a second oligonucleotide as defined herein, wherein the "first region" is at least partially complementary to the released flap of a second oligonucleotide. A "first region" is in the range of about 6 nucleotides to about 1000 nucleotides in length, with a preferred range of about 8-30 nucleotides, and optimally, a range of 10-25 nucleotides.

In some embodiments, the template nucleic acid according to the invention also comprises an "extension region" that is a length of nucleotides sufficient to permit extension of an oligonucleotide (e.g., the released flap of a second oligonucleotide as defined herein) via a nucleic acid polymerization activity. An "extension region" is in the range of about 1 nucleotide to about 1000 nucleotides in length, with a preferred range of about 3-100 nucleotides, and optimally, a range of 3-30 nucleotides in length.

The second region of a template nucleic acid is a length of nucleotides that is at least partially complementary to a probe (e.g., a third oligonucleotide, defined herein). A "second region" is in the range of about 6 nucleotides to about 1000 nucleotides in length, with a preferred range of about 8-30 nucleotides, and optimally, a range of 10-25 nucleotides.

F. Hybridization

Primers and probes according to the invention (e.g., first, second, and third oligonucleotides or forward and reverse primers) can be labeled and can be used to prepare a labeled cleavage structure. The following combinations of oligonucleotides can be annealed to sequences within a target nucleic acid sequence: a second oligonucleotide and first oligonucleotide or a forward primer and a second oligonucleotide. The following combinations of oligonucleotides can be annealed to sequences within a template nucleic acid: a third oligonucleotide and the released flap of a second oligonucleotide.

In one embodiment, a hybridized first oligonucleotide and second oligonucleotide form a cleavage structure and the cleavage structure is cleaved by a cleavage agent, according to the invention, to release a flap of the second oligonucleotide. In another embodiment, a hybridized released flap of the second oligonucleotide and the third oligonucleotide form a cleavage structure and the cleavage structure is cleaved by a cleavage means, according to the invention, to release a flap of the third oligonucleotide. The first and second cleavage reactions may be non-invasive. In a non-invasive cleavage reaction, cleavage occurs at or upstream of the elbow of the third oligonucleotides. A pair of interactive labels are coupled to the third oligonucleotide such that a non-invasive cleavage (cleavage at or upstream of the elbow) separates the labels to produce a detectable signal.

In one embodiment, a hybridized forward primer is extended by polymerization to form a cleavage structure and the cleavage structure is cleaved by a cleavage agent, according to the invention, to release a flap of the second oligonucleotide. In another embodiment, a hybridized released flap of the second oligonucleotide and the third oligonucleotide form a cleavage structure and the cleavage structure is cleaved by a cleavage means, according to the invention, to release a flap of a third oligonucleotide. In the event the first or second cleavage reaction is invasive, cleavage will occur downstream of the elbow of the third oligonucleotide. Cleavage downstream of the elbow results in the release of a flap of the third oligonucleotide in which contains both members of a pair of interactive labels. Therefore no detectable signal is produced.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch at the binding site of an oligonucleotide, as defined herein, is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

Numerous factors influence the efficiency and selectivity of hybridization of an oligonucleotide to a second nucleic acid molecule. These factors, which include oligonucleotide length, nucleotide sequence and/or composition, hybridization temperature, buffer composition and potential for steric hindrance in the region to which the oligonucleotide is required to hybridize, will be considered when designing oligonucleotides according to the invention.

A positive correlation exists between oligonucleotide length and both the efficiency and accuracy with which an oligonucleotide will anneal to a target sequence. In particular, longer sequences have a higher melting temperature ($T_M$) than do shorter ones, and are less likely to be repeated within a given target sequence, thereby minimizing promiscuous hybridization. Oligonucleotide sequences with a high G—C content or that comprise palindromic sequences tend to self-hybridize, as do their intended target sites, since unimolecular, rather than bimolecular, hybridization kinetics are generally favored in solution. However, it is also important to design an oligonucleotide that contains sufficient numbers of G—C nucleotide pairings since each G—C pair is bound by three hydrogen bonds, rather than the two that are found when A and T bases pair to bind the target sequence, and therefore forms a tighter, stronger bond. Hybridization temperature varies inversely with oligonucleotide annealing efficiency, as does the concentration of organic solvents, e.g., formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. As herein used, the term "standard stringent conditions" means hybridization will occur only if there is at least 95% and preferably at least 97% identity between the sequences. The sequences hybridize under stringent conditions following incubation of the sequences overnight at 42° C., followed by stringent washes (0.2×SSC at 65° C.). Certain embodiments, for example wherein an allele discriminating probe is used to discriminate against sequences that vary, for example by at least one nucleotide, may require higher hybridization temperatures for specific hybridization. As several factors affect the stringency of hybridization, the combination of parameters is more important than the absolute measure of a single factor.

G. Production of a Nucleic Acid

The invention provides nucleic acids to be detected and or measured, for amplification of a target nucleic acid sequence and for formation of a cleavage structure.

The present invention utilizes nucleic acids comprising RNA, cDNA, genomic DNA, synthetic forms, and mixed polymers. The invention includes both sense and antisense strands of a nucleic acid. According to the invention, the nucleic acid may be chemically or biochemically modified or may contain non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

1. Nucleic Acids Comprising DNA a. Cloning

Nucleic acids comprising DNA can be isolated from cDNA or genomic libraries by cloning methods well known to those skilled in the art (Ausubel et al., supra). Briefly, isolation of a DNA clone comprising a particular nucleic acid sequence involves screening a recombinant DNA or cDNA library and identifying the clone containing the desired sequence. Cloning will involve the following steps. The clones of a particular library are spread onto plates, transferred to an appropriate substrate for screening, denatured, and probed for the presence of a particular nucleic acid. A description of hybridization conditions, and methods for producing labeled probes is included below.

The desired clone is preferably identified by hybridization to a nucleic acid probe or by expression of a protein that can be detected by an antibody. Alternatively, the desired clone is identified by polymerase chain amplification of a sequence defined by a particular set of primers according to the methods described below.

The selection of an appropriate library involves identifying tissues or cell lines that are an abundant source of the desired sequence. Furthermore, if a nucleic acid of interest contains regulatory sequence or intronic sequence a genomic library is screened (Ausubel et al., supra).

b. Genomic DNA

Nucleic acid sequences of the invention may be amplified from genomic DNA. Genomic DNA is isolated from tissues or cells according to the following method.

To facilitate detection of a variant form of a gene from a particular tissue, the tissue is isolated free from surrounding normal tissues. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 µg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used for PCR analysis, according to the invention.

c. Restriction Digest (of cDNA or Genomic DNA)

Following the identification of a desired cDNA or genomic clone containing a particular target nucleic acid sequence, nucleic acids of the invention may be isolated from these clones by digestion with restriction enzymes.

The technique of restriction enzyme digestion is well known to those skilled in the art (Ausubel et al., supra). Reagents useful for restriction enzyme digestion are readily available from commercial vendors including Stratagene, as well as other sources.

d. PCR

Nucleic acids of the invention may be amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a target nucleic acid sequence to be amplified, two single stranded oligonucleotide primers flanking the sequence to be amplified, a DNA polymerase, deoxyribonucleoside triphosphates, a buffer and salts.

PCR, is performed as described in Mullis and Faloona, 1987, Methods Enzymol., 155: 335, herein incorporated by reference.

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science* 230:1350.

PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of a suitable buffer, 0.4 µl of 1.25 µM dNTP, 2.5 units of Taq DNA polymerase (Stratagene) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Detection methods generally employed in standard PCR techniques use a labeled probe with the amplified DNA in a hybridization assay. Preferably, the probe is labeled, e.g., with $^{32}$P, biotin, horseradish peroxidase (HRP), etc., to allow for detection of hybridization.

Other means of detection include the use of fragment length polymorphism (PCR FLP), hybridization to allele-specific oligonucleotide (ASO) probes (Saiki et al., 1986, *Nature* 324:163), or direct sequencing via the dideoxy method (using amplified DNA rather than cloned DNA). The standard PCR technique operates (essentially) by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, terramethylbenzidine (TMB) and hydrogen peroxide are added: HRP oxidizes the hydrogen peroxide, which in turn oxidizes the TMB to a blue precipitate, indicating a hybridized probe.

2. Nucleic Acids Comprising RNA

The present invention also provides a nucleic acid comprising RNA.

Nucleic acids comprising RNA can be purified according to methods well known in the art (Ausubel et al., supra). Total RNA can be isolated from cells and tissues according to methods well known in the art (Ausubel et al., supra) and described below.

RNA is purified from mammalian tissue according to the following method. Following removal of the tissue of interest, pieces of tissue of $\leq 2$ g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-HCl, pH 7.5 (0.05 M final) and 20 ml $Na_2$EDTA (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from mammalian tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 µl DEPC-treated water or DEPC-treated 0.5% SDS (Chomczynski and Sacchi, 1987, *Anal. Biochem.*, 162: 156).

Nucleic acids comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM $MgCl_2$, 10 mM spermidine, 250 NaCl [T7 or T3] or 200 mM Tris-HCl, pH 7.5, 30 mM $MgCl_2$, 10 mM spermidine [SP6]), dithiothreitol, RNase inhibitors, each of the four ribonucleoside triphosphates, and either SP6, T7 or T3 RNA polymerase for 30 min at 37° C. To prepare a radiolabeled polynucleotide comprising RNA, unlabeled UTP will be omitted and $^{35}S$-UTP will be included in the reaction mixture. The DNA template is then removed by incubation with DNaseI. Following ethanol precipitation, an aliquot of the radiolabeled RNA is counted in a scintillation counter to determine the cpm/µl (Ausubel et al., supra).

Alternatively, nucleic acids comprising RNA are prepared by chemical synthesis techniques such as solid phase phosphoramidite (described above).

3. Nucleic Acids Comprising Oligonucleotides

A nucleic acid comprising oligonucleotides can be made by using oligonucleotide synthesizing machines which are commercially available (described above).

It is well known by those with skill in the art that oligonucleotides can be synthesized with certain chemical and/or capture moieties, such that they can be coupled to solid supports and bind to a binding moiety or a tag. Suitable capture elements include, but are not limited to a nucleic acid binding protein or a nucleotide sequence, biotin, a hapten, a protein, or a chemically reactive moiety. Such oligonucleotides may either be used first in solution, and then captured onto a solid support, or first attached to a solid support and then used in a detection reaction. An example of the latter would be to couple a upstream probe molecule to a solid support, such that the 5' end of the upstream probe molecule comprised a fluorescent quencher. The same upstream probe molecule would also comprise a fluorophore in a location such that a FEN nuclease cleavage would physically separate the quencher from the fluorophore. For example, the target nucleic acid could hybridize with the solid-phase upstream probe oligonucleotide, and a liquid phase upstream primer could also hybridize with the target molecule, such that a FEN cleavage reaction occurs on the solid support and liberates the 5' quencher moiety from the complex. This would cause the solid support-bound fluorophore to be detectable, and thus reveal the presence of a cleavage event upon a suitably labeled or identified solid support. Different upstream probe molecules could be bound to different locations on an array. The location on the array would identify the probe molecule, and indicate the presence of the template to which the probe molecule can hybridize.

II. Duplexes

The invention provides for duplexes that are used to prepare cleavage structures according to the invention.

A duplex, according to the invention, is formed by mixing, in any order, the components of the duplex, under conditions that permit hybridization of the components of the duplex and formation of the duplex. In one embodiment, the duplex is formed by first hybridizing the target nucleic acid or the template nucleic acid with the downstream oligonucleotide, and then adding the upstream oligonucleotide. In another embodiment, the duplex is formed by hybridizing the target nucleic acid and/or template nucleic acid simultaneously with the downstream oligonucleotide and upstream oligonucleotide. In one embodiment, the duplex is formed during an annealing step of a thermal cycling reaction. Hybridization of a target or template nucleic acid with one or more oligonucleotides is performed under suitable conditions. Suitable conditions include, for example, a temperature that permits denaturation of a probe comprising a secondary structure and the formation of hydrogen bonds between complementary bases of the target or template nucleic acid and the probe or probes. In certain embodiments, a suitable amount of a denaturing agent, such as dimethylsulfoxide (DMSO) or glycerol is added to the hybridization mixture. A suitable amount of a denaturing agent is sufficient to permit hybridization and formation of a first or second duplex, according to the invention, as well as steps of polymerization and/or cleavage, described below. A concentration of a denaturing agent that is useful according to the invention will vary depending on the base pair compositions of the components of the duplex. A concentration of a denaturing agent that is useful according to the invention will be determined experimentally by methods known in the art and described herein, to be sufficient to permit hybridization of complementary nucleic acids, polymerization of a primer (e.g., forward and reverse primer) and cleavage of a cleavage structure. In one embodiment, the denaturing agent is DMSO, used at concentration of 0 to 6%, and preferably around 1.5 to 2% for nucleic acids in the range of approximately 0.1 to 1 kb. A concentration of DMSO greater than 2% may be used for nucleic acids greater than 10 kb. Alternatively, glycerol can be used as a denaturing agent at a concentration of from 0 to 10%, and preferably 5 to 8%. Both, or even other denaturing agents, may be used in combination at concentrations that are determined experimentally by methods known in the art.

Methods of determining "conditions that permit hybridization" of components of a duplex are known in the art, and parameters that influence nucleic acid hybridization are discussed in detail in the section entitled "Nucleic Acids".

A. First Duplex

In one embodiment, the invention provides for a first duplex comprising a target nucleic acid (e.g., A'C', FIG. 1), an upstream oligonucleotide (first oligonucleotide) with a 3' terminal nucleotide that is non-complementary to the target (e.g., A-1 of FIG. 1) and a downstream oligonucleotide (e.g., a second oligonucleotide, e.g., FC, FIG. 1). The downstream oligonucleotide (e.g., a second oligonucleotide) has a 5' region that is non-complementary to the target nucleic acid and a 3' region which is complementary to the target. According to this embodiment, the most 3' complementary nucleotide of the first oligonucleotide and most 5' complementary nucleotide of the second oligonucleotide are separated by at least a nick when annealed to the target. The first duplex forms the first cleavage structure.

In another embodiment, the invention provides for a first duplex comprising a target nucleic acid (e.g., A'C', FIG. 1), a forward primer that is complementary to a first region of the target (e.g., A-2 of FIG. 1) and a downstream oligonucleotide (e.g., a second oligonucleotide, e.g., FC, FIG. 1). The downstream oligonucleotide (e.g., a second oligonucleotide) has a 5' region that is non-complementary to the target nucleic acid and a 3' region which is complementary to a second region of the target. The first duplex forms the first cleavage structure.

In one embodiment, a duplex is formed by first hybridizing the target nucleic acid with the second oligonucleotide and then adding the first oligonucleotide.

In another embodiment, a duplex is formed by simultaneously hybridizing the target nucleic acid with the upstream and downstream oligonucleotides.

In one embodiment, the first and second oligonucleotides are separated by a nick when annealed to the target.

In another embodiment, the first and second oligonucleotides are separated by a 1 nucleotide gap when annealed to the target.

In another embodiment, the first and second oligonucleotides are separated by a 2 nucleotide gap when annealed to the target.

In yet a further embodiment, the first and second oligonucleotides are separated by a 3 nucleotide gap when annealed to the target.

B. Second Duplex

The invention provides for a second duplex comprising a template nucleic acid (e.g., F'H', FIG. 1), an upstream oligonucleotide (e.g., the released flap of a second oligonucleotide, e.g., F, FIG. 1) and a downstream oligonucleotide (e.g., a third oligonucleotide, e.g., F2H, FIG. 1). The third oligonucleotide has a 5' region that is non-complementary to the template nucleic acid and a 3' region that is complementary to a second region of the template. According to this embodiment, the upstream oligonucleotide (e.g., the released flap of a second oligonucleotide) and downstream oligonucleotide (e.g., a third oligonucleotide) hybridize to the template such that the most 3' complementary nucleotide of the released flap and most 5' complementary nucleotide of the third oligonucleotide are separated by at least a nick when annealed to the target.

In one embodiment, the released flap and the third oligonucleotides are separated by a nick when annealed to the template nucleic acid.

In another embodiment, the released flap and third oligonucleotide are separated by a 1 nucleotide gap when annealed to the template nucleic acid.

In a further embodiment, the said released flap and third oligonucleotide are separated by a 2 nucleotide gap when annealed to the target.

In yet a further embodiment, the released flap and third oligonucleotide are separated by a 3 nucleotide gap when annealed to the target.

III. Nucleic Acid Polymerization Activities

The invention provides for nucleic acid polymerization activities (including nucleic acid polymerases) that are useful in an isothermal reaction. A nucleic acid polymerization activity that is useful in an isothermal reaction according to the invention includes, but is not limited to any of the nucleic acid polymerases listed below.

A nucleic acid polymerase according to the invention can be thermostable. As used herein, "thermostable" refers to an enzyme which is stable and active at temperatures as great as preferably between about 90-100° C. and more preferably between about 70-98° C. to heat as compared, for example, to a non-thermostable form of an enzyme with a similar activity. For example, a thermostable nucleic acid polymerase or FEN nuclease derived from thermophilic organisms such as *P.*

*furiosus, M jannaschii, A. fulgidus* or *P. horikoshii* are more stable and active at elevated temperatures as compared to a nucleic acid polymerase from *E. coli* or a mammalian FEN enzyme. A representative thermostable nucleic acid polymerase isolated from *Thermus aquaticus* (Taq) is described in U.S. Pat. No. 4,889,818 and a method for using it in conventional PCR is described in Saiki et al., 1988, *Science* 239:487. Another representative thermostable nucleic acid polymerase isolated from *P. furiosus* (Pfu) is described in Lundberg et al., 1991, *Gene*, 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus*.

Temperature stable polymerases and FEN nucleases are preferred in a thermocycling process wherein double stranded nucleic acids are denatured by exposure to a high temperature (about 950 C) during the PCR cycle.

Known DNA polymerases useful according to the invention include, for example, *E. coli* DNA polymerase I, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

Nucleic acid polymerases substantially lacking 5' to 3' exonuclease activity useful according to the invention include but are not limited to Klenow and Klenow exo–, and T7 DNA polymerase (Sequenase).

Thermostable nucleic acid polymerases substantially lacking 5' to 3' exonuclease activity useful according to the invention include but are not limited to Pfu, exo– Pfu (a mutant form of Pfu that lacks 3' to 5' exonuclease activity), the Stoffel fragment of Taq, N-truncated Bst, N-truncated Bca, Genta, JdF3 exo–, Vent, Vent exo– (a mutant form of Vent that lacks 3' to 5' exonuclease activity), Deep Vent, Deep Vent exo– (a mutant form of Deep Vent that lacks 3' to 5' exonuclease activity), U1Tma, and ThermoSequenase.

Nucleic acid polymerases useful in certain embodiments of the invention substantially lack 3' to 5' exonuclease activity and include but are not limited to exo– Pfu DNA polymerase (a mutant form of Pfu DNA polymerase that substantially lacks 3' to 5' exonuclease activity, Cline et al., 1996, Nucleic Acids Research, 24: 3546; U.S. Pat. No. 5,556,772; commercially available from Stratagene, La Jolla, Calif. Catalogue #600163), exo– Tma DNA polymerase (a mutant form of Tma DNA polymerase that substantially lacks 3' to 5' exonuclease activity), exo– Tli DNA polymerase (a mutant form of Tli DNA polymerase that substantially lacks 3' to 5' exonuclease activity New England Biolabs, (Cat #257)), exo– *E. coli* DNA polymerase (a mutant form of *E. coli* DNA polymerase that substantially lacks 3' to 5' exonuclease activity) exo– Klenow fragment of *E. coli* DNA polymerase I (Stratagene, Cat #600069), exo– T7 DNA polymerase (a mutant form of T7 DNA polymerase that substantially lacks 3' to 5' exonuclease activity), exo– KOD DNA polymerase (a mutant form of KOD DNA polymerase that substantially lacks 3' to 5' exonuclease activity), exo– JDF-3 DNA polymerase (a mutant form of JDF-3 DNA polymerase that substantially lacks 3' to 5' exonuclease activity), exo– PGB-D DNA polymerase (a mutant form of PGB-D DNA polymerase that substantially lacks 3' to 5' exonuclease activity) New England Biolabs, Cat. #259, Tth DNA polymerase, Taq DNA polymerase (e.g., Cat. Nos. 600131, 600132, 600139, Stratagene); U1Tma (N-truncated) *Thermatoga martima* DNA polymerase; Klenow fragment of DNA polymerase I, 9°Nm DNA polymerase (discontinued product from New England Biolabs, Beverly, Mass.), "3'-5' exo reduced" mutant (Southworth et al., 1996, Proc. Natl. Acad. Sci. 93:5281) and Sequenase (USB, Cleveland, Ohio). The polymerase activity of any of the above enzyme can be defined by means well known in the art. One unit of DNA polymerase activity, according to the subject invention, is defined as the amount of enzyme which catalyzes the incorporation of 10 nmoles of total dNTPs into polymeric form in 30 minutes at optimal temperature.

Nucleic acid polymerases useful according to the invention include both native polymerases as well as polymerase mutants, which lack 5' to 3' exonuclease activity. Nucleic acid polymerases useful according to the invention can possess different degrees of thermostability.

The polymerization agent is a polymerase. In one embodiment, the polymerization agent lacks 5' to 3' exonuclease activity. In another embodiment, the polymerization agent is thermostable. In yet another embodiment, a signal enzyme contains polymerization activity and cleavage activity. Enzymes having both activities include: E. coli DNA polymerase I, T7 DNA polymerase, Tth DNA polymerase, or Taq DNA polymerase. In an alternative embodiment the cleavage activity and the polymerization activity are provided by separate enzymes. The separate enzymes may be supplied in a single formulation.

Additional nucleic acid polymerases substantially lacking 5' to 3' exonuclease activity with different degrees of thermostability useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻ T7 "Sequenase" DNA polymerase).

B. Archaeal DNA Polymerases:

There are 2 different classes of DNA polymerases which have been identified in archaea: 1. Family B/pol α type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol α or pol II) can be derived from archaea with optimal growth temperatures that are similar to the desired assay temperatures. Examples of suitable archaea include, but are not limited to:

1. Thermolabile (useful for 37° C. assays)—e.g., *Methanococcus voltae*

2. Thermostable (useful for non-PCR assays)—e.g., *Sulfolobus solfataricus, Sulfolobus acidocaldarium, Methanococcus jannaschi, Thermoplasma acidophilum*. It is estimated that suitable archaea exhibit maximal growth temperatures of ≦80-85° C. or optimal growth temperatures of ≦70-80° C.

3. Thermostable (useful for PCR assays)—e.g., *Pyrococcus* species (*furiosus*, species GB-D, species strain KOD1, *woesii, abysii, horikoshii*), *Thermococcus* species (*litoralis*, species 9° North-7, species JDF-3, *gorgonarius*), *Pyrodictium occultum*, and *Archaeoglobus fulgidus*. It is estimated that suitable archaea would exhibit maximal growth temperatures of ≧80-85° C. or optimal growth temperatures of ≧70-80° C. Appropriate PCR enzymes from the archaeal pol α DNA polymerase group are commercially available, including KOD (Toyobo), Pfx (Life Technologies, Inc.), Vent (New England BioLabs), Deep Vent (New England BioLabs), and Pwo (Boehringer-Mannheim).

Additional archaea related to those listed above are described in the following references: *Archaea: A Laboratory Manual* (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases.

There are a variety of commercially available Pol I DNA polymerases, some of which have been modified to reduce or abolish 5' to 3' exonuclease activity. Methods used to eliminate 5' to 3' exonuclease activity of pol I DNA polymerases include:

mutagenesis (as described in Xu et al., 1997, *J. Mol. Biol.*, 268:284 and Kim et al., 1997, *Mol. Cells*, 7:468).

N-truncation by proteolytic digestion (as described in Klenow et al., 1971, *Eur. J. Biochem.*, 22: 371), or N-truncation by cloning and expressing as C-terminal fragments (as described in Lawyer et al., 1993, *PCR Methods Appl.*, 2:275).

As for archaeal sources, the assay-temperature requirements determine which eubacteria should be used as a source of a DNA polymerase useful according to the invention (e.g., mesophiles, thermophiles, hyperthermophiles).

1. Mesophilic/Thermolabile (Useful for 37° C. Assays)

i. DNA polymerases naturally substantially lacking 5' to 3' exonuclease activity: pol II or the pol III catalytic subunit from mesophilic eubacteria, such as *Escherchia coli, Streptococcus pneumoniae, Haemophilus influenza, Mycobacterium* species (*tuberculosis, leprae* ii. DNA polymerase mutants substantially lacking 5' to 3' exonuclease activity: Pol I DNA polymerases for N-truncation or mutagenesis can be isolated from the mesophilic eubacteria listed above (Ci). A commercially-available eubacterial DNA polymerase pol I fragment is the Klenow fragment (N-truncated *E. coli* pol I; Stratagene).

2. Thermostable (Useful for Non PCR Assays)

i. DNA polymerases naturally substantially lacking 5' to 3' exonuclease activity: Pol II or the pol III catalytic subunit from thermophilic eubacteria, such as *Bacillus* species (e.g., *stearothermophilus, caldotenax, caldovelox*)

ii. DNA polymerase mutants substantially lacking 5' to 3' exonuclease activity: Suitable pol I DNA polymerases for N-truncation or mutagenesis can be isolated from thermophilic eubacteria such as the *Bacillus* species listed above. Thermostable N-truncated fragments of *B. stearothermophilus* DNA polymerase pol I are commercially available and sold under the trade names Bst DNA polymerase I large fragment (Bio-Rad and Isotherm DNA polymerase (Epicentre)). A C-terminal fragment of *Bacillus caldotenax* pol I is available from Panvera (sold under the tradename Ladderman).

3. Thermostable (Useful for PCR Assays)

i. DNA polymerases naturally substantially lacking 5' to 3' exonuclease activity: Pol II or pol III catalytic subunit from *Thermus* species (*aquaticus, thermophilus, flavus, ruber, caldophilus, filiformis, brokianus*) or from *Thermotoga maritima*. The catalytic pol III subunits from *Thermus thermophilus* and *Thermus aquaticus* are described in Yi-Ping et al., 1999, J. Mol. Evol., 48:756 and McHenry et al., 1997, J. Mol. Biol., 272:178.

ii. DNA polymerase mutants substantially lacking 5' to 3' exonuclease activity: Suitable pol I DNA polymerases for N-truncation or mutagenesis can be isolated from a variety of thermophilic eubacteria, including *Thermus* species and *Thermotoga maritima* (see above). Thermostable fragments of *Thermus aquaticus* DNA polymerase pol I (Taq) are commercially available and sold under the trade names KlenTaq1 (Ab Peptides), Stoffel fragment (Perkin-Elmer), and ThermoSequenase (Amersham). In addition to C-terminal fragments, 5' to 3' exonuclease⁻ Taq mutants are also commercially available, such as TaqFS (Hoffman-LaRoche). In addition to 5'-3' exonuclease⁻ versions of Taq, an N-truncated version of *Thermotoga maritima* DNA polymerase I is also commercially available (tradename U1Tma, Perkin-Elmer).

Additional eubacteria related to those listed above are described in *Thermophilic Bacteria* (Kristjansson, J. K., ed.) CRC Press, Inc., Boca Raton, Fla., 1992.

D. Eukaryotic 5' to 3' Exonuclease⁻ DNA Polymerases (Useful for 37° C. Assays)

There are several DNA polymerases that have been identified in eukaryotes, including DNA pol α (replication/repair), δ (replication), ε (replication), β (repair) and γ (mitochondrial replication). Eukaryotic DNA polymerases are devoid of 5' to 3' exonuclease activity, as this activity is encoded by a separate polypeptide (e.g., mammalian FEN-1 or yeast RAD2). Suitable thermolabile DNA polymerases may be isolated from a variety of eukaryotes (including but not limited to yeast, mammalian cells, insect cells, *Drosophila*) and eukaryotic viruses (e.g., EBV, adenovirus).

It is possible that DNA polymerase mutants lacking 3'-5' exonuclease (proofreading) activity, in addition to lacking 5' to 3' exonuclease activity, could exhibit improved performance in FEN-based detection strategies. For example, reducing or abolishing inherent 3' to 5' exonuclease activity may lower background signals by diminishing non-specific exonucleolytic degradation of labeled probes. Three 3' to 5' exonuclease motifs have been identified, and mutations in these regions have been shown to abolish 3' to 5' exonuclease activity in Klenow, φ29, T4, T7, and Vent DNA polymerases, yeast Pol α, Pol β, and Pol γ, and *Bacillus subtilis* Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo⁻ T7; USB), Pfu exo⁻ (Stratagene), exo⁻ Vent (New England BioLabs), exo⁻ DeepVent (New England BioLabs), exo⁻ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche).

Nucleic acid polymerases with strand displacement activity are also useful according to the invention.

If polymerases other than Pfu are used, buffers and extension temperatures are selected to allow for optimal activity by the particular polymerase useful according to the invention. Buffers and extension temperatures useful for polymerases according to the invention are know in the art and can also be determined from the Vendor's specifications.

Additional nucleases useful according to the invention include a mutant form of Taq polymerase that lacks a 5' to 3' exonuclease activity but that possesses a 3' to 5' DNA synthetic activity comprises the following mutation: D144S/F667Y Taq wherein D144S eliminates 5' to 3' exonuclease activity and F667Y improves ddNTP incorporation.

Exo– mutants of PolII polymerase can be prepared according to the method of Xu et al., 1997, *J. Mol. Biol.*, 268: 284.

IV. Cleavage Structure

The invention provides for a cleavage structure that can be cleaved by a nuclease (e.g., a FEN nuclease) and therefore teaches methods of preparing a cleavage structure.

A. Preparation of a Cleavage Structure

1. In one embodiment of the invention, a first cleavage structure is formed by incubating a target nucleic acid (A'C', FIG. 1), a downstream probe (e.g., a second oligonucleotide, e.g., FC, FIG. 1), and an upstream oligonucleotide (e.g., a first oligonucleotide, e.g., A-1, FIG. 2), with a suitable buffer (example 1× Pfu buffer available from Stratagene (Catalog #600153) or probe buffer with 15 mM of Tris-HCL (pH8), 50 mM KCL, 5.5 mM $MgCl_2$, 8% glycerol, 1% DMSO) under conditions that allow the target nucleic acid sequence to hybridize to the oligonucleotides (for example 95° C. for 10 sec-5 minutes followed by cooling to between approximately 50-60° C.) to form a duplex according to the invention. The 5' region of the probe is non-complementary to the target and forms a 5' flap when annealed to the target. The 3' terminal nucleotide of the upstream oligonucleotide is non-complementary to the target. The cleavage structure is formed when the complementary portion of the upstream oligonucleotide and the complementary portion of the downstream oligonucleotide anneal to the target so that they are separated by at least a nick. The optimal temperature for formation and cleavage of the structure will vary depending on the specific oligonucleotides and polymerases. The reaction may include a forward and reverse primer and be performed under PCR reaction conditions. For example, a cleavage structure of the invention can be formed under the following reaction conditions: (1) 2 min at 95° C. for 1 cycle, (2) 95° C. for 1 second, (3) 60° C. for 18 seconds. Steps (2) and (3) may be cycled.

2. In another embodiment of the invention, a second cleavage structure is formed by incubating a template nucleic acid (F'H', FIG. 1), a downstream probe (e.g., a third oligonucleotide, e.g., F2H, FIG. 1), and an upstream oligonucleotide (e.g., the released flap of a second oligonucleotide, e.g., F, FIG. 1), with a suitable buffer (1× Pfu buffer available from Stratagene (Catalog #600153) or probe buffer with 15 mM of Tris-HCL (pH8), 50 mM KCL, 5.5 mM $MgCl_2$, 8% glycerol, 1% DMSO) under conditions that allow the template nucleic acid sequence to hybridize to the oligonucleotides (for example 95° C. for 10 sec-5 minutes followed by cooling to between approximately 50-60° C.) to form a second duplex according to the invention. The 5' region of the probe is non-complementary to the template and forms a 5' flap when the 3' region of the oligonucleotide is annealed to the template. The 3' terminal nucleotide of the upstream oligonucleotide is non-complementary to the template. The cleavage structure is formed when the template complementary portion of the upstream oligonucleotide and the complementary portion of the downstream oligonucleotide anneal to the template so that they are separated by at least a nick. The optimal temperature for formation and cleavage of the structure will vary depending on the specific oligonucleotides and polymerases. The reaction may include a forward and reverse primer and be performed under PCR reaction conditions. For example, a cleavage structure of the invention can be formed under the following reaction conditions: 2 min at 95° C. for 1 cycle, (2) 95° C. for 1 second, (3) 60° C. for 18 seconds. Steps (2) and (3) may be cycled.

A cleavage structure as described in any one of parts 1-2, above can also be prepared as follows. The components of a cleavage structure are hybridized at a temperature (for example 50° C., 69° C., or 72° C.), that is optimal for hybridization, and subsequent steps of cleavage and in some embodiments polymerization. The components of a cleavage structure are hybridized for a time sufficient to permit hybridization and formation of a first duplex, or a second duplex, as defined herein.

In certain embodiments of the invention, a first or second duplex is formed by incubating the components of a first or second duplex in the presence of a denaturing agent (e.g., DMSO or glycerol) at a concentration that is sufficient to permit hybridization and formation of a first or second duplex, according to the invention, as well as subsequent steps of cleavage and in some embodiments polymerization, described below. A concentration of a denaturing agent that is useful according to the invention will vary depending on the base pair compositions of the components of the duplex. A concentration of a denaturing agent that is useful according to the invention will be determined experimentally by methods known in the art and described herein, to be sufficient to permit hybridization of complementary nucleic acids, cleavage of a cleavage structure and in some embodiments polymerization of a primer (e.g., forward primer), according to the invention. In one embodiment, the denaturing agent is DMSO, used at concentration of 0 to 6%, and preferably around 1.5 to 2% for nucleic acids in the range of approximately 0.1 to 1 kb. A concentration of DMSO greater than 2% may be used for nucleic acids greater than 10 kb. Alternatively, glycerol can be used as a denaturing agent at a concentration of from 0 to 10%, and preferably 5 to 8%. Both, or even other denaturing agents, may be used in combination at concentrations that are determined experimentally by methods known in the art.

For an isothermal reaction according to the invention, all of the steps of the reaction that occur after the formation of a first duplex, as defined herein, are performed at the same temperature.

A probe having a secondary structure that changes upon binding of the probe to the target nucleic acid sequence may be used to prepare a cleavage structure according to the invention.

B. How to Prepare a Labeled Cleavage Structure

The invention provides for labeled cleavage structures. A labeled cleavage structure is formed as described in section A1-A2 of the section entitled "Cleavage Structure", above, wherein one or both of the downstream oligonucleotides is labeled (e.g., with first member of a pair of interacting moieties on the 5' flap and a second member of the pair of interacting moieties on 3' region of the second or third oligonucleotide) such that cleavage of the non-invasive cleavage structure produces a detectable signal. Methods of labeling a nucleic acid probe or oligonucleotide are well known in the art (See, Sambrook et al., supra; Ausubel et al., supra).

The oligonucleotide probe may be labeled, as described below, by incorporating moieties detectable by spectroscopic, photochemical, biochemical, immunochemical, enzymatic or chemical means. The method of linking or conjugating the label to the oligonucleotide probe depends, of course, on the type of label(s) used and the position of the label on the probe. In some embodiments the third oligonucleotide is labeled with a pair of interactive moieties. A first member of the pair of interactive moieties is operatively coupled to the 5' flap and a second member of the pair of interacting moieties is operatively coupled to the +1 nucleotide a probe.

A variety of labels that would be appropriate for use in the invention, as well as methods for their inclusion in the downstream oligonucleotide, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

1. Fluorophores

Fluorophores for use as labels in constructing labeled probes of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

Probes labeled with fluorophores can readily be used in nuclease (e.g. FEN-nuclease) mediated cleavage of a cleavage structure comprising a labeled probe according to the invention. If the label is on the 5'-end of the probe, the nuclease (e.g. FEN-nuclease) generated labeled fragment is separated from the intact, hybridized probe by procedures well known in the art. In another embodiment of the invention, detection of the hydrolyzed, labeled probe can be accomplished using, for example, fluorescence polarization, a technique to differentiate between large and small molecules based on molecular tumbling. Large molecules (i.e., intact labeled probe) tumble in solution much more slowly than small molecules. Upon linkage of a fluorescent moiety to an appropriate site on the molecule of interest (e.g., the 5' end of a labeled probe), this fluorescent moiety can be measured (and differentiated) based on molecular tumbling, thus differentiating between intact and digested probe.

2. FRET

As used herein, the phrase "interactive pair of labels" as well as the phrase "pair of interactive labels" as well as the phrase "first and second moieties" refer to a pair of molecules which interact physically, optically, or otherwise in such a manner as to permit detection of their proximity by means of a detectable signal. Examples of a "pair of interactive labels" include, but are not limited to, labels suitable for use in fluorescence resonance energy transfer (FRET) (Stryer, L. Ann. Rev. Biochem. 47, 819-846, 1978), scintillation proximity assays (SPA) (Hart and Greenwald, Molecular Immunology 16:265-267, 1979; U.S. Pat. No. 4,658,649), luminescence resonance energy transfer (LRET) (Mathis, G. Clin. Chem. 41, 1391-1397, 1995), direct quenching (Tyagi et al., Nature Biotechnology 16, 49-53, 1998), chemiluminescence energy transfer (CRET) (Campbell, A. K., and Patel, A. Biochem. J. 216, 185-194, 1983), bioluminescence resonance energy transfer (BRET) (Xu, Y., Piston D. W., Johnson, Proc. Natl. Acad. Sc., 96, 151-156, 1999), or excimer formation (Lakowicz, J. R. Principles of Fluorescence Spectroscopy, Kluwer Academic/Plenum Press, New York, 1999).

The first and second moieties are "operatively coupled" to the oligonucleotides of the invention. This means that each moiety is coupled to its respective sequence in any manner consistent with its operation, i.e., in any manner consistent with providing a detectable signal upon cleavage of the probe. For example, the pair of moieties can be either covalently or non-covalently attached to the oligonucleotides of the invention. Examples of non-covalent attachment, any of which can be employed to operatively couple the first or second moiety to the oligonucleotides of the invention, include attachment via hybridization, hydrogen bonds, ionic bonds, hydrophobic interactions, van der Waals interactions, and protein-nucleic acid interactions. Preferred are moieties which are covalently attached at or near the 5' and 3' ends of the oligonucleotides.

As used herein, references to "fluorescence" or "fluorescent groups" or "fluorophores" include luminescence and luminescent groups, respectively.

An "increase in fluorescence", as used herein, refers to an increase in detectable fluorescence emitted by a fluorophore. An increase in fluorescence may result, for example, when the distance between a fluorophore and a quencher is increased, for example due to a cleavage reaction by a cleavage means, such that the quenching is reduced. There is an "increase in fluorescence" when the fluorescence emitted by the fluorophore is increased by at least 2 fold, for example 2, 2.5, 3, 4, 5, 6, 7, 8, 10 fold or more.

a. FRET Compatible Fluorophores

A pair of interactive labels useful for the invention can comprise a pair of FRET-compatible dyes, or a quencher-dye pair. In one embodiment, the pair comprises a fluorophore-quencher pair.

Oligonucleotides of the present invention permit detection/measurement of a target nucleic acid by fluorescence. They can be labeled with a fluorophore and quencher in such a manner that the fluorescence emitted by the fluorophore in intact oligonucleotides is substantially quenched, whereas the fluorescence in cleaved or in some embodiments target hybridized oligonucleotides are not quenched, resulting in an increase in overall fluorescence upon probe cleavage or in some embodiments target hybridization. Furthermore, the generation of a fluorescent signal during real-time detection of an amplification reaction product allows accurate quantitation of the initial number of target sequences in a sample.

A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloyl-fluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), Quasar-670 (Bioreseach Technologies), CalOrange (Bioresearch Technologies), Rox, as well as suitable derivatives thereof.

b. FRET Compatible Quenchers

As used herein, the term "quencher" refers to a chromophoric molecule or part of a compound, which is capable of reducing the emission from a fluorescent donor when attached to or in proximity to the donor. Quenching may occur by any of several mechanisms including fluorescence resonance energy transfer, photoinduced electron transfer, paramagnetic enhancement of intersystem crossing, Dexter exchange coupling, and exciton coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more.

The quencher can be any material that can quench at least one fluorescence emission from an excited fluorophore being used in the assay. There is a great deal of practical guidance available in the literature for selecting appropriate reporter-quencher pairs for particular probes, as exemplified by the following references: Clegg (1993, Proc. Natl. Acad. Sci., 90:2994-2998); Wu et al. (1994, Anal. Biochem., 218:1-13); Pesce et al., editors, Fluorescence Spectroscopy (1971, Marcel Dekker, New York); White et al., Fluorescence Analysis: A Practical Approach (1970, Marcel Dekker, New York); and the like. The literature also includes references providing exhaustive lists of fluorescent and chromogenic molecules and their relevant optical properties for choosing reporter-quencher pairs, e.g., Berlman, Handbook of Fluorescence Spectra of Aromatic Molecules, 2nd Edition (1971, Academic Press, New York); Griffiths, Colour and Constitution of Organic Molecules (1976, Academic Press, New York); Bishop, editor, Indicators (1972, Pergamon Press, Oxford); Haugland, Handbook of Fluorescent Probes and Research Chemicals (1992 Molecular Probes, Eugene) Pringsheim, Fluorescence and Phosphorescence (1949, Interscience Publishers, New York), all of which incorporated hereby by reference. Further, there is extensive guidance in the literature for derivatizing reporter and quencher molecules for covalent attachment via common reactive groups that can be added to an oligonucleotide, as exemplified by the following references, see, for example, Haugland (cited above); Ullman et al., U.S. Pat. No. 3,996,345; Khanna et al., U.S. Pat. No. 4,351,760, all of which hereby incorporated by reference.

A number of commercially available quenchers are known in the art, and include but are not limited to DABCYL, BHQ-1, BHQ-2, and BHQ-3. The BHQ ("Black Hole Quenchers") quenchers are a new class of dark quenchers that prevent fluorescence until a hybridization event occurs. In addition, these new quenchers have no native fluorescence, virtually eliminating background problems seen with other quenchers. BHQ quenchers can be used to quench almost all reporter dyes and are commercially available, for example, from Biosearch Technologies, Inc (Novato, Calif.).

c. Attachment of Fluorophore and Quencher

In one embodiment of the invention, one member of the pair of interactive labels is attached to the 5' region of the downstream oligonucleotide (e.g., second or third oligonucleotide) and the second member of the pair of interactive labels is attached to the 3' region of the downstream oligonucleotide (e.g., second or third oligonucleotide). In one embodiment of the invention, the fluorophore or quencher is attached to the 3' nucleotide of an oligonucleotide of the invention. In another embodiment of the invention, the fluorophore or quencher is attached to the 5' nucleotide. In yet another embodiment, the fluorophore or quencher is internally attached to an oligonucleotide of the invention. In some embodiments, either the fluorophore or quencher is attached to the 5' nucleotide of the probe and the other of said fluorophore or quencher is attached to the 3' nucleotide of the probe. Attachment can be made via direct coupling, or alternatively using a spacer molecule of, for example, from about 1 to about 5 atoms in length.

For the internal attachment of the fluorophore or quencher, linkage can be made using any of the means known in the art. Appropriate linking methodologies for attachment of many dyes to oligonucleotides are described in many references, e.g., Marshall, Histochemical J., 7: 299-303 (1975); Menchen et al., U.S. Pat. No. 5,188,934; Menchen et al., European Patent Application 87310256.0; and Bergot et al., International Application PCT/US90/05565. All are hereby incorporated by reference.

Each member of the fluorophore/quencher pair can be attached anywhere within the oligonucleotide, preferably at a distance from the other of the pair such that sufficient amount of quenching occurs when the oligonucleotides are not cleaved or is hybridized to the template nucleic acid.

In one embodiment, one can use two interactive labels (e.g., FRET or non-FRET pairs) on a single oligonucleotide probe with due consideration given for maintaining an appropriate spacing of the labels on the oligonucleotide to permit the separation of the labels during oligonucleotide probe unfolding (e.g., for example due to a change in the secondary structure of the probe) or hydrolysis.

In another embodiment, one can use two interactive labels (e.g., FRET or non-FRET pairs) on a single oligonucleotide probe (e.g., third oligonucleotide) with due consideration given for maintaining an appropriate spacing of the labels on the oligonucleotide to permit the separation of the labels during a non-invasive cleavage event but not to permit the separation of the labels in the event of an invasive cleavage event.

In certain embodiments, the fluorescence of the released label is then compared to the label remaining bound to the target. It is not necessary to separate the nuclease (e.g. FEN-nuclease) generated fragment and the probe that remains bound to the target after cleavage in the presence of nuclease (e.g. FEN-nuclease) if the probe is synthesized with a fluorophore and a quencher that are separated by about 20 nucleotides. Alternatively, the quencher is positioned such that the probe will not fluoresce when not hybridized to the target nucleic acid sequence. Such a dual labeled probe will not fluoresce when intact or when not hybridized to the target nucleic acid sequence (or in the case of bi- or multimolecular probes, when the probe is not dissociated) because the light emitted from the dye is quenched by the quencher. Thus, any fluorescence emitted by an intact probe is considered to be background fluorescence. In one embodiment, when a labeled probe is cleaved by a FEN nuclease in a non-invasive cleavage reaction, dye and quencher are separated and the released fragment will fluoresce. Alternatively, when a labeled probe is hybridized to a target nucleic acid, the distance between the dye and the quencher is increased and the level of fluorescence increases. In an embodiment wherein the probe is a bi- or multi-molecular probe, dissociation of the molecules comprising the probe results in an increase in fluorescence. The amount of fluorescence is proportional to the amount of nucleic acid target sequence present in a sample.

One can also use multiple oligonucleotides in the present invention to achieve other benefits. For instance, one could test for any number of pathogens in a sample simply by putting as many probes as desired into the reaction mixture; the probes could each comprise a different label to facilitate detection. For example, multiple sets of different first oligonucleotides, second oligonucleotides, template nucleic acids and third oligonucleotides can be added to a reaction mixture. Each of the second oligonucleotides would be complementary to a region of a nucleic acid sequence from a different pathogen. If the pathogen is present in the reaction mixture the corresponding second oligonucleotide would hybridize to the pathogens nucleic acid sequence. The second oligonucleotide would be cleaved. The cleaved flap would then hybridize to a template nucleic acid specific for this flap. The flap, template and third oligonucleotide would form a second cleavage structure, which is cleaved. Cleavage of the third oligonucleotide would produce a signal indicative of the particular pathogen. Multiple different signals, e.g., fluorescent signals, could be generated for each pathogen of interest. Such reactions can be conducted in the Mx3005P Real Time PCR system (Stratagene, Calif.).

Although oligonucleotide sequence can be selected to achieve important benefits, one can also realize important advantages by selection of probe labels(s). The labels may be attached to the oligonucleotide directly or indirectly by a variety of techniques. Depending on the precise type of label used, the label can be located at the 5' or 3' end of the probe, located internally in the probe, or attached to spacer arms of various sizes and compositions to facilitate signal interactions. Using commercially available phosphoramidite reagents, one can produce oligomers containing functional groups (e.g., thiols or primary amines) at either the 5' or the 3' terminus via an appropriately protected phosphoramidite, and can label them using protocols described in, for example, PCR Protocols: A Guide to Methods and Applications, Innis et al., eds. Academic Press, Ind., 1990.

Methods for introducing oligonucleotide functionalizing reagents to introduce one or more sulfhydryl, amino or hydroxyl moieties into the oligonucleotide probe sequence, typically at the 5' terminus, are described in U.S. Pat. No. 4,914,210. A 5' phosphate group can be introduced as a radioisotope by using polynucleotide kinase and gamma-$^{32}$P-ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides that can be incorporated into a nucleic acid probe. Similarly, etheno-dC or 2-amino purine deoxyriboside is another analog that could be used in probe synthesis. The probes containing such nucleotide derivatives may be hydrolyzed to release much more strongly fluorescent mononucleotides by flap-specific nuclease activity.

A labeled probe having a secondary structure (e.g., key probe) that changes upon binding of the probe to the target nucleic acid sequence is used to prepare a labeled cleavage structure according to the invention. A labeled probe according to the invention may have a secondary structure as defined herein, (including a stem loop, a hairpin, an internal loop, a bulge loop, a branched structure and a pseudoknot) or multiple secondary structures, cloverleaf type structures or any three-dimensional structure. Labeled probes useful for forming a labeled cleavage structure according to the invention may also comprise covalently bound or non-covalently bound subunits (e.g., a bi-molecular or multi-molecular probe as defined herein).

Positioning a Fluorophore/Quencher Pair

As described above, in one embodiment the invention contemplates the use of a probe dual labeled with a fluorophore/quencher pair. When the labeled probe is cleaved by a FEN nuclease (or other nuclease as described herein), the fluorophore and quencher can be separated and the remaining fragment will fluoresce. It is contemplated that the placement of the fluorophore and quencher on the probe may be specifically selected to discriminate between non-overlapping (invasive) and overlapping (non-invasive) cleavage of the probe. It will be appreciated by one of skill in the art that the positioning of reporter molecules, although described in the context of a fluorophore/quencher pair, is not limited to that specific reporter system. The placement of the reporter molecules may also be applied to other reporter systems such as, for example, intercalating dyes, wherein the cleavage of the probe at a specific site would result in quenching of the dye signal. The placement scheme may also be used in any reporter system comprising interacting reporter molecules, where the interaction of the molecules may be interrupted by cleavage of the non-complementary portion of the probe. Such reporter systems are known in the art and described herein.

Pfu FEN cleaves the flap of a downstream probe (e.g., third oligonucleotide) predominantly at a single position relative to the 3' end of an upstream oligonucleotide (e.g., released flap of the second oligonucleotide) that is hybridized to a target/template nucleic acid. The nucleotides of the downstream probe that hybridize to the target are defined to be nucleotides +1 through +X, position +1 is defined as the 5' terminal nucleotide of the hybridized region of the downstream probe, region +2 is defined as the nucleotide which is immediately downstream of position +1 and so on. When the upstream oligonucleotide does not overlap with the downstream oligonucleotide's hybridized region, but abuts the downstream oligonucleotide such that there is only a one nucleotide gap between the complementary portions of the two oligonucleotides (e.g., created upon hybridization of an upstream oligonucleotide with a single 3' terminal non-complementary nucleotide and downstream oligonucleotide with a 5' non-complementary flap), FEN cleaves upstream of position +1 of the downstream oligonucleotide. If the upstream oligonucleotide has a single 3' base (either complementary or non-complementary to the target) that overlaps with the 5' end of the hybridized region of the probe, and hybridizes with the target at that 3' base position, then cleavage of the probe occurs downstream of the +1 position of the downstream oligonucleotide.

Accordingly, if one member of a pair of interactive labels, such as a quencher, is attached to base +1 of the hybridized region of the probe, and a fluorophore is attached to a base in the 5' flap, then cleavage downstream of position +1 will leave the quencher and the reporter group still attached to the same nucleic acid molecule. However, if cleavage were to occur upstream of position +1 of the probe, then the quencher located on base +1 will become separated from the reporter located on the flap. It also follows that if there is to be cleavage upstream of position +1, the upstream oligonucleotide cannot have an overlap with the hybridized region of the downstream probe. Thus, an overlapping structure (e.g., invasive cleavage structure) in which the upstream oligonucleotide has a 3' portion both complementary to the target and overlapping with the complementary portion of the downstream probe will cause cleavage downstream of position +1 or +2. Therefore there will be no physical separation of the quencher located on position +1 and the reporter group located in the 5' flap. Cleavage events resulting from overlapping (invasive cleavage) structures will be undetected, whereas cleavage events resulting from non-overlapping (non-invasive) cleavage structures (e.g., abutting upstream and downstream oligonucleotides) will be detectable. Thus, placement of the quencher molecule (such as a BHQ) at position +1 of the hybridized/complementary portion of the downstream probe permits the discrimination between invasive and non-invasive cleavage.

Accordingly, one embodiment of the invention contemplates the placement of a quencher (e.g., BHQ) at position +1 of the complementary region of the downstream primer and a fluorophore (e.g., FAM) upstream of the elbow. It is also contemplated that the positioning of the fluorophore/quencher pair may be reversed, such that the quencher is on the 5' flap and the fluorophore is located at position +1 of the complementary region of the downstream probe.

Accordingly, the invention contemplates the use of downstream probes having a fluorophore group (such as, but not limited to a FAM group) upstream of the elbow and a quencher on position +1 to generate signals only from non-invasive cleavage structures, and not from invasive cleavage structures.

In some embodiments, the probe with the selective placement of the interactive pair of labels is a cleavage resistant probe. In this embodiment, the probe can only be cleaved when a non-overlapping cleavage structure forms. Similarly, a detectable signal will only be produced upon formation and cleavage of a non-overlapping cleavage structure.

Therefore, provided that the upstream oligonucleotide does not have overlapping complementary with the downstream oligonucleotide cleavage will occur at or upstream of the +1 position. If the upstream oligonucleotide contains one or more base at its 3' end that overlaps with the hybridized region of the downstream oligonucleotide (e.g., invasive cleavage structure), cleavage will occur downstream of the +1 and both members of the pair of interacting labels C. Cleaving a Cleavage Structure and Generating a Signal A cleavage structure according to the invention can be cleaved by the methods described herein.

D. Detection of Released Labeled Fragments

Detection or verification of the labeled fragments may be accomplished by a variety of methods well known in the art and may be dependent on the characteristics of the labeled moiety or moieties comprising a labeled cleavage structure.

V. Cleavage Means

Nucleases useful according to the invention include any enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), and *Thermus flavus* (Tfl). Nucleases useful according to the invention also include DNA polymerases with 5'-3' exonuclease activity, including but not limited to eubacterial DNA polymerase I, including enzymes derived from *Thermus* species (Taq, Tfl, Tth, Tca (*caldophilus*) Tbr (*brockianus*), enzymes derived from *Bacillus* species (Bst, Bca, Magenta (full length polymerases, NOT N-truncated versions)), enzymes derived from *Thermotoga* species (Tma (*maritima*, Tne (*neopolitana*) and *E. coli* DNA polymerase I. The term nuclease also embodies FEN nucleases.

FEN-1 is an ~40 kDa divalent metal ion-dependent exo– and endonuclease that specifically recognizes the backbone of a 5' single-stranded flap strand and tracks down this arm to the cleavage site, which is located at the junction wherein the two strands of duplex DNA adjoin the flap. Both the endo- and exonucleolytic activities show little sensitivity to the base at the most 5' position at the flap or nick. Both FEN-1 endo- and exonucleolytic substrate binding and cutting are stimulated by an upstream oligonucleotide (flap adjacent strand or primer). This is also the case for E. coli pol I. The endonuclease activity of the enzyme is independent of the 5' flap length, cleaving a 5' flap as small as one nucleotide. The endonuclease and exonuclease activities are insensitive to the chemical nature of the substrate, cleaving both DNA and RNA.

Both the endo- and exonucleolytic activities are inhibited by concentrations of salts in the physiological range. The exonuclease activity is inhibited 50-fold at 50 mM NaCl as compared to 0 mM NaCl. The endonuclease activity is inhibited only sevenfold at 50 mM NaCl (Reviewed in Lieber 1997, supra).

Although a 5'-OH terminus is a good substrate for FEN-1 loading onto a 5' flap substrate, it serves as a very poor substrate when part of a nick in an otherwise double stranded DNA structure. The electrostatic repulsion by the terminal phosphate is likely to favor breathing of the substrate into a pseudo-flap configuration, providing the active form of the substrate for FEN-1. Such an explanation would indicate a single active site and a single mechanism of loading of FEN-1 onto the 5' ssDNA terminus of the flap or pseudo-flap configuration of the nick. Consistent with this model are observations that optimal activity at a nick requires very low $Mg^{2+}$ and monovalent salt concentrations, which destabilize base-pairing and would favor breathing of a nick to a flap. Higher $Mg^{2+}$ and monovalent salt concentrations would disfavor breathing and inhibit cutting of nicked or gapped structures that do require breathing to convert to a flap. Cleavage of stable flap structures is optimal at moderate $Mg^{2+}$ levels and does not decrease with increasing $Mg^{2+}$ concentration. This is because a flap substrate does not have to melt out base pairs to achieve its structure; hence, it is entirely insensitive to $Mg^{2+}$. Though the endonucleolytic activity decreases with monovalent salt, the decline is not nearly as sharp as that seen for the exonucleolytic activity. Furthermore, it has previously been shown that one-nucleotide flaps are efficient substrates. All of these observations are consistent with the fact that when FEN-1 has been interpreted to be functioning as an exonuclease, the size of the degradation products vary from one to several nucleotides in length. Breathing of nicks into flaps of varying length would be expected to vary with local sequence, depending on the G/C content. In summary, a nick breathing to form a transient flap means that the exonucleolytic activity of FEN-1 is the same as the endonucleolytic activity (Reviewed in Lieber, 1997, supra).

The endonuclease and exonuclease activities of FEN-1 cleave both DNA and RNA without requiring accessory proteins. At the replication fork, however, FEN-1 does interact with other proteins, including a DNA helicase and the proliferating cell nuclear antigen (PCNA), the processivity factor for DNA polymerases δ and ε. PCNA significantly stimulates FEN-1 endo- and exonucleolytic activity.

The FEN-1 enzymes are functionally related to several smaller bacteriophage 5'→3' exonucleases such as T5 5' exonuclease and T4 RNase H as well as to the larger eukaryotic nucleotide excision repair enzymes such as XPG, which also acts in the transcription-coupled repair of oxidative base damage. In eubacteria such as Escherichia coli and Thermus aquaticus, Okazaki processing is provided by the PolI 5'→3' exonuclease domain. These bacterial and phage enzymes share two areas of limited sequence homology with FEN-1, which are termed the N(N-terminal) and I (intermediate) regions, with the residue similarities concentrated around seven conserved acidic residues. Based on crystal structures of T4 RNase H and T5 exonuclease as well as mutagenesis data, it has been proposed that these residues bind to two $Mg^{2+}$ ions that are required for affecting DNA hydrolysis; however, the role each metal plays in the catalytic cycle, which is subtly different for each enzyme, is not well understood (Reviewed in Hosfield et al., 1998b, supra).

FEN-1 genes encoding FEN-1 enzymes useful in the invention include murine fen-1, human fen-1, rat fen-1, Xenopus laevis fen-1, and fen-1 genes derived from four archaebacteria Archaeglobus fulgidus, Methanococcus jannaschii, Pyrococcus furiosus and Pyrococcus horikoshii. cDNA clones encoding FEN-1 enzymes have been isolated from human (GenBank Accession Nos.: NM_004111 and L37374), mouse (GenBank Accession No.: L26320), rat (GenBank Accession No.: AA819793), Xenopus laevis (GenBank Accession Nos.: U68141 and U64563), and P. furiosus (GenBank Accession No.: AF013497). The complete nucleotide sequence for P. horikoshii flap endonuclease has also been determined (GenBank Accession No.: AB005215). The FEN-1 family also includes the Saccharomyces cerevisiae RAD27 gene (GenBank Accession No.: Z28113 Y13137) and the Saccharomyces pombe RAD2 gene (GenBank Accession No.: X77041). The archaeal genome of Methanobacterium thermautotrophiculum has also been sequenced. Although the sequence similarity between FEN-1 and prokaryotic and viral 5'-3' exonucleases is low, FEN-1s within the eukaryotic kingdom are highly conserved at the amino acid level, with the human and S. cerevisiae proteins being 60% identical and 78% similar. The three archaebacterial FEN-1 proteins are also, highly homologous to the eukaryotic FEN-1 enzymes (Reviewed in Matsui et al., 1999., J. Biol. Chem., 274:18297, Hosfield et al., 1998b, J. Biol. Chem., 273:27154 and Lieber, 1997, BioEssays, 19:233).

The sequence similarities in the two conserved nuclease domains (N-terminal or N and intermediate or I domains) between human and other FEN-1 family members are 92% (murine), 79% (S. cerevisiae), 77% (S. pombe), 72% (A. fulgidus), 76% (M. jannaschii), and 74% (P. furiosus).

FEN-1 specifically recognizes the backbone of a 5' single-stranded flap strand and migrates down this flap arm to the cleavage site located at the junction between the two strands of duplex DNA and the flap. If the strand upstream of the flap (sometimes called the flap adjacent strand or primer strand) is removed, the resulting structure is termed a pseudo-Y. This structure is cleaved by FEN-1, but at 20- to 100-fold lower efficiency. FEN-1 does not cleave 3' single-stranded flaps. However, FEN-1 acting as an exonuclease will hydrolyze dsDNA substrates containing a gap or nick (Reviewed in Hosfield et al., 1998a, supra, Hosfield et al., 1999b, supra, and Lieber 1997, supra). Exonucleolytically, FEN-1 acts at a nick and, with lower efficiency, at a gap or a recessed 5' end on dsDNA. At gapped structures, the efficiency of FEN-1 binding and cutting decreases with increasing gap size up to approximately five nucleotides and then stabilizes at a level of cleavage that is equivalent to activity on a recessed 5' end within dsDNA. Blunt dsDNA, recessed 3' ends and ssDNA are not cleaved (Reviewed in Lieber 1997, supra).

FEN nucleases that are useful according to the invention have been isolated from a variety of organisms including human (GenBank Accession Nos.: NM_004111 and L37374), mouse (GenBank Accession No.: L26320), rat (GenBank Accession No.: AA819793), yeast (GenBank Accession No.: Z28113 Y13137 and GenBank Accession No.: X77041) and *xenopus laevis* (GenBank Accession Nos.: U68141 and U64563). Such enzymes can be cloned and overexpressed using conventional techniques well known in the art.

A FEN nuclease according to the invention is preferably thermostable. Thermostable FEN nucleases have been isolated and characterized from a variety of thermostable organisms including four archeaebacteria. The cDNA sequence (GenBank Accession No.: AF013497) and the amino acid sequence (Hosfield et al., 1998a, supra and Hosfield et al., 1998b) for *P. furiosus* flap endonuclease have been determined. The complete nucleotide sequence (GenBank Accession No.: AB005215) and the amino acid sequence (Matsui et al., supra) for *P. horikoshii* flap endonuclease have also been determined. The amino acid sequence for *M. jannaschii* (Hosfield et al., 1998b and Matsui et al., 1999 supra) and *A. fulgidus* (Hosfield et al., 1998b) flap endonuclease have also been determined.

Thermostable FEN1 enzymes can be cloned and overexpressed using techniques well known in the art and described in Hosfield et al., 1998a, supra, Hosfield et al., 1998b, Kaiser et al., 1999, J. Biol. Chem., 274: 21387 and Matusi et al., supra and herein in Example 5 entitled "Cloning Pfu FEN-1".

The endonuclease activity of a FEN enzyme can be measured by a variety of methods including the following.

A. Fen Endonuclease Activity Assay

Figure 6:
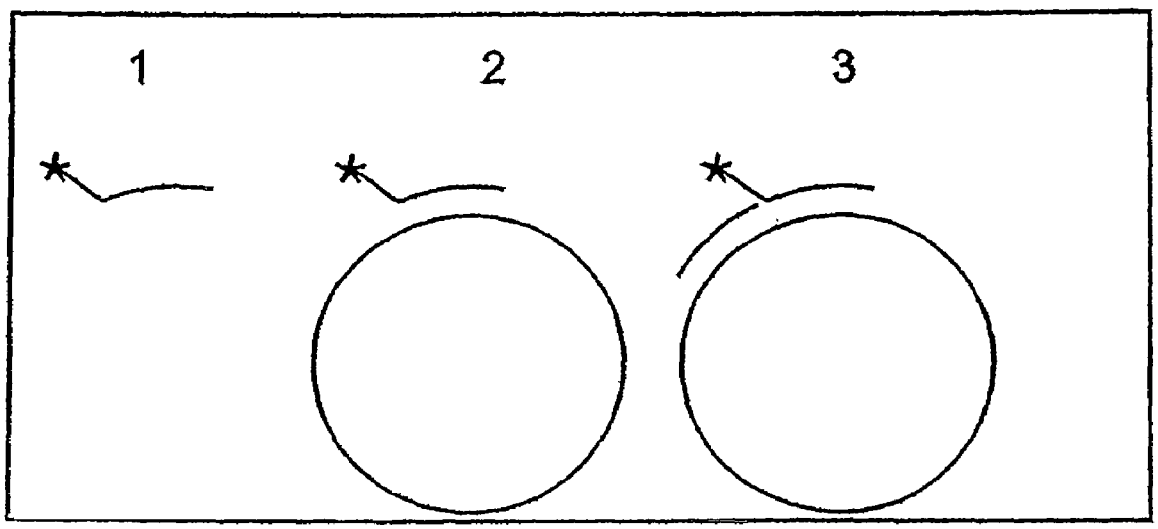
FIG. 6 demonstrates three templates (1, 2, 3) that may be used to detect Fen activity.

1. Templates (for example as shown in FIG. 6) are used to evaluate the activity of a FEN nuclease according to the invention.

Template 1 is a $5'^{33}P$ labeled oligonucleotide (Heltest4) with the following sequence: 5'AAAATAAATAAAAAAAAT ACTGTTGGGAAGGGCGATCGGTGCG 3'. The underlined section of Heltest4 represents the region complementary to M13mp18+. The cleavage product is an 18 nucleotide fragment with the sequence AAAATAAATAAAAAAAAT.

Heltest4 binds to M13 to produce a complementary double stranded domain as well as a non-complementary 5' overhang. This duplex forms template 2 (FIG. 6) which is also used for helicase assays. Template 3 (FIG. 6 has an additional primer (FENAS) bound to M13 and is directly adjacent to Heltest 4. The sequence of FENAS is: 5'CCATTCGCCAT-TCAGGCTGCGCA 3'. In the presence of template 3, FEN binds the free 5' terminus of Heltest4, migrates to the junction and cleaves Heltest4 to produce an 18 nucleotide fragment. Templates 1 and 2 serve as controls, although template 2 can also serve as a template.

Templates are prepared as described below:

|  | Template 1 | Template 2 | Template 3 |
|---|---|---|---|
| Heltest4 | 14 μl | 14 μl | 14 μl |
| M13 | ** | 14 μl | 14 μl |
| FENAS | ** | ** | 14 μl |
| H$_2$O | 28 μl | 14 μl | ** |
| 10x Pfu Buff. | 4.6 μl | 4.6 μl | 4.6 μl |

10× Pfu buffer is available from Stratagene (Stratagene Catalog #600153). According to the method of the invention, 10× Pfu buffer is diluted such that a reaction is carried out in the presence of 1× buffer.

M13 is M13mp18+ strand and is at a concentration of 200 ng/μL, $^{33}P$ labeled Heltest4 is at an approximate concentration of 0.7 ng/μl, and FENAS is at a concentration of 4.3 ng/μl. Based on these concentrations, the Heltest4 and M13 are at approximately equal molar amounts ($5 \times 10^{-14}$) and FENAS is present in an approximately 10× molar excess ($6 \times 10^{-13}$).

The template mixture is heated at 95° C. for five minutes, cooled to room temperature for 45 minutes and stored at 4° C. overnight.

2 μl of FEN-1 or, as a control, H$_2$O are mixed with the three templates as follows:

| |
|---|
| 3 μl template |
| 0.7 μl 10x cloned Pfu buffer |
| 0.56 μl 100 mM MgCl$_2$ |
| 2.00 μl enzyme or H$_2$O |
| 0.74 μl H$_2$O |
| 7.00 μl total volume |

The reactions are allowed to proceed for 30 minutes at 50° C. and stopped by the addition of 2 μl formamide "Sequencing Stop" solution to each sample. Samples are heated at 95° C. for five minutes and loaded on a 6% acrylamide, 7M urea CastAway (Stratagene) gel.

Alternatively, FEN activity can be analyzed in the following buffer wherein a one hour incubation time is utilized.

10×FEN Buffer 500 mM Tris-HCl pH 8.0

100 mM MgCl$_2$

The reaction mixture below is mixed with 2 μl of FEN or, as a control, 2 μl of H$_2$O.

| |
|---|
| 3 μl template |
| 0.7 μl 10x FEN buffer |
| 2.00 μl enzyme or H$_2$O |
| 1.3 μl H$_2$O |
| 7.00 μl total volume |

Samples are incubated for one hour at 50° C. in a Robocyler 96 hot top thermal cycler. Following the addition of 2 μl of Sequencing Stop dye solution, samples are heated at 99° C. for five minutes. Samples are loaded on an eleven-inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix (15% methanol, 5% acetic acid) and then for 10 minutes in water. The gel is placed on Whatmann 3 mm paper, covered with plastic wrap and dried for 2 hours in a heated vacuum gel dryer. The gel is exposed overnight to X-ray film.

2. FEN endonuclease activity can also be measured according to the method of Kaiser et al., supra). Briefly, reactions are carried out in a 10 μl volume containing 10 mM MOPS, pH 7.5, 0.05% Tween 20, 0.05% Nonidet P-40, 10 lg/ml tRNA, and 200 mM KCl for TaqPol and TthPol or 50 mM KCl for all other enzymes. Reaction conditions can be varied depending on the cleavage structure being analyzed. Substrates (2 μM) and varying amounts of enzyme are mixed with the indicated (above) reaction buffer and overlaid with Chill-out (MJ Research) liquid wax. Substrates are heat denatured at 90° C. for 20 s and cooled to 50° C., then reactions are started by addition of MgCl$_2$ or MnCl$_2$ and incubated at 50° C. for the specified length of time. Reactions are stopped by the addition of 1011 of 95% formamide containing 10 mM EDTA and 0.02% methyl violet (Sigma). Samples are heated to 90° C.

for 1 min immediately before electrophoresis on a 20% denaturing acrylamide gel (19:1 cross-linked), with 7M urea, and in a buffer of 45 mM Tris borate, pH 8.3, 1.4 mM EDTA. Unless otherwise indicated, 1 µl of each stopped reaction is loaded per lane. Gels are scanned on an FMBIO-100 fluorescent gel scanner (Hitachi) using a 505-nm filter. The fraction of cleaved product is determined from intensities of bands corresponding to uncut and cut substrate with FMBIO Analysis software (version 6.0, Hitachi). The fraction of cut product should not exceed 20% to ensure that measurements approximate initial cleavage rates. The cleavage rate is defined as the concentration of cut product divided by the enzyme concentration and the time of the reaction (in minutes). For each enzyme three data points are used to determine the rate and experimental error.

3. FEN endonuclease activity can also be measured according to the method of Hosfield et al., 1998a, supra. Briefly, in a final volume of 13 µl, varying amounts of FEN and 1.54 pmol of labeled cleavage substrate are incubated at different temperatures for 30 min before the reaction is quenched with an equal volume of stop solution (10 mM EDTA, 95% deionized formamide, and 0.008% bromophenol blue and xylene cyanol). Samples are electrophoresed through denaturing 15% polyacrylamide gels, and the relative amounts of starting material and product are quantitated using the IPLabGel system (Stratagene) running MacBAS image analysis software. Most reactions are performed in standard assay buffer (10 mM Tris-HCl (pH 8.0), 10 mM $MgCl_2$, and 50 µg/ml bovine serum albumin); however, in a series of experiments the effect of different divalent metals and pH levels are studied by varying the standard buffer. For divalent metals, $MgCl_2$ is omitted, and different metal ions are used at a final concentration of 10 mM. To study the influence of pH, buffers containing different amounts of Tris-HCl, glycine, and sodium acetate are used at a final concentration of 10 mM to obtain a wide range of pH levels at 25° C.

4. FEN endonuclease activity can also be measured according to the method of Matusi et al., 1999, supra. Briefly, the enzyme reactions are performed in a 15-µl reaction mixture containing 50 mM Tris-HCl (pH 7.4), 1.5 mM $MgCl_2$, 0.5 mM β-mercaptoethanol, 100 µg/ml bovine serum albumin, and 0.6 pmol of a labeled cleavage structure. After incubation for 30 min at 60° C., the reaction is terminated by adding 15 µl of 95% formamide containing 10 mM EDTA and 1 mg/ml bromphenol blue. The samples are heated at 95° C. for 10 min, loaded onto a 15% polyacrylamide gel (35 cm×42.5 cm) containing 7M urea and 10×TBE (89 mM Tris-HCl, 89 mM boric acid, 2 mM EDTA (pH 8.0)), and then electrophoresed for 2 h at 2000 V. Reaction products are visualized and quantified using a PhosphorImager (Bio-Rad). Size marker, oligonucleotides are 5' end-labeled with [γ-$^{32}$P]ATP and T4 polynucleotide kinase.

To determine the optimum pH, the reaction is performed in an assay mixture (15 µl) containing 1.5 mM $MgCl_2$, 0.5 mM β-mercaptoethanol, 100 µg/ml bovine serum albumin, and 0.6 pmol of 5' end-labeled cleavage structure in 50 mM of one of the following buffers at 60° C. for 30 min. Three different 50 mM buffers are used to obtain a wide pH range as follows: sodium acetate buffer (pH 4.0-5.5), phosphate buffer (pH 5.5-8.0), and borate buffer (pH 8.0-9.4).

B. FEN Exonuclease Activity Assay

The exonuclease activity of a FEN nuclease according to the invention can be measured by the method of measuring FEN-1 endonuclease activity described in Matsui et al., 1999, supra and summarized above.

Alternatively, the exonuclease activity of a FEN enzyme can be analyzed by the method described in Hosfield et al., 1998b, supra. Briefly, exonuclease activities are assayed using a nicked substrate of FEN under conditions identical to those described for the endonuclease assays (described above).

The precise positions of DNA cleavage in both the exonuclease and endonuclease experiments can be obtained by partial digestion of a 5'$^{32}$P-labeled template strand using the 3'-5' exonuclease activity of Klenow fragment.

A cleavage structure according to the invention is described in the section entitled "Cleavage Structure".

VI. Determining the Stability of the Secondary Structure of a Probe

A. Melting Temperature Assay

A melting temperature assay, takes advantage of the different absorption properties of double stranded and single stranded DNA, that is, double stranded DNA (the double stranded DNA being that portion of a nucleic acid sequence that has folded back on itself to generate an antiparallel duplex structure wherein complementary sequences (base pairs) are associated via hydrogen bonding) absorbs less light than single stranded DNA at a wavelength of 260 nm, as determined by spectrophotometric measurement.

Figure 2A:
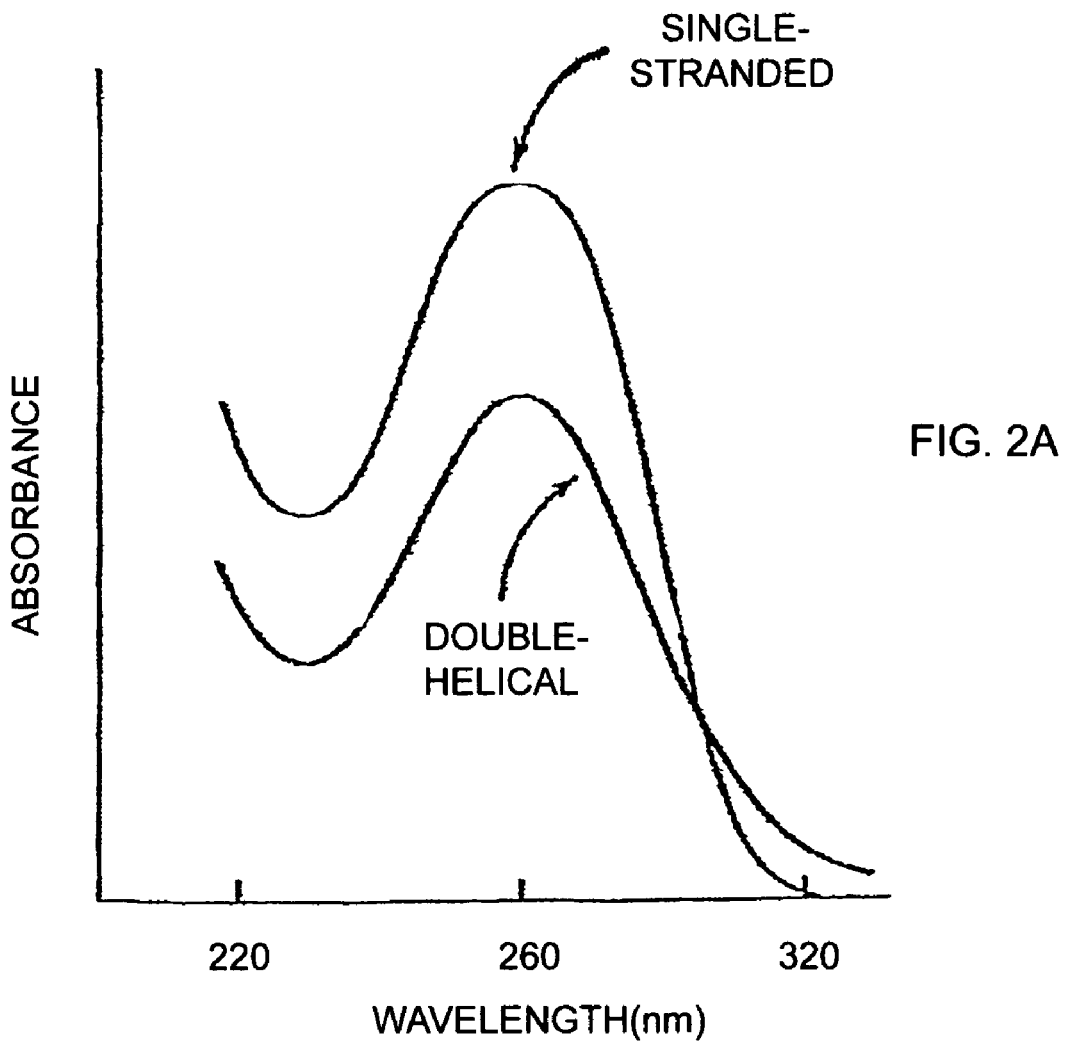
FIG. 2a is a graph demonstrating the difference in light absorbance of double-stranded versus single-stranded DNA.
Figure 2B:
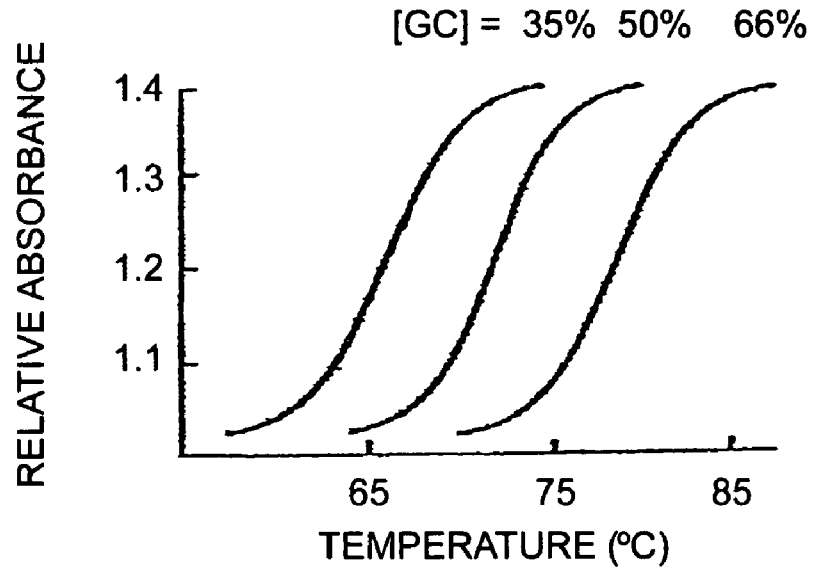
FIG. 2b is a graph demonstrating DNA melting curves.
Figure 2C:
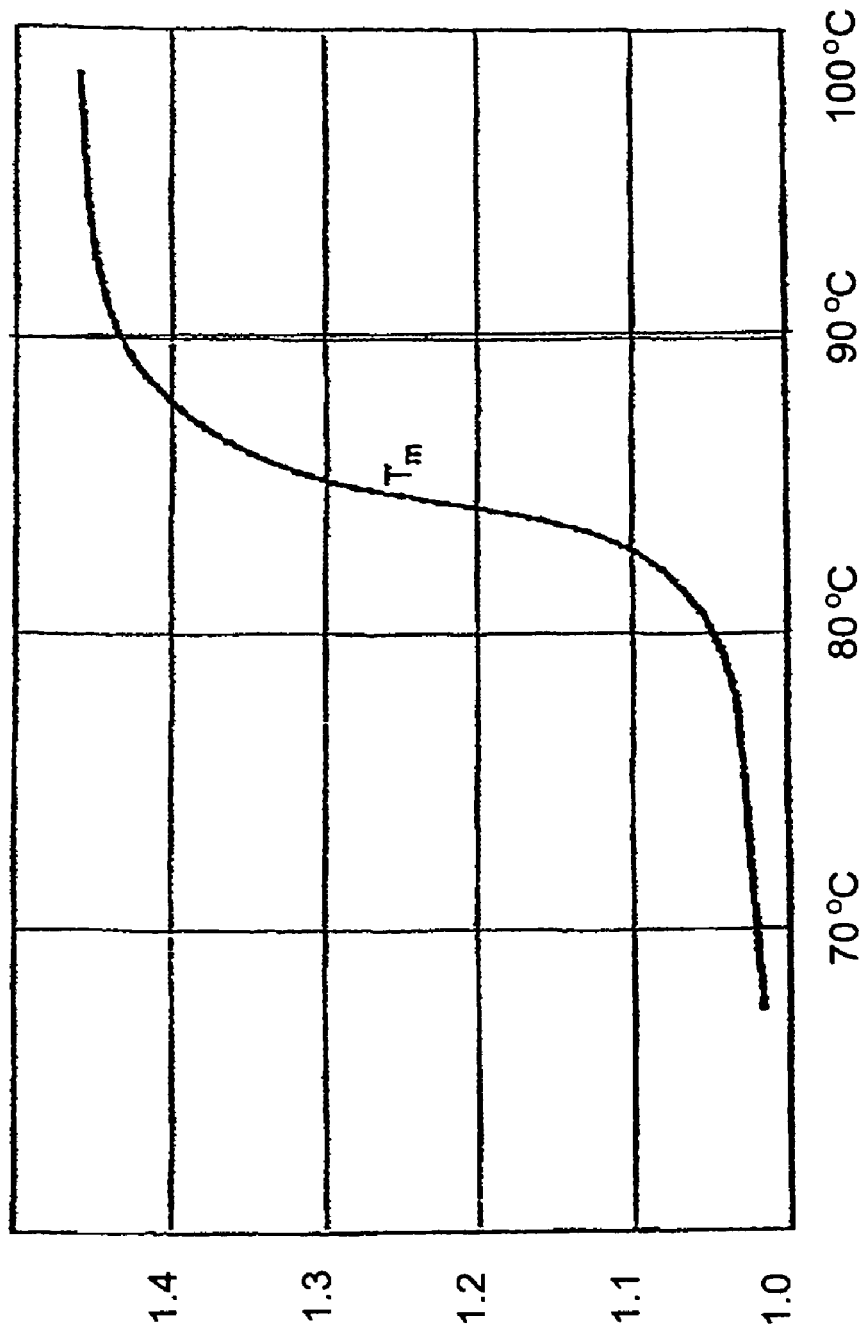
FIG. 2c is a graph demonstrating the effects of temperature on the relative light absorbance of DNA.
Figure 2D:
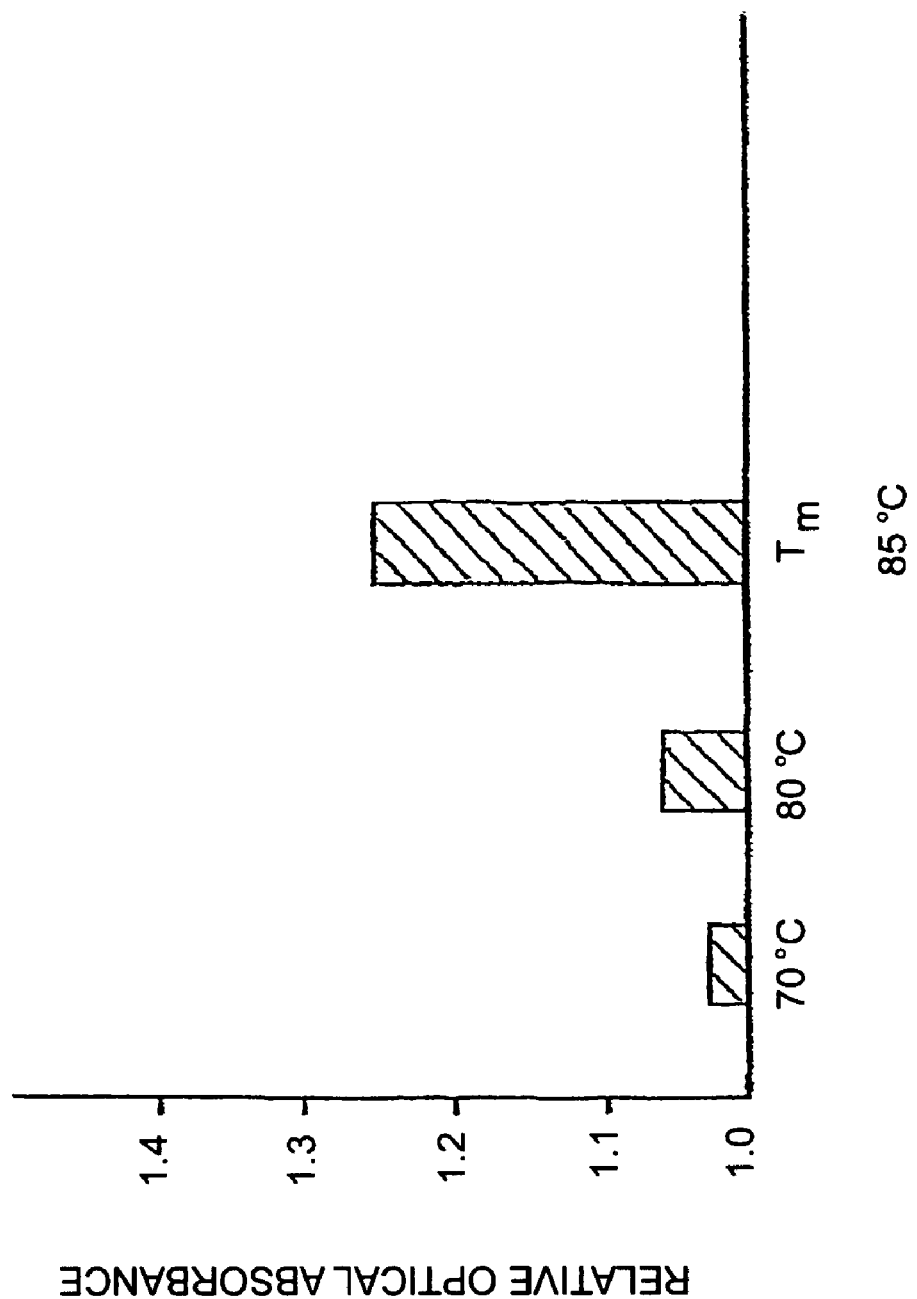
FIG. 2d is a graph demonstrating the effects of temperature on the relative optical absorbance of DNA.
Figure 2E:
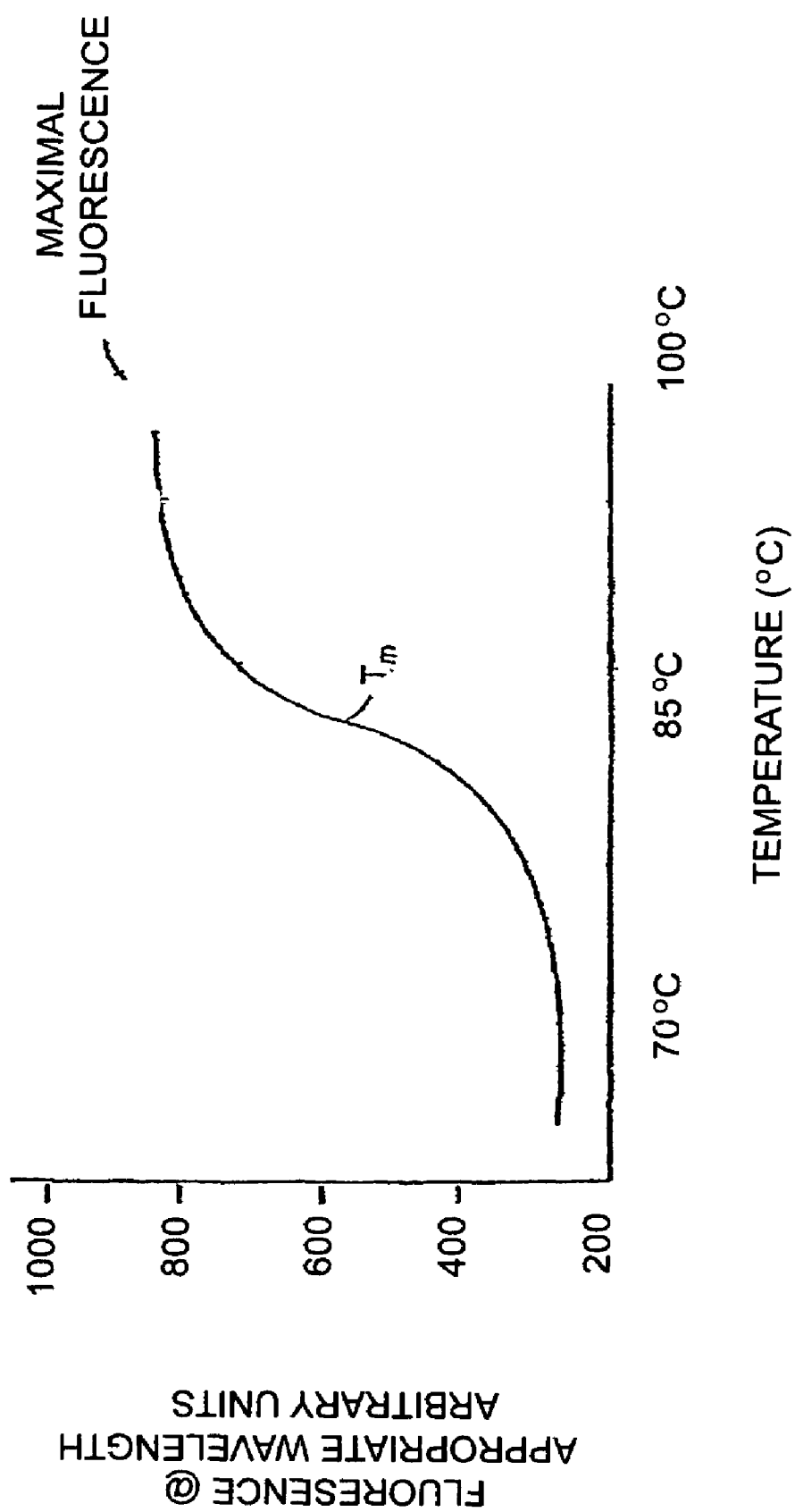
FIG. 2e is a graph demonstrating the effects of temperature on the fluorescence of DNA labeled with a pair of interactive labels.
Figure 2F:
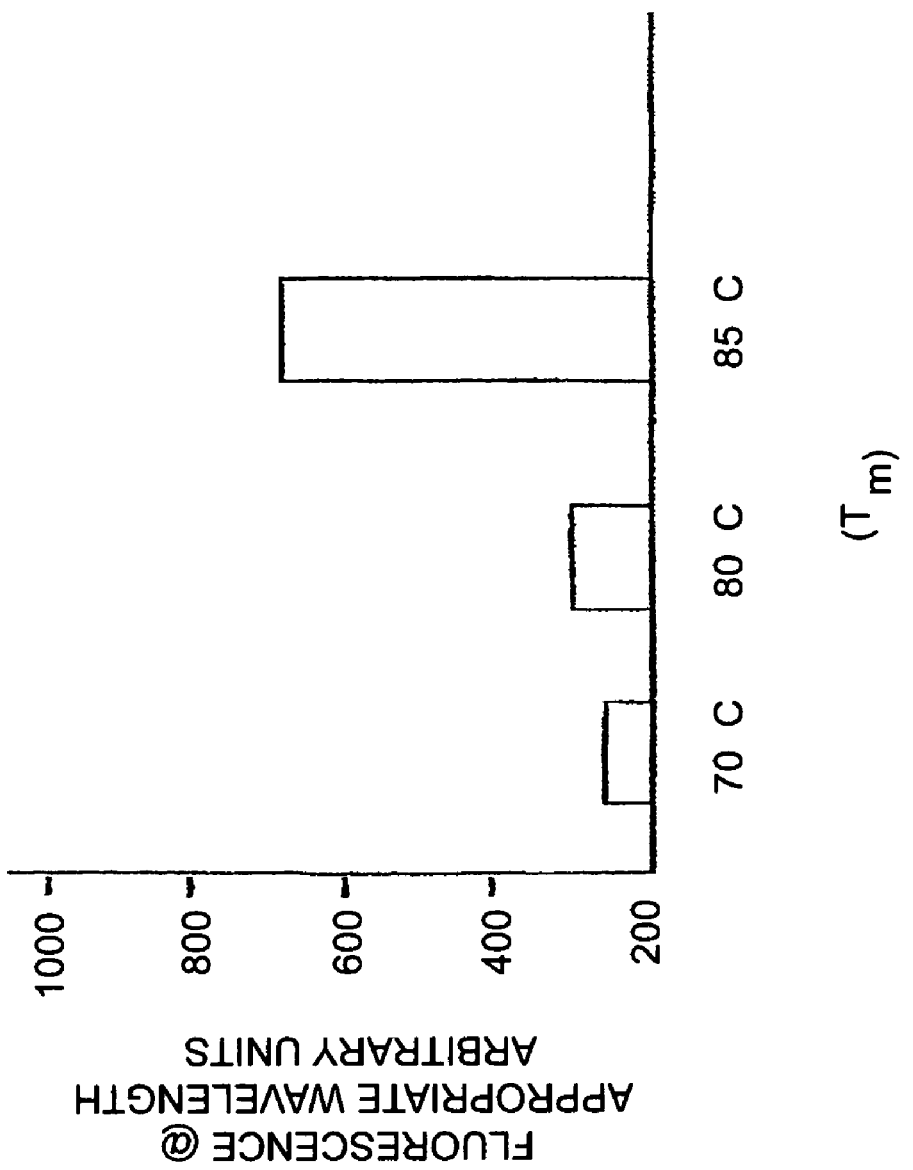
FIG. 2f is a graph demonstrating the effects of temperature on the fluorescence of DNA labeled with a pair of interactive labels.

The denaturation of DNA occurs over a narrow temperature range and results in striking changes in many of the physical properties of DNA. A particularly useful change occurs in optical density. The heterocyclic rings of nucleotides adsorb light strongly in the ultraviolet range (with a maximum close to 260 nm that is characteristic for each base). However, the adsorption of DNA is approximately 40% less than would be displayed by a mixture of free nucleotides of the same composition. This effect is called hyperchromism and results from interactions between the electron systems of the bases, made possible by their stacking in the parallel array of the double helix. Any departure from the duplex state is immediately reflected by a decline in this effect (that is, by an increase in optical density toward the value characteristic of free bases (FIG. 2a). The denaturation of double stranded DNA can therefore be followed by this hyperchromicity (FIGS. 2b and 2c)

The midpoint of the temperature range over which the strands of DNA separate is called the melting temperature, denoted $T_m$. An example of a melting curve determined by change in optical absorbance is shown in FIG. 2c. The curve always takes the same form, but its absolute position on the temperature scale (that is, its $T_m$) is influenced by both the base composition of the DNA and the conditions employed for denaturation.

The melting temperature of a DNA molecule depends markedly on its base composition. DNA molecules rich in GC base pairs have a higher Tm than those having an abundance of AT base pairs (FIG. 2b). The Tm of DNA from many species varies linearly with GC content, rising from 77° to 100° C. as the fraction of GC pairs increases from 20% to 78%. That is, the dependence of $T_m$ on base composition is linear, increasing about 0.4° C. for every percent increase in G—C content. GC base pairs are more stable than AT pairs because their bases are held together by three hydrogen bonds rather than by two. In addition, adjacent GC base pairs interact more strongly with one another than do adjacent AT base pairs. Hence, the AT-rich regions of DNA are the first to melt.

A major effect on $T_m$ is exerted by the ionic strength of the solution. The $T_m$ increases 16.6° C. for every tenfold increase in monovalent cation concentration. The most commonly used condition is to perform manipulations of DNA in 0.12 M phosphate buffer, which provides a monovalent Na+ concentration of 0.18M, and a $T_m$ of the order of 90° C.

The $T_m$ can be greatly varied by performing the reaction in the presence of reagents, such as formamide, that destabilize hydrogen bonds. This allows the $T_m$ to be reduced to as low as 40° C. with the advantage that the DNA does not suffer damage (such as strand breakage) that can result from exposure to high temperatures. (Stryer, *Biochemistry*, 1998, 3$^{rd}$ Edition, W.H. Freeman and Co., pp. 81-82 and Lewin, Genes II, 1985, John Wiley & Sons, p. 63-64).

The stability of the secondary structure of the probe according to the invention is determined in a melting temperature assay as follows.

A standard curve for the probe (for example FIG. 2c), wherein absorbance is plotted versus temperature, is prepared by incubating a sample comprising from about 0.2 µg/ml to 100 µg/ml of the probe in a buffer which allows for denaturing and reannealing of the probe at various temperature and for a time sufficient to permit denaturing and reannealing of the probe, and measuring the absorbance of a sample in a quartz cuvette (with a pathlength appropriate for the spectrophotometer being used, e.g., 1-cm), in a spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra). Standard curves are generated and compared, using a variety of buffers (e.g., 1×TNE buffer (10×-0.1M Tris base, 10 mM EDTA, 2.0 M NaCl, pH 7.4), FEN nuclease buffer, described herein, 1× Cloned Pfu buffer, described herein, 1× Sentinel Molecular beacon buffer, described herein) including a buffer that is possible and preferentially optimal for the particular nuclease to be employed in the cleavage reaction. The pH of the buffer will be monitored as the temperature increases, and adjusted as is needed.

The assay is performed in a single-beam ultraviolet to visible range (UV-VIS) spectrophotometer. Preferably, the assay is performed in a double-beam spectrophotometer to simplify measurements by automatically comparing the cuvette holding the sample solution to a reference cuvette (matched cuvette) that contains the blank. The blank is an equal volume of sample buffer.

The temperature of the spectrophotometer can be controlled such that the absorbance of the sample is measured at specific temperatures. Spectrophotometers useful according to the invention include but are not limited to the Beckman Coulter DU® 600/7000 Spectrophotometers in combination with the Micro™ Analysis Accessory (Beckman Coulter, Inc., Columbia, Md.).

The stability of the secondary structure of a probe at a particular temperature and in a buffer that is possible and preferentially optimal for the nuclease to be employed in the cleavage reaction of the probe, is determined by measuring the absorbance of the probe at a particular temperature, as above, and determining if the value of the absorbance is less than the absorbance at the Tm, as determined from the standard curve, wherein the standard curve is generated using either the same buffer as used at the test temperature, or a buffer known to produce a comparable standard curve, as described above. The secondary structure of the probe is "stable" in a melting temperature assay, at a temperature that is at or below the temperature of the cleavage reaction (i.e., at which cleavage is performed) if the level of light absorbance at the temperature at or below the temperature of the cleavage reaction is less (i.e., at least 5%, preferably 20% and most preferably 25% or more) than the level of light absorbance at a temperature that is equal to the Tm of the probe (see FIGS. 2c and 2d).

B. FRET

A FRET assay is useful in the invention for two purposes. The first is to determine whether the secondary structure of a probe is "stable" as defined herein. The second is to determine whether the secondary structure of the probe has undergone a "change" upon binding of the probe to the target nucleic acid or whether the probe has been cleaved by a cleavage means.

"FRET" is a distance-dependent interaction between the electronic excited states of two dye molecules in which excitation is transferred from a donor molecule to an acceptor molecule. FRET is caused by a change in the distance separating a fluorescent donor group from an interacting resonance energy acceptor, either another fluorophore, a chromophore, or a quencher. Combinations of donor and acceptor moieties are known as "FRET pairs". Efficient FRET interactions require that the absorption and emission spectra of the dye pairs have a high degree of overlap.

In most embodiments, the donor and acceptor dyes for FRET are different, in which case FRET can be detected by the appearance of sensitized fluorescence of the acceptor and/or by quenching of donor fluorescence. When the donor and acceptor are the same, FRET is detected by the resulting fluorescence depolarization. FRET is dependent on the inverse sixth power of the intermolecular separation (Stryer et al., 1978, *Ann. Rev. Biochem.*, 47:819; Selvin, 1995, *Methods Enzymol.*, 246:300).

As used herein, the term "donor" refers to a fluorophore which absorbs at a first wavelength and emits at a second, longer wavelength. The term "acceptor" refers to a fluorophore, chromophore or quencher with an absorption spectrum which overlaps the donor's emission spectrum and is able to absorb some or most of the emitted energy from the donor when it is near the donor group (typically between 1-100 nm). If the acceptor is a fluorophore capable of exhibiting FRET, it then re-emits at a third, still longer wavelength; if it is a chromophore or quencher, then it releases the energy absorbed from the donor without emitting a photon. Although the acceptor's absorption spectrum overlaps the donor's emission spectrum when the two groups are in proximity, this need not be the case for the spectra of the molecules when free in solution. Acceptors thus include fluorophores, chromophores or quenchers which exhibit either FRET or quenching when placed in proximity, on a probe according to the invention, to the donor due to the presence of a probe secondary structure that changes upon binding of the probe to the target nucleic acid, as defined herein. Acceptors do not include fluorophores, chromophores or quenchers that exhibit FRET or quenching a) at temperatures equal to or greater than the Tm (e.g. more than 5° C. above the Tm, for example 6° C., 10° C., 25° C., 50° C. or more above the Tm) or b) in the presence of a target nucleic acid.

Reference herein to "fluorescence" or "fluorescent groups" or "fluorophores" include luminescence, luminescent groups and suitable chromophores, respectively. Suitable luminescent probes include, but are not limited to, the luminescent ions of europium and terbium introduced as lanthium chelates (Heyduk & Heyduk, 1997). The lanthanide ions are also good donors for energy transfer to fluorescent groups (Selvin 1995). Luminescent groups containing lanthanide ions can be incorporated into nucleic acids utilizing an 'open cage' chelator phosphoramidite.

As used herein, the term "quenching" refers to the transfer of energy from donor to acceptor which is associated with a reduction of the intensity of the fluorescence exhibited by the donor.

The donor and acceptor groups may independently be selected from suitable fluorescent groups, chromophores and quenching groups. Donors and acceptors useful according to the invention include but are not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloylfluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), as well as suitable derivatives thereof.

In certain embodiments of the invention, a probe may also be labeled with two chromophores, and a change in the absorption spectra of the label pair is used as a detection signal, as an alternative to measuring a change in fluorescence.

In the method of the invention, fluorescence intensity of the probe is measured at one or more wavelengths with a fluorescence spectrophotometer or microtitre plate reader, according to methods known in the art.

C. Fluorescence Quenching Assay

A fluorescence quenching assay is useful in the invention for two purposes. The first is to determine whether the secondary structure of a probe is "stable" as defined herein. The second is to determine whether the secondary structure of the probe has undergone a "change" upon binding of the probe to the target nucleic acid.

A probe according to the invention is labeled with a pair of interactive labels (e.g., a FRET or non-FRET pair) wherein one member of the pair is a fluorophore and the other member of the pair is a quencher. For example, a probe according to the invention is labeled with a fluorophore and a quencher and fluorescence is measured in the absence of a target nucleic acid, over a range of temperatures, e.g., wherein the lower temperature limit of the range is at least 50° Celsius below, and the upper temperature limit of the range is at least 50° Celsius above the Tm or the predicted Tm of the probe.

D. Stability

The "stability" of the secondary structure of a probe according to the invention is determined as follows. A probe is labeled with a pair of interactive labels (either FRET or non-FRET pairs) described herein, according to methods well known in the art (for example, as described in Glazer and Mathies, 1997, Curr. Opin. Biotechnol., 8:94; Ju et al., 1995, Analytical Biochemistry, 231: 131)). The location of the interactive labels on the probe may be such that the labels are separated when the secondary structure of the probe changes following binding of the probe to the target nucleic acid.

A standard curve for the probe (for example FIG. 2e), wherein fluorescence is plotted versus temperature, is prepared by incubating a sample comprising typically 125 nM probe in 1× Melting Buffer (20 mM Tris-HCl, pH 8.0, 1 mM $MgCl_2$) or alternatively, in 5 mM Tris-HCl, pH 8.0, 0.1 mM EDTA, or other appropriate buffers for a time that is sufficient to permit denaturing and reannealing of the probe (typically the standard curve is generated using a fluorometer or spectrometer that undergoes a 1° C. per minute change, and measuring the fluorescence in a fluorometer or scanning fluorescence spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra).

Standard curves are generated and compared, using a variety of buffers (e.g., 1×TNE buffer (10×-0.1M Tris base, 10 mM EDTA, 2.0 M NaCl, pH 7.4), FEN nuclease buffer, described herein, 1× Cloned Pfu buffer, described herein, described herein) including a buffer that is possible and preferentially optimal for the particular nuclease to be employed in the cleavage reaction. The pH of the buffer will be monitored as the temperature increases, and adjusted as is needed.

The temperature of the fluorometer or spectrophotometer can be controlled such that the fluorescence of the sample is measured at specific temperatures. Fluorescence can be measured for example with a Perkin-Elmer LS50B Luminescence Spectrometer in combination with a temperature regulatable water bath (e.g., for example available from Fisher Scientific).

The stability of the secondary structure of a probe at a particular temperature is determined by measuring the fluorescence of the probe at a particular temperature, as above, and determining if the value of the fluorescence is less than the fluorescence at the Tm, as determined from the standard curve. The secondary structure of the probe is "stable" in a FRET assay, at a temperature that is at or below the temperature of the cleavage reaction (i.e., at which cleavage is performed) if the level of fluorescence at the temperature at or below the temperature of the cleavage reaction is altered (i.e., at least 5%, preferably 20% and most preferably 25% more or less than) the level of fluorescence at a temperature that is equal to the Tm of the probe. The secondary structure of the probe is "stable" in a fluorescence quenching assay, at a temperature that is at or below the temperature of the cleavage reaction (i.e., at which cleavage is performed) if the level of fluorescence at the temperature at or below the temperature of the cleavage reaction is altered (i.e., at least 5%, preferably 20% and most preferably 25% more or less than) the level of fluorescence at a temperature that is equal to the Tm of the probe.

Alternatively, the stability of the secondary structure of the probe is determined by modifying the method of Gelfand et al. (1999, Proc. Natl. Acad. Sci. USA, 96:6113), incorporated herein by reference, to determine the fluorescence of a probe labeled with a pair of interactive labels over a range of temperatures, as described hereinabove.

VII. Detecting a Secondary Structure

A secondary structure according to the invention may be detected by generating a standard curve of fluorescence versus temperature for a probe comprising a pair of interactive labels in a FRET assay, as described above (see FIG. 2e). A probe that exhibits a change in fluorescence that correlates with a change in temperature (see FIG. 2e) (e.g., fluorescence increases as the temperature of the FRET reaction is increased) is capable of forming a secondary structure.

VIII. Measuring a Change in Secondary Structure

A "change" in secondary structure according to the invention may be detected by analyzing a probe comprising a pair of interactive labels in a FRET or fluorescence quenching assay at a particular temperature below the Tm of the probe, (e.g., the cleaving temperature), as described above, in the presence of absence of 100 nM to 10 μM of a target nucleic acid sequence (typically the target nucleic acid sequence is in a 2-4 molar excess over the probe concentration, i.e., 250-500 nM target nucleic acid sequence is used).

Alternatively, a change in the secondary structure of the probe is determined by modifying the method of Gelfand et al. (1999, *Proc. Natl. Acad. Sci. USA*, 96:6113), incorporated herein by reference, to determine the fluorescence of a probe labeled with a pair of interactive labels in the presence or absence of a target nucleic acid as described hereinabove.

Figure 2G:
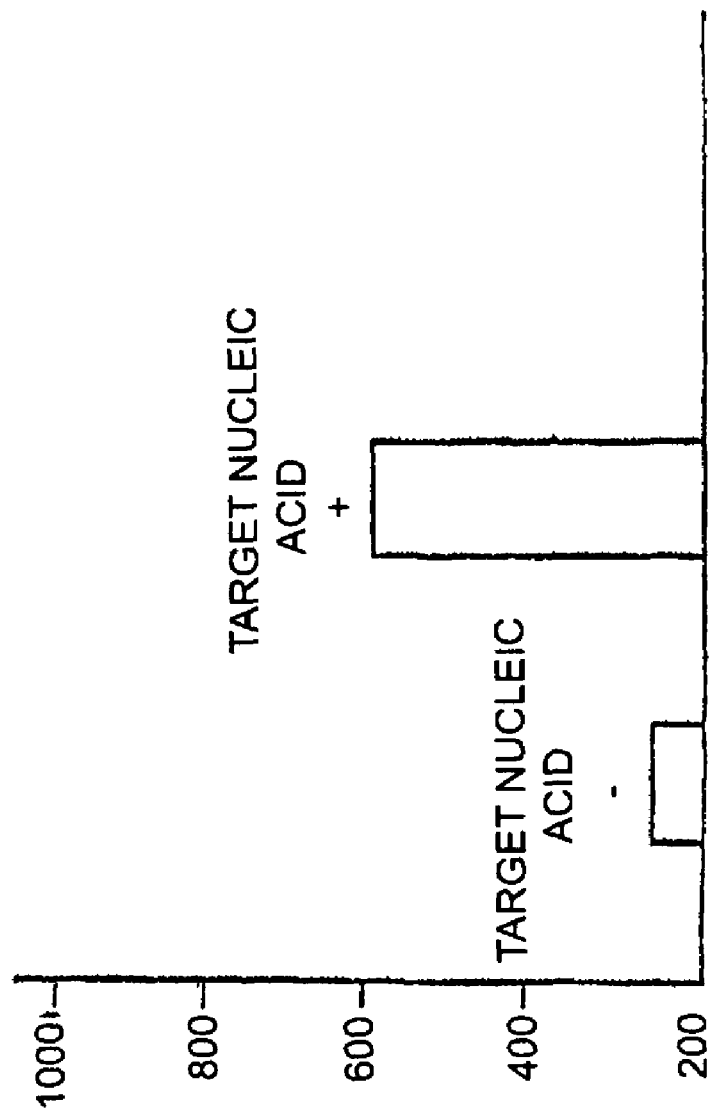
FIG. 2g is a graph demonstrating the effects of a target nucleic acid on the fluorescence of DNA labeled with a pair of interactive labels.

A "change" in secondary structure that occurs when a probe according to the invention binds to a target nucleic acid, and is cleaved by a non-invasive cleavage reaction is measured as an increase in fluorescence, such that the level of fluorescence after binding and cleavage of the probe to the target nucleic acid at the temperature below the Tm of the probe, is greater than (e.g., at least 5%, preferably 5-20% and more preferably 25 or more) the level of fluorescence observed in the absence of a target nucleic acid sequence (see FIG. 2g).

IX. Samples

The invention provides for a method of detecting or measuring a target nucleic acid sequence in a sample, as defined herein. As used herein, "sample" refers to any substance containing or presumed to contain a nucleic acid of interest (a target nucleic acid sequence) or which is itself a target nucleic acid sequence, containing or presumed to contain a target nucleic acid sequence of interest. The term "sample" thus includes a sample of target nucleic acid sequence (genomic DNA, cDNA or RNA), cell, organism, tissue, fluid or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

EXAMPLES

The invention is illustrated by the following nonlimiting examples wherein the following materials and methods are employed. The entire disclosure of each of the literature references cited hereinafter are incorporated by reference herein.

Example 1

Cloning Pfu FEN-1

A thermostable FEN nuclease enzyme useful according to the invention can be prepared according to the following method.

The thermostable FEN nuclease gene can be isolated from genomic DNA derived from *P. furiosus* (ATCC#43587) according to methods of PCR cloning well known in the art. The cloned PfuFEN-1 can be overexpressed in bacterial cells according to methods well known in the art and described below.

The following pCAL-n-EK cloning oligonucleotides were synthesized and purified:

a.
5'GACGACGACAAGATGGGTGTCCCAATTGGTGAGATTATACCAAGAAAA

G 3'
and b.
5'GGAACAAGACCCGTTTATCTCTTGAACCAACTTTCAAGGGTTGATTGT

TTTCCACT 3'.

The Affinity® Protein Expression and Purification System was obtained from Stratagene and used according to the manufacturer's protocols.

Amplification

The insert DNA was prepared by PCR amplification with gene-specific primers (oligonucleotides a and b, described above) that include 12 and 13-nucleotide sequences at the 5' ends that are complementary to the pCAL-n-EK vector single-stranded tails, thus allowing for directional cloning. The FEN-1 sequence was amplified from genomic DNA derived from *P. furiosus* by preparing amplification reactions (five independent 100 μl reactions) containing:

| | |
|---|---|
| 50 μl | 10x cPfu Buffer (Stratagene) |
| 7.5 μl | Pfu Genomic DNA (approx. 100 ng/μl) |
| 7.5 μl | PfuTurbo(2.5 u/μl), (Stratagene, Catalog # 600250) |
| 15 μl | mixed primer pair (100 ng/μl each) (oligonucleotides a and b, described above) |
| 4 μl | 100 mM dNTP |
| 416 μl | H₂O |
| 500 μl | total | and carrying out the amplification under the following conditions using a Stratagene Robocycler 96 hot top thermal cycler:

| | | | |
|---|---|---|---|
| Window 1 | 95° C. | 1 minute | 1 cycle |
| Window 2 | 95° C. | 1 minute | |
| | 50° C. | 1 minute | 30 cycles |
| | 72° C. | 3 minutes | |

The PCR products from each of the five reactions were combined into one tube, purified using StrataPrep PCR and eluted in 50 μl 1 mM Tris-HCl pH 8.6. The FEN-1 PCR product was analyzed on a gel and was determined to be approximately 1000 bp.

The PCR product comprising the fen-1 gene was cloned into the pCALnEK LIC vector (Stratagene) by creating ligation independent cloning termini (LIC), annealing the PCR product comprising the fen-1 gene to the pCALnEK LIC vector (Stratagene), and transforming cells with the annealing mixture according to the following method. Briefly, following PCR amplification, the PCR product is purified and treated with Pfu DNA polymerase in the presence of dATP (according to the manual included with the Affinity® Protein Expression and Purification System, Stratagene, catalog

204301). In the absence of dTTP, dGTP and dCTP, the 3' to 5'-exonuclease activity of Pfu DNA polymerase removes at least 12 and 13 nucleotides at the respective 3' ends of the PCR product. This activity continues until the first adenine is encountered, producing a DNA fragment with 5'-extended single-stranded tails that are complementary to the single-stranded tails of the pCAL-n-EK vector.

Creating LIC Termini

LIC termini were created by preparing the following mixture:

| | |
|---|---|
| 45 µl | purified PCR product (~0.5 µg/µl) |
| 2.5 µl | 10 mM dATP |
| 5 µl | 10x cPfu buffer |
| 1 µl | cPfu (2.5 u/µl) |
| 0.5 µl | H$_2$O | cPfu and cPfu buffer can be obtained from Stratagene (cPfu and cPfu buffer, Stratagene Catalog #600153).

Samples were incubated at 72° C. for 20 minutes and products were cooled to room temperature. To each sample was added 40 ng prepared pCALnEK LIC vector (the prepared vector is available commercially from Stratagene in the Affinity LIC Cloning and Protein Purification Kit (214405)). The vector and insert DNA are combined, allowed to anneal at room temperature and transformed into highly competent bacterial host cells (Wyborski et al., 1997, *Strategies*, 10:1).

Preparing Cells for Production of FEN

Two liters of LB-AMP was inoculated with 20 ml of an overnight culture of a FEN-1 clone (clone 3). Growth was allowed to proceed for approximately 11 hours at which point cells had reached an OD$_{600}$=0.974. Cells were induced overnight (about 12 hours) with 1 mM IPTG. Cells were collected by centrifugation and the resulting cell paste was stored at −20° C.

Purification of Tagged FEN-1

Cells were resuspended in 20 ml of Calcium binding buffer

CaCl$_2$ Binding Buffer 50 mM Tris-HCl (pH 8.0)

150 mM NaCl 1.0 mM MgOAc 2 mM CaCl$_2$

The samples were sonicated with a Branson Sonicator using a microtip. The output setting was 5 and the duty cycle was 90%. Samples were sonicated three times and allowed to rest on ice during the intervals. The sonicate was centrifuged at 26,890×g. Cleared supernatants were mixed with 1 ml of washed (in CaCl$_2$ binding buffer) calmodulin agarose (CAM agarose) in a 50 ml conical tube and incubated on a slowly rotating wheel in a cold room (40 C) for 5 hours. The CAM agarose was collected by light centrifugation (5000 rpm in a table top centrifuge).

Following removal of the supernatant, the CAM agarose was washed with 50 ml CaCl$_2$ binding buffer and transferred to a disposable drip column. The original container and pipet were rinsed thoroughly to remove residual agarose. The column was rinsed with approximately 200 ml of CaCl$_2$ binding buffer.

Elution was carried out with 10 ml of 50 mM NaCl elution buffer (50 mM NaCl, 50 mM Tris-HCl pH 8.0, 2 mM EGTA). 0.5 ml fractions were collected. A second elution step was carried out with 1M NaCl elution buffer wherein 0.5 ml fractions were collected.

Evaluation of Purified Tagged FEN-1

Figure 3:
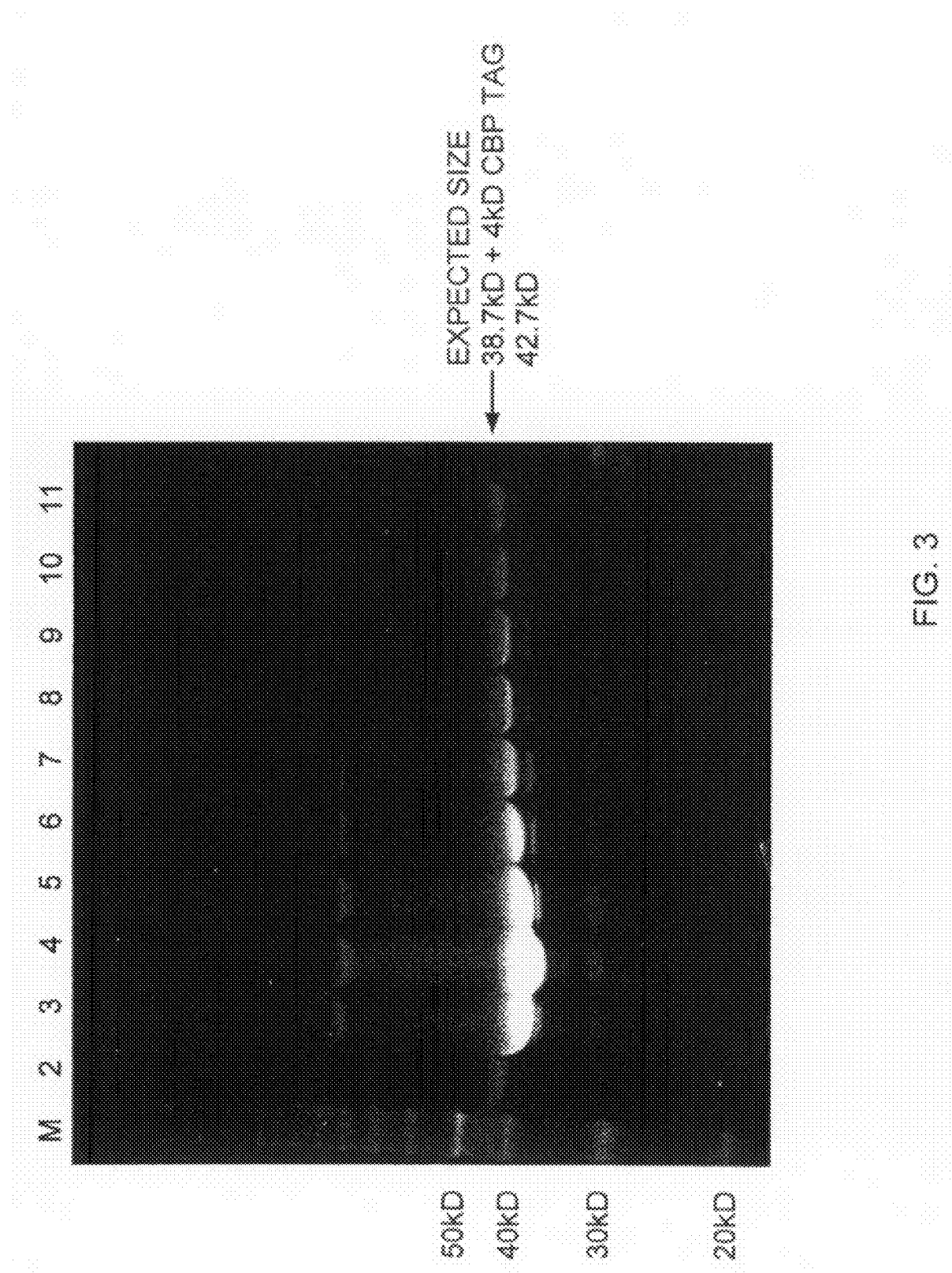
FIG. 3 is a Sypro Orange stained polyacrylamide gel demonstrating CBP-tagged PFU FEN-1 protein.

Fractions containing CBP-tagged Pfu FEN-1 eluted in 1M NaCl were boiled in SDS and analyzed by SDS-PAGE on a 4-20% gel stained with Sypro Orange (FIG. 3).

The protein concentration of uncleaved FEN-1 was determined to be approximately 150 ng/microliter (below).

Enterokinase Protease (EK) Cleavage of the Purified FEN-1

Fractions 3-9 were dialyzed in 50 mM NaCl, 50 mM Tris-HCl pH 8.0 and 2 mM CaCl$_2$ overnight at 4° C.

An opaque, very fine precipitate appeared in the dialyzed FEN-1. When the sample was diluted ½₀ the precipitate was removed. When the sample was diluted ⅓ insoluble material was still detectable. The ⅓ diluted material was heated at 37° C. for 2 minutes and mixed with Tween 20 to a final concentration of 0.1%. Upon the addition of the Tween 20, there was an almost immediate formation of "strings" and much coarser solids in the solution which could not be reversed even after the solution was adjusted to 1M NaCl.

EK cleavage was carried out using as a substrate the sample that was diluted ½₀ as well as with a dilute sample prepared by rinsing the dialysis bag with 1×EK buffer. EK cleavage was carried out by the addition of 1 µl EK (1 u/µl) overnight at room temperature (about 16 hours).

100 µl of STI agarose combined with 100 µl of CAM agarose were rinsed twice with 10 ml of 1×STI buffer (50 mM Tris-HCl pH 8.0, 200 mM NaCl, 2 mM CaCl$_2$, 0.1% Tween 20). NaCl was added to the two EK samples to bring the final concentration to 200 mM NaCl. The two samples were combined and added to the rinsed agarose. The samples were rotated slowly on a wheel at 4° C. for three hours and separated by light centrifugation in a table top centrifuge (as described). The supernatant was removed and the resin was rinsed twice with 500 µl 1×STI. The two rinses were combined and saved separately from the original supernatant. Samples were analyzed by SDS-PAGE on a 4-20% gel.

The concentration of digested product was approximately 23 ng/µl as determined by comparison to a Pfu standard at a concentration of approximately 50 ng/ml.

Example 2

FEN Nuclease Activity

The endonuclease activity of a FEN nuclease and the cleavage structure requirements of a FEN nuclease prepared as described in Example 1 can be determined according to the methods described either in the section entitled "FEN nucleases" or below.

Briefly, three templates (FIG. 6) are used to evaluate the activity of a FEN nuclease according to the invention. Template 1 is a 5'$^{33}$P labeled oligonucleotide (Heltest4) with the following sequence:

5'AAAATAAATAAAAAAAT<u>ACTGTTGGGAAGGGCGATCGGTGCG</u>3'.

The underlined section of Heltest4 represents the region complementary to M13 mp18+. The cleavage product is an 18 nucleotide fragment with the sequence AAAATAAATAAAAAAAAT. Heltest4 binds to M13 to produce a complementary double stranded domain as well as a non-complementary 5' overhang. This duplex forms template 2 (FIG. 6). Template 3 (FIG. 6) has an additional primer (FENAS) bound to M13 which is directly adjacent to Heltest 4. The sequence of FENAS is: 5'CCATTCGCCATTCAG-GCTGCGCA 3'. In the presence of template 3, a FEN nuclease binds the free 5' terminus of Heltest4, migrates to the junction and cleaves Heltest4 to produce an 18 nucleotide fragment. The resulting cleavage products are separated on a 6% acrylamide, 7M urea sequencing gel.

Templates are prepared as described below:

|  | Template 1 | Template 2 | Template 3 |
|---|---|---|---|
| Heltest4 | 14 μl | 14 μl | 14 μl |
| M13 | ** | 14 μl | 14 μl |
| FENAS | ** | ** | 14 μl |
| H$_2$O | 28 μl | 14 μl | ** |
| 10x Pfu Buff. | 4.6 μl | 4.6 μl | 4.6 μl |

Pfu buffer can be obtained from Stratagene (Catalog #600153).

The template mixture is heated at 95° C. for five minutes, cooled to room temperature for 45 minutes and stored at 4° C. overnight.

The enzyme samples are as follows:

A. H$_2$O (control)

B. 2 μl undiluted uncleaved FEN-1 (~445 ng/μl)

C. 2 μl 1/10 dilution of uncleaved FEN-1 (~44.5 ng/μl)

D. 2 μl enterokinase protease (EK) cleaved FEN-1 (~23 ng/μl)

The four reaction mixtures are mixed with the three templates as follows:

```
3    μl template 1, template 2 or template 3
0.7  μl 10x cloned Pfu buffer
0.6  μl 100 mM MgCl$_2$
2.00 μl FEN-1 or H$_2$O
0.7  μl H$_2$O 7.00 μl total volume
```

The reactions are allowed to proceed for 30 minutes at 50° C. and stopped by the addition of 2 μl formamide "Sequencing Stop" solution to each sample. Samples are heated at 95° C. for five minutes and loaded on a 6% acrylamide 7M urea CastAway gel (Stratagene).

Alternatively, FEN nuclease activity can be analyzed in the following buffer wherein a one hour incubation time is utilized.

10×FEN Nuclease Buffer 500 mM Tris-HCl pH 8.0

100 mM MgCl$_2$

The reaction mixture is as follows:

```
3    μl template 1, template 2 or template 3
0.7  μl 10x FEN nuclease buffer
2.00 μl FEN-1 or H$_2$O (A-D, above)
1.3  μl H$_2$O 7.00 μl total volume
```

Samples are incubated for one hour at 50° C. in the Robocyler 96 hot top thermal cycler. Following the addition of 2 μl of Sequencing Stop (95% formamide, 20 mM EDTA, 0.05% bromophenol blue, 0.05% xylene cyanol, available from Stratagene) dye solution, samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80 C). The gel is exposed overnight to X-ray film.

An autoradiograph of a FEN-1 nuclease assay wherein templates 1, 2 and 3 (prepared as described above) are cleaved by the addition of:

A. H$_2$O

B. 2 μl of CBP-tagged Pfu FEN-1

C. 2 μl of CBP-tagged Pfu FEN-1 diluted (1:10)

Figure 4:
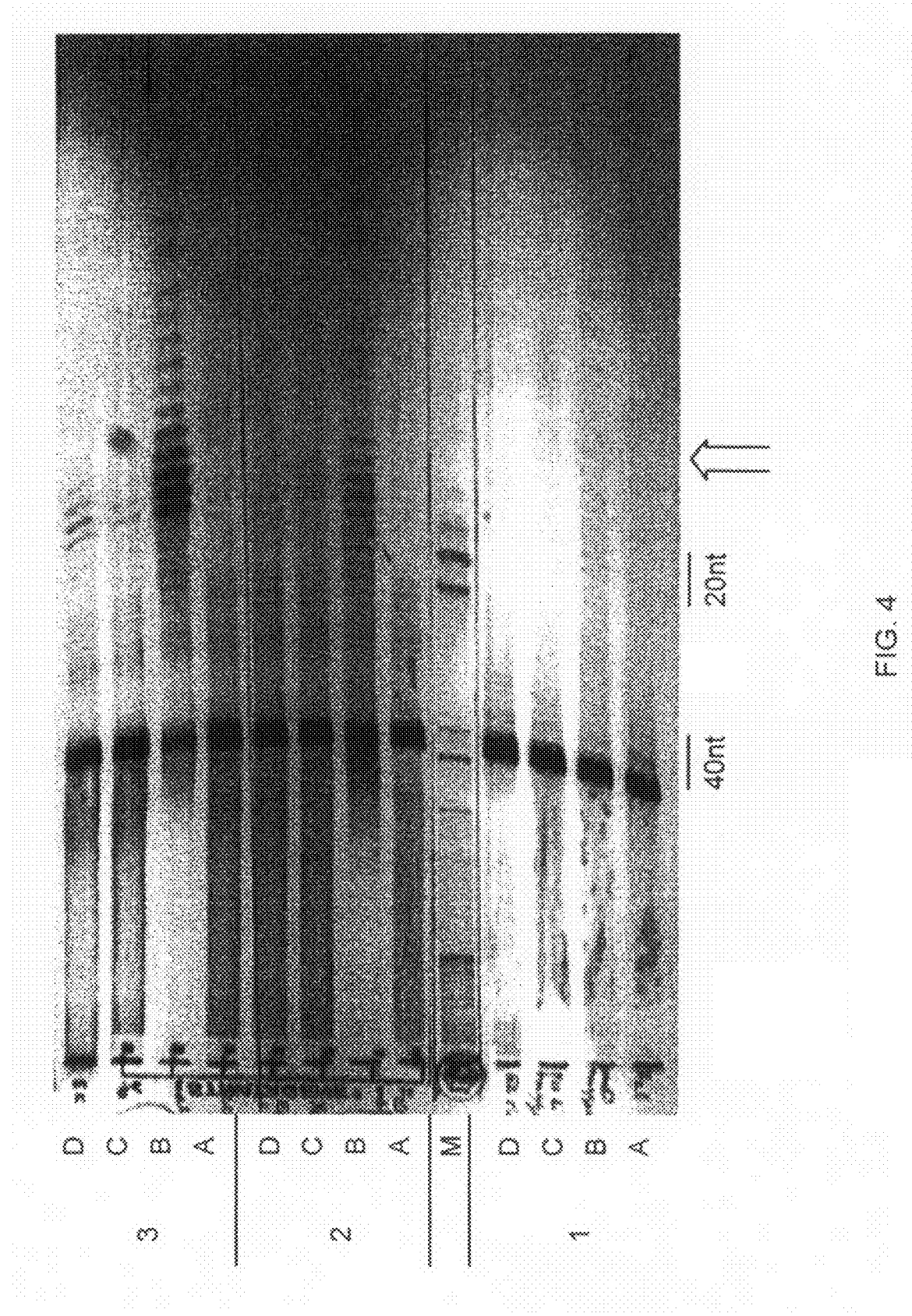
FIG. 4 is an autoradiograph of a FEN-1 nuclease assay.

D. 2 μl of EK cleaved Pfu FEN-1 is presented in FIG. 4.

The lanes are as follows. Lanes 1A, 1B, 1C and 1D represent template 1 cleaved with H$_2$O, undiluted CBP-tagged Pfu FEN-1, a 1:10 dilution of CBP-tagged Pfu FEN-1 and EK cleaved Pfu FEN-1, respectively. Lanes 2A, 2B, 2C and 2D represent template 2 cleaved with H$_2$O, undiluted CBP-tagged Pfu FEN-1, a 1:10 dilution of CBP-tagged Pfu FEN-1 and EK cleaved Pfu FEN-1, respectively. Lanes 3A, 3B, 3C and 3D represent template 3 cleaved with H$_2$O, undiluted CBP-tagged Pfu FEN-1, a 1:10 dilution of CBP-tagged Pfu FEN-1 and EK cleaved Pfu FEN-1, respectively.

Tagged Pfu FEN-1 contains the N-terminal CBP affinity purification tag. Any differences in activity between tagged and untagged versions of FEN-1 are due to differences in protein concentration (concentrations of enzyme samples are provided above) since the amounts of tagged versus untagged FEN-1 are not equivalent. Both tagged and untagged Pfu FEN-1 demonstrate cleavage activity.

FIG. 4 demonstrates the background level of cleavage in the absence of FEN-1 (lanes 1A, 2A and 3A). Further, this figure demonstrates that tagged Pfu FEN-1 cleaves more of template 2 as compared to template 1. In particular, the greatest amount of template 2 is cleaved in the presence of undiluted, tagged Pfu FEN-1 (lane 2B). Analysis of template 3 demonstrates that the greatest amount of template 3 is cleaved by undiluted, tagged Pfu FEN-1 and the least amount of template 3 is cleaved by diluted tagged FEN-1. Labeled probe migrates as a 40-43 nucleotide band. FEN-1 preferentially cleaves template 3 (which comprises an upstream primer) as compared to template 2. The cleavage product bands are the major bands migrating at 16-20 nucleotides. Heterogeneity in the labeled cleavage products is the result of heterogeneity in the labeled substrate, which was not gel-purified prior to use.

Example 3

Figure 1B:
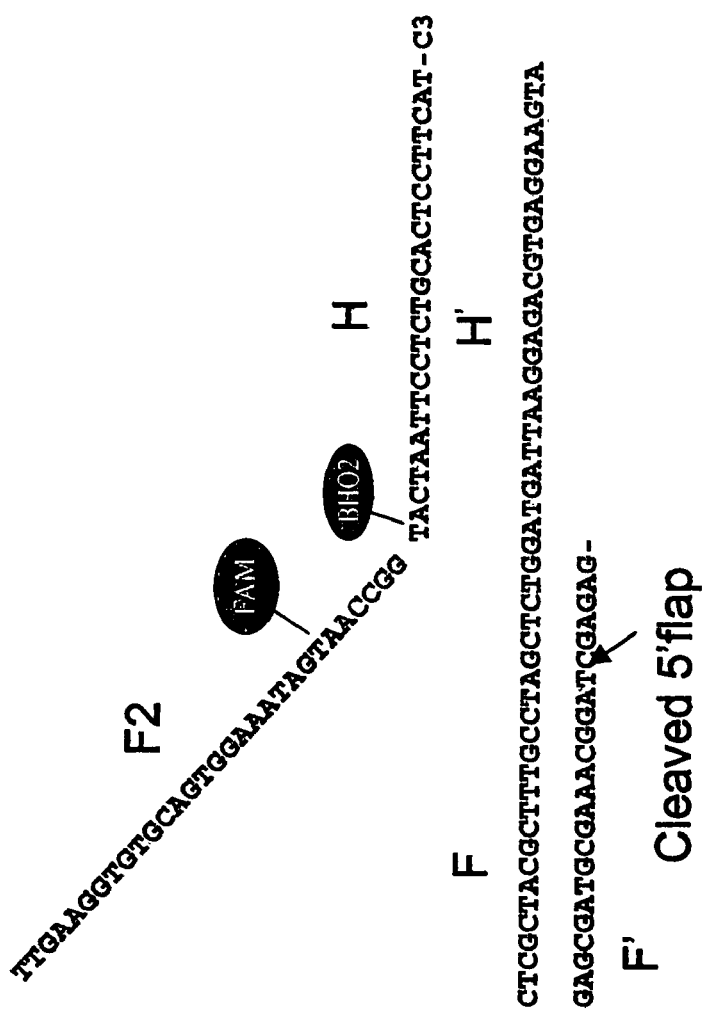

Real-Time QPCR Detection Utilizing the Oligonucleotides of the Invention that Only Generate a Detectable Signal Upon Cleavage of a Non-Invasive Cleavage Reaction A target nucleic acid sequence was detected and/or measured by the following method:

Reactions were prepared that contained the oligonucleotides illustrated in FIG. 1. The oligonucleotides included: a first oligonucleotide having a 3' non-complementary nucleotide (A-1, FIG. 1A), an upstream primer (A-2, FIG. 1A), a second oligonucleotide (F—C, FIG. 1A), a target nucleic acid (A'C', FIG. 1A), a template nucleic acid (F'H', FIG. 1B), and a third oligonucleotide (F2H, FIG. 1B). The 3' ends of the second oligonucleotide and third oligonucleotides were blocked. The first and second oligonucleotides were designed so that when hybridized to the target, the complementary portion of the first oligonucleotide and complementary portion of the second oligonucleotide were separated by a 1 nucleotide gap when annealed to the target (FIG. 1A). Similarly, the released flap and third oligonucleotide were also designed so that their template complementary portions formed a gap (2 nucleotide gap; FIG. 1B) when annealed to the template. Furthermore, in order to favor non-invasive cleavage reactions and not primer extension, the first oligonucleotide and released flap were designed to each have a 3' terminal non-complementary nucleotide.

The third oligonucleotide was coupled to a pair of interactive labels that generate a detectable signal when the oligonucleotide is cleaved at the elbow. This can only occur if the first cleavage reaction is non-invasive. This was accomplished by positioning FAM on the 5' flap of the third oligonucleotide and BHQ2 on the +1 nucleotide of the third oligonucleotide. Thus, if the first cleavage reaction was non-invasive, the released flap would hybridize to the template nucleic acid such that a 2 nucleotide gap would separate the 3' terminal complementary nucleotide from the complementary portion of the third oligonucleotide. This would result in cleavage of the third oligonucleotide at the elbow, therefore allowing the labels to separate. However, if the first cleavage reaction was invasive, the released flap would hybridize to the template nucleic acid such that one or more additional nucleotides would be included at the 3' end of the released flap. This would cause the second cleavage reaction to cleave downstream of the pair of interactive labels, the labels would not separate, and no signal would be produced.

The reaction conditions were as follows:

Primary System Components:
    10 to 1×10^6 copies of the target
    300 nM of A-2 oligonucleotide
    500 nm of A-1 oligonucleotide
    200 nm of reverse primer
    200 nm of second oligonucleotide Secondary System Components:
    600 nm of template nucleic acid (See FIG. 1)
    200 nm of third oligonucleotide (See FIG. 1)
    1× Probe buffer (15 mM of Tris-HCL (pH8), 50 mM KCL, 5.5 mM MgCl$_2$, 8% glycerol, 1% DMSO)+(NTPs)
    1.25 U Pfu V93R exo(−) polymerase,
    200 ng FEN-1 endonuclease The reaction mixture was placed in a thermal cycler and cycled under the following conditions:
    (1) 2 min at 95° C. for 1 cycle
    (2) 95° C. for 10 seconds
    (3) 60° C. for 30 seconds
    Steps (1) and (2) were repeated for 50 cycles.

Figure 7:
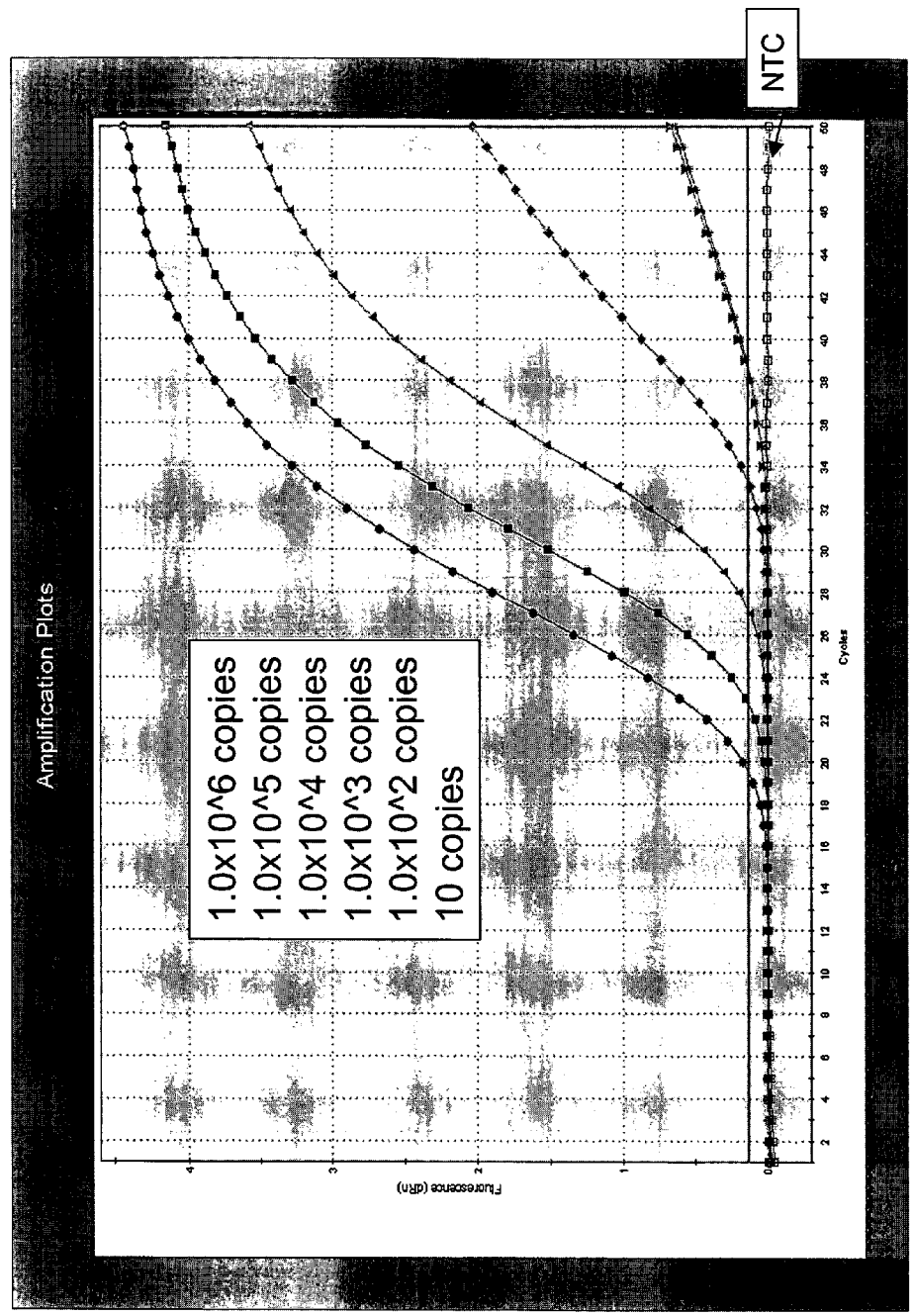
FIG. 7 is graph depicting a real-time fluorescent detection assay utilizing the oligonucleotides illustrated in FIG. 1.

Fluorescence data was collected at the end of the 60° C. step of each cycle. The results are graphically represented in FIG. 7. The results indicate that the present method is effective for detecting and determining the amount of a target nucleic acid in a sample.

Example 4

Real-Time QPCR Detection Utilizing a Single Cleavage Reaction That Only Generates a Detectable Signal Upon Cleavage of a Non-Invasive Cleavage Reaction One of ordinary skill in the art will understand that the above reaction can be performed in a non-sequential reaction. If the reaction were performed in a non-sequential manner the system may include:

System Components:
    10 to 1×10^6 copies of the target
    300 nM of A-2 oligonucleotide
    500 nm of A-1 oligonucleotide
    200 nm of reverse primer
    200 nm of second oligonucleotide (labeled)
    1× Probe buffer (15 mM of Tris-HCL (pH8), 50 mM KCL, 5.5 mM MgCl$_2$, 8% glycerol, 1% DMSO) (+NTPs)
    1.25 U Pfu V93R exo(−) polymerase,
    200 ng FEN-1 endonuclease The reaction mixture would then be placed in a thermal cycler and cycled under the following conditions:
    (1) 2 min at 95° C. for 1 cycle
    (2) 95° C. for 10 seconds
    (3) 60° C. for 30 seconds
    Steps (1) and (2) were repeated for 50 cycles.

Fluorescence data could be collected at the end of the 60° C. step of each cycle.

In this reaction the second oligonucleotide would be labeled with a pair of interactive labels as described above for the third oligonucleotide of the sequential cleavage reaction.

Example 5

Optimization of Primer/Upstream (First) Oligonucleotide Ratios

Figure 8A:
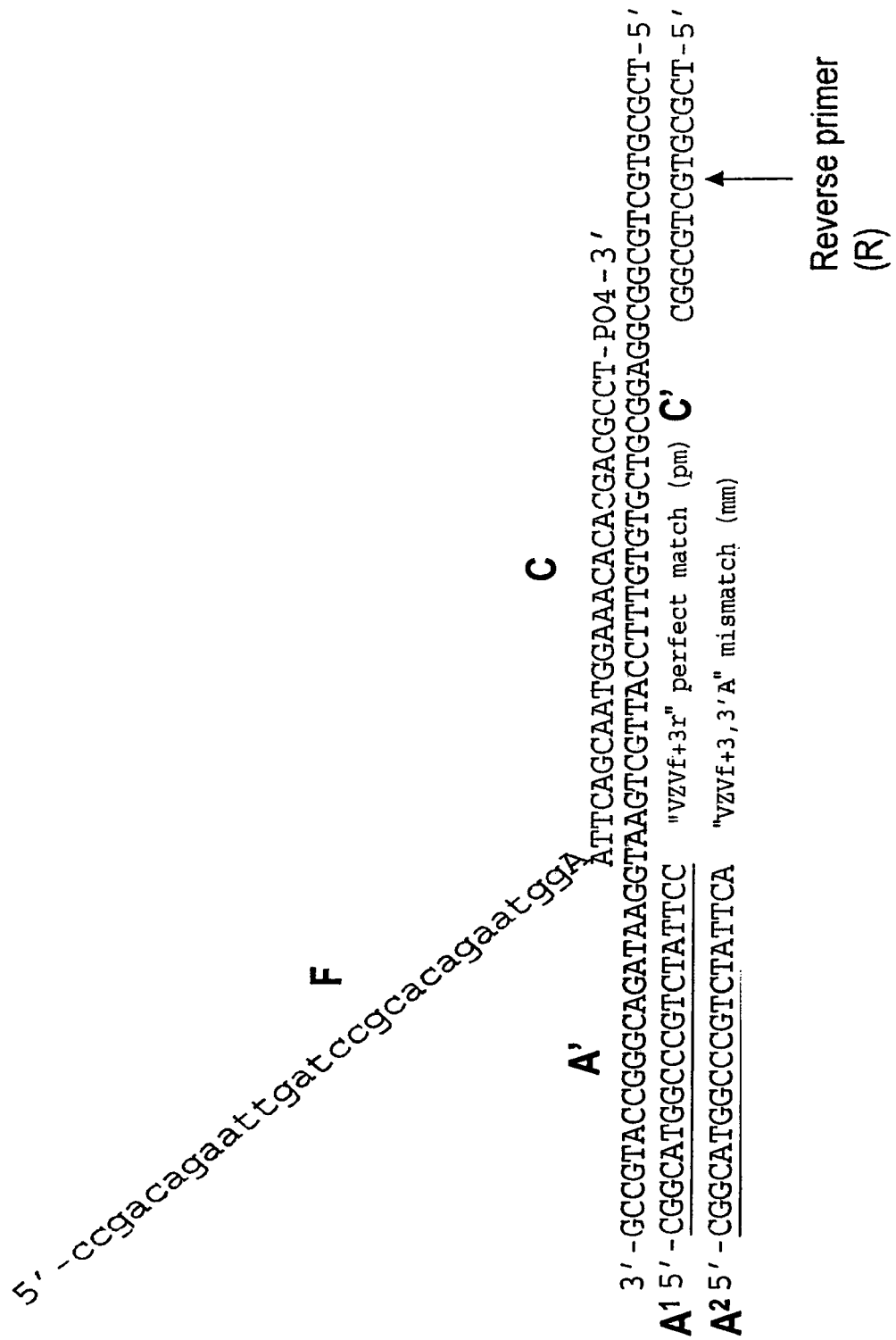
FIG. 8 illustrates another embodiment of the invention for detecting a target nucleic acid utilizing a first oligonucleotide and released flap that each have a 3' terminal non-complementary nucleotide.
Figure 8B:
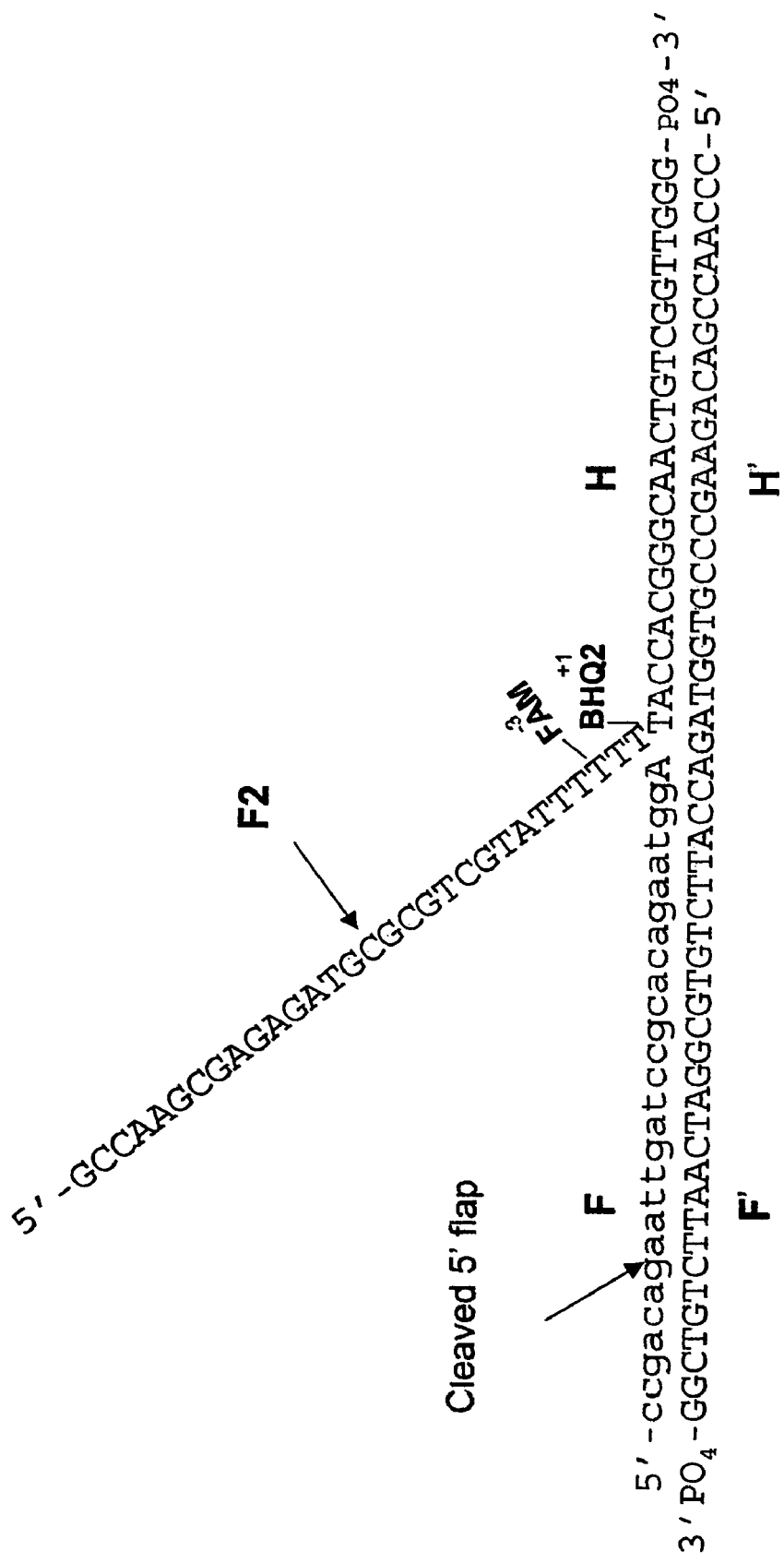
Figure 8C:
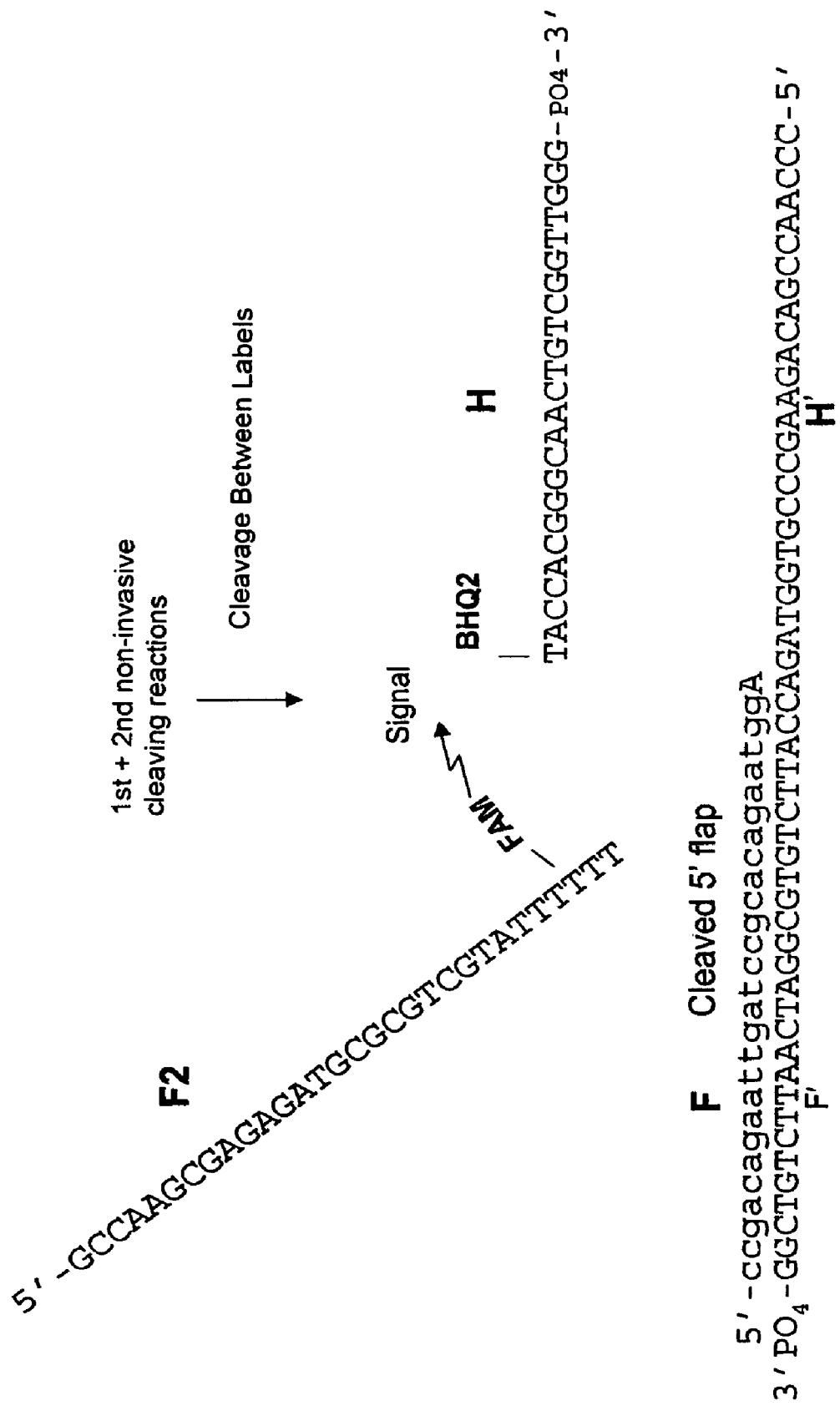

A target nuclei acid sequence was detected and/or measured by the following method in order to determine the optimal ratio of primer to upstream oligonucleotide:

Reactions were prepared containing the oligonucleotides illustrated in FIG. 8. The oligonucleotides included; a first oligonucleotide (A-1, FIG. 8A), an upstream primer (A-2, FIG. 8A), a reverse primer (R; FIG. 8A), a second oligonucleotide (F—C, FIG. 8A), a target nucleic acid (A'C', FIG. 8A), a template nucleic acid (F'H', FIG. 8B), and a third oligonucleotide (F2H, FIG. 8B). The 3' ends of the second oligonucleotide and third oligonucleotides were blocked. The third oligonucleotide contained a pair of interactive labels that generate a detectable signal when the labels are separated, e.g., cleavage of the elbow of the third oligonucleotide. FAM was coupled to the 5' flap of the third oligonucleotide while BHQ2 was coupled to the +1 nucleotide of the third oligonucleotide.

The concentration of the target and ratio of primer to upstream oligonucleotide were varied in the reaction mixtures. The reaction conditions were as follows:

Primary System Components:
    2.5 to 2.5×10^5 copies of the target
    400 nm of different primer mixes:
    Forward primer (A-2): upstream oligonucleotide (0:100)
    Forward primer (A-2): upstream oligonucleotide (10:90)
    Forward primer (A-2): upstream oligonucleotide (25:75)
    200 nm of reverse primer 200 nm of downstream oligonucleotide Secondary System Components:
  50 nm of template nucleic acid
  200 nm of third oligonucleotide
  1× Probe buffer (15 mM of Tris-HCL (pH8), 50 mM KCL, 5.5 mM $MgCl_2$, 8% glycerol, 1% DMSO) (+dNTP)
  1.25 U Pfu V93R exo(−) polymerase,
  100 ng FEN-1 endonuclease The reaction mixture was placed in a thermal cycler and cycled under the following conditions:
  (1) 2 min at 95° C. for 1 cycle
  (2) 95° C. for 1 second
  (3) 60° C. for 18 seconds
  Steps (1) and (2) were repeated for 55 cycles.

Figure 9:
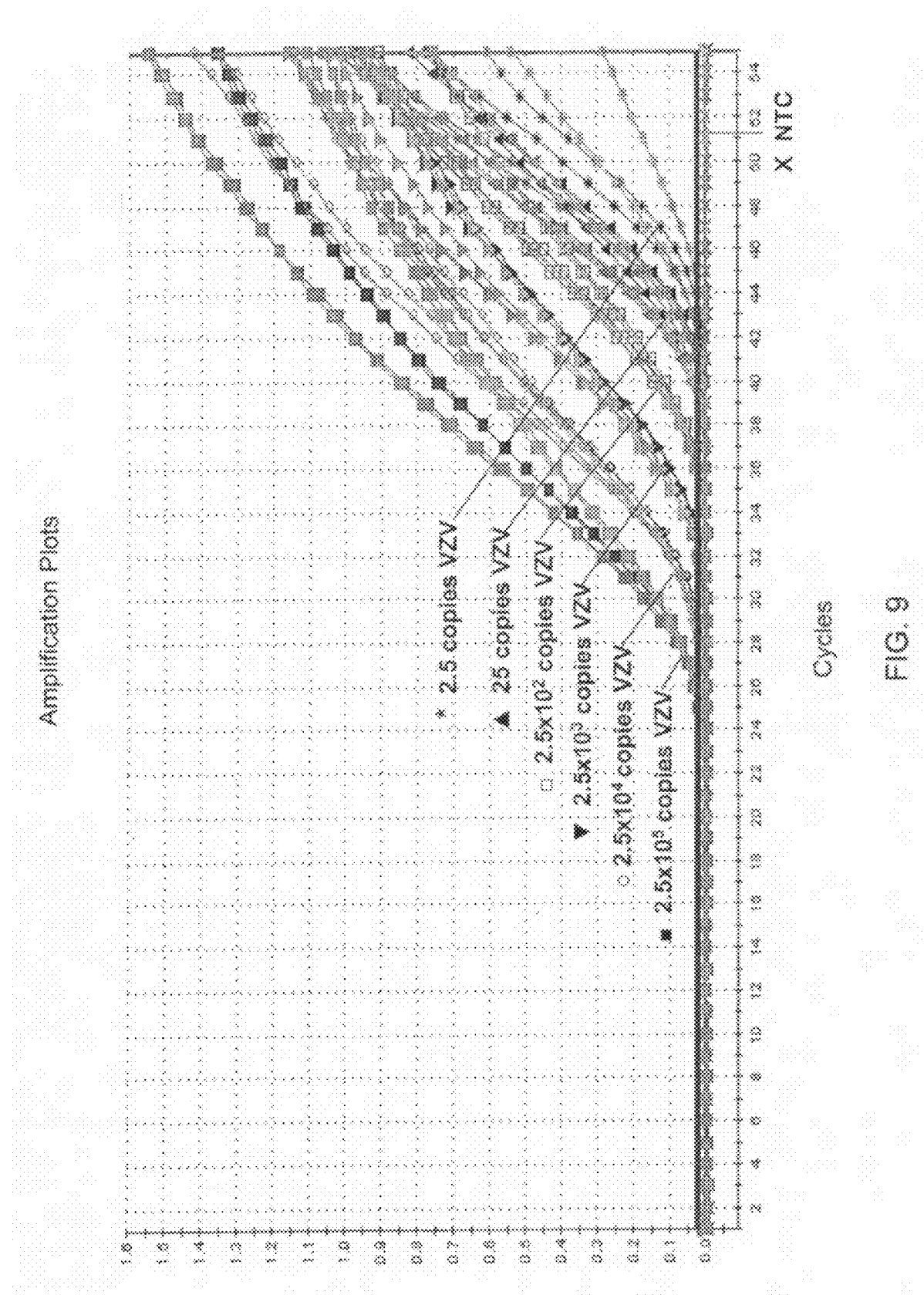
FIG. 9 is a graph from a real-time fluorescent detection assay described in Example 5.

Fluorescence data was collected at the end of the 60° C. step of each cycle. The results are graphically represented in FIG. 9. The results indicated that optimal primer:upsteam oligonucleotide ratio was 10:90.

Example 6

Optimization of the Placement of the Upstream Oligonucleotide and Downstream Probe on a Target In order to optimize the signal created by the cleavage of the third oligonucleotide, reactions were performed which varied the placement of the upstream oligonucleotide with respect to the downstream (third) oligonucleotide on a target. The third oligonucleotide had a FAM label coupled to the −3 position of the downstream oligonucleotide and BHQ 2 coupled to the +1. (See FIG. 8B)

The oligonucleotides illustrated in FIG. 8B were used in the present example. The oligonucleotides included; an upstream oligonucleotide (F, FIG. 8), a template nucleic acid (F'H', FIG. 8), and a third oligonucleotide (probe) (FH, FIG. 8). The length of the upstream oligonucleotide was varied and included the following oligos; the upstream oligonucleotide illustrated in FIG. 8b, the upstream oligonucleotide with one additional 3' nucleotide, the upstream oligonucleotide with two additional 3' nucleotides or the upstream oligonucleotide with 3 additional 3' nucleotides (2 nt overlap). The reaction conditions were as follows:
  200 nm of template nucleic acid
  200 nm of third oligonucleotide
  200 nm of upstream oligonucleotide (with 0-3 additional 3' nucleotides)
  1× Probe buffer (15 mM of Tris-HCL (pH8), 50 mM KCL, 5.5 mM $MgCl_2$, 8% glycerol, 1% DMSO) (+dNTP)
  +/−1.25 U Pfu V93R exo(−) polymerase,
  100 ng FEN-1 endonuclease The reaction mixture was placed in a thermal cycler and cycled under the following conditions:
  (1) 2 min at 95° C. for 1 cycle
  (2) 95° C. for 1 second
  (3) 60° C. for 18 seconds
  Steps (1) and (2) were repeated for 40 cycles.

Figure 10:
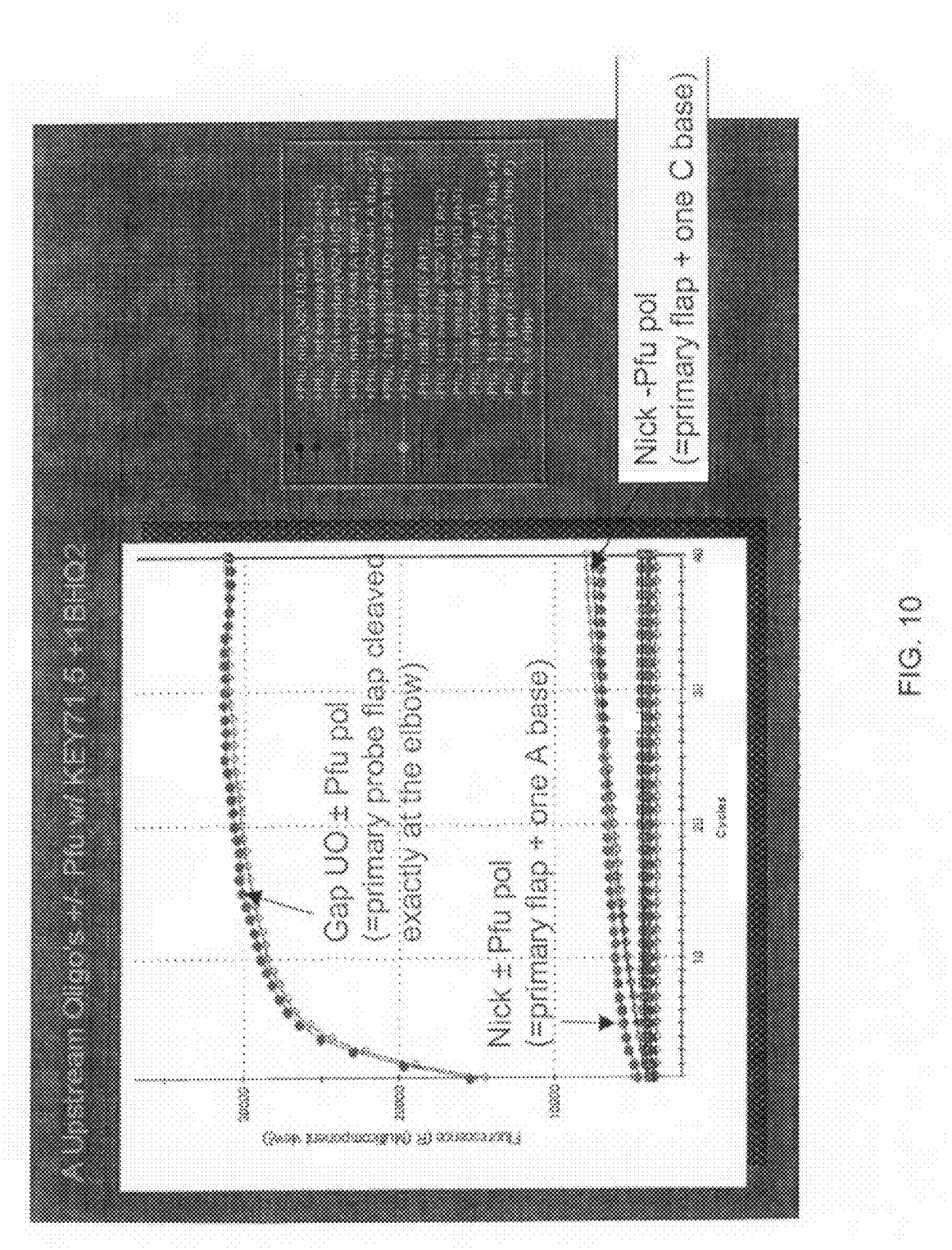
FIG. 10 is a graph depicting the real-time fluorescent detection assay described in Example 6.
Figure 11:
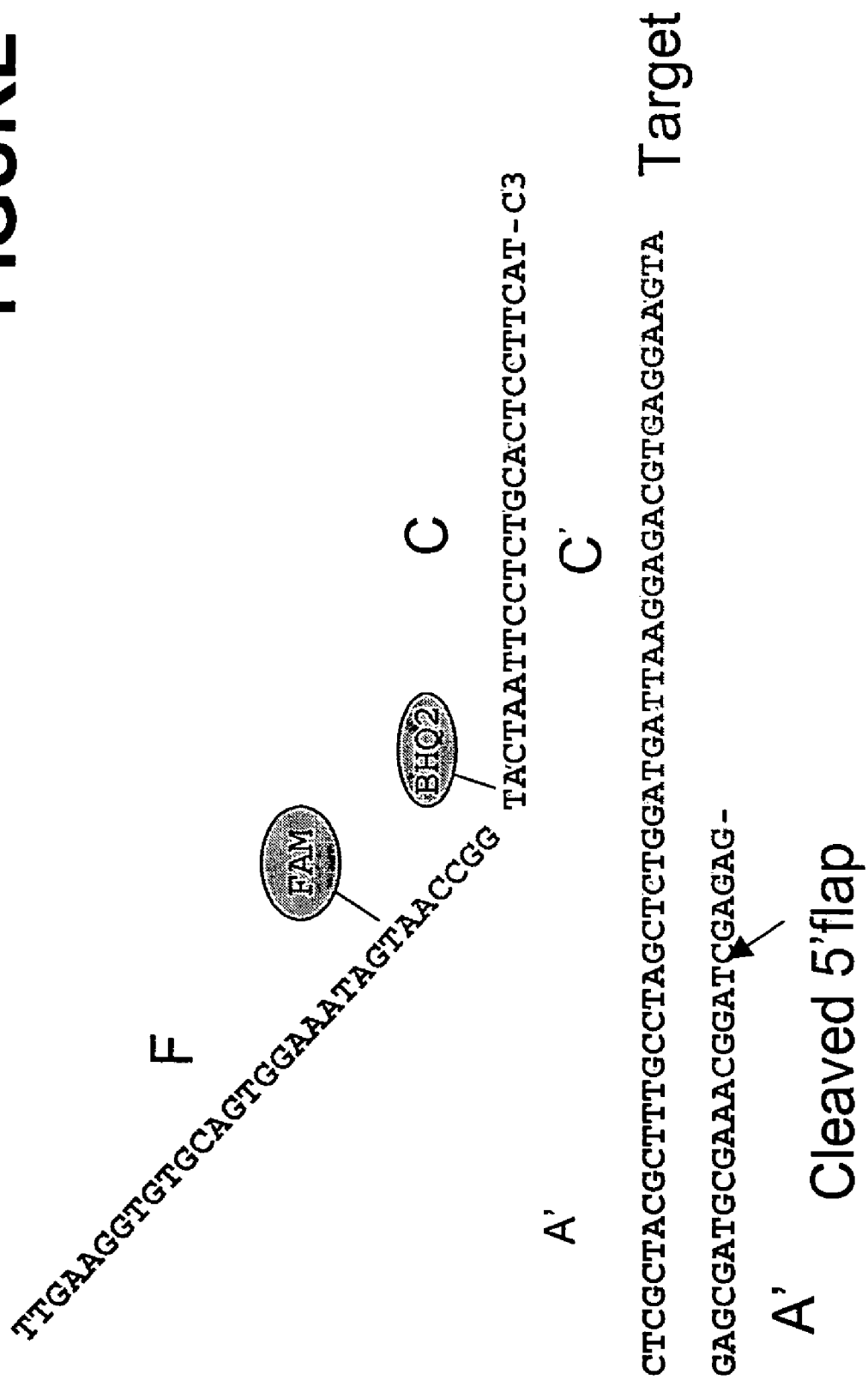
FIG. 11 illustrates another embodiment of the invention in a single cleavage reaction.

Fluorescence data was collected at the end of the 60° C. step of each cycle. The results are graphically represented in FIG. 10. The optimal signal was produced when the complementary portion of the upstream oligonucleotide was separated from the complementary portion of the downstream oligonucleotide by a 2 nucleotide gap and when the upstream oligonucleotide had a single 3' terminal non-complementary nucleotide.

We claim:

1. A method of detecting a target nucleic acid, comprising
(a) providing:
a target nucleic acid, which comprises in 3' to 5' order a first region and a second region,
a template nucleic acid, which comprises in 3' to 5' order a first region and a second region,
a first oligonucleotide that is at least partially complementary to said first region of said target nucleic acid,
a second oligonucleotide comprising a 5' region and a 3' region, wherein said 3' region is complementary to said second region of said target nucleic acid and wherein said 5' region is not complementary to said target nucleic acid but is at least partially complementary to said first region of said template nucleic acid,
a third oligonucleotide comprising a 5' region and a 3' region, wherein said 3' region is at least partially complementary to said second region of said template nucleic acid and said 5' region is not complementary to said template nucleic acid,
a cleavage agent, and
a polymerization agent;
(b) mixing said target nucleic acid, said template nucleic acid, said first oligonucleotide, said second oligonucleotide, said third oligonucleotide, said cleavage agent and said polymerization agent under reaction conditions, wherein said reaction conditions permit:
forming a first duplex between said target nucleic acid and each of said fast oligonucleotide and said second oligonucleotide, wherein the 5' region of the second oligonucleotide forms a first flap of a first non-invasive cleavage structure, wherein the complementary portions of said first oligonucleotide and said second oligonucleotide are separated by at least a nick when the fast duplex is formed,
cleaving the fast flap by said cleavage agent, thereby permitting release of the first flap,
forming a second duplex with the released fast flap, said template nucleic acid, and said third oligonucleotide, wherein the 5' region of the third oligonucleotide forms a second flap of a second non-invasive cleavage structure, wherein the complementary portions of said first flap and said third oligonucleotide are separated by at least a nick when said second duplex is formed, and
cleaving the second flap by said cleavage agent; and
(c) detecting the non-invasive cleavage of the second flap, wherein detection of said non-invasive cleavage of said second flap is indicative of the presence of said target nucleic acid.

2. The method of claim 1, wherein said first oligonucleotide has a single 3' nucleotide that is non-complementary to said target nucleic acid.

3. The method of claim 1, wherein said second and third oligonucleotide are resistant to invasive cleavage.

4. The method of claim 1, wherein said released flap has a single 3' nucleotide that is non-complementary to said template nucleic acid.

5. The method of claim 1, wherein said first oligonucleotide has two or more 3' nucleotides that are non-complementary to said target nucleic acid.

6. The method of claim 1, wherein said first oligonucleotide and/or released flap comprise a 3' block.

7. The method of claim 1, wherein said released flap has two or more 3' nucleotides that are non-complementary to said template nucleic acid.

8. The method of claim 1, wherein said first and said second oligonucleotides are separated by a nick when said fast duplex is formed.

9. The method of claim 1, wherein said first and said second oligonucleotides are separated by a 1 nucleotide gap when said first duplex is formed.

10. The method of claim 1, wherein said first and second oligonucleotides are separated by a 2 nucleotide gap when said first duplex is formed.

11. The method of claim 1, wherein said first and said second oligonucleotides are separated by a 3 nucleotide gap when said first duplex is formed.

12. The method of claim 1, wherein said released flap and said third oligonucleotides are separated by a nick when said second duplex is formed.

13. The method of claim 1, wherein said released flap and said third oligonucleotide are separated by a 1 nucleotide gap when said second duplex is formed.

14. The method of claim 1, wherein said released flap and said third oligonucleotide are separated by a 2 nucleotide gap when said second duplex is formed.

15. The method of claim 1, wherein said released flap and said third oligonucleotide are separated by a 3 nucleotide gap when said second duplex is formed.

16. The method of claim 1, further comprising a forward primer complementary so the first region of said target nucleic acid.

17. The method of claim 16, further comprising a reverse primer complementary to the second region of said target nucleic acid.

18. The method of claim 1, wherein said polymerization agent lacks 5' to 3' exonuclease activity.

19. The method of claim 1, wherein said polymerization agent is thermostable.

20. The method of claim 1, wherein a single enzyme comprises said polymerization agent and said cleavage agent.

21. The method of claim 20, wherein said enzyme is *E. coli* DNA polymerase I, T7 DNA polymerase, Tth DNA polymerase, or Taq DNA polymerase.

22. The method of claim 1, wherein a first enzyme comprises said polymerization agent and a second enzyme comprises said cleavage agent.

23. The method of claim 1, wherein said cleavage agent is a 5' nuclease.

24. The method of claim 1, wherein said cleavage agent is a FEN-1 nuclease.

25. The method of claim 23, wherein said 5' nuclease is thermostable.

26. The method of claim 22, wherein said fast and second enzymes are provided in a single formulation.

27. The method of claim 22, wherein said first enzyme is a Pfu DNA Polymerase and said second enzyme is a FEN-1 nuclease.

28. The method of claim 1, wherein said third oligonucleotide comprises a pair of interactive labels.

29. The method of claim 1, wherein a fast member of a pair of interactive labels is operatively coupled to the 5' flap of said third oligonucleotide.

30. The method of claim 29, wherein the second member of the pair of interactive labels is operatively coupled to position +1 of said third oligonucleotide.

31. The method of claim 29, wherein the second member of the pair of interactive labels is operatively coupled to position +2 of said third oligonucleotide.

32. The method of claim 28, wherein said pair of interactive labels comprises a fluorophore and a quencher.

33. The method of claim 32, wherein said quencher is operatively coupled to position +1 of said third oligonucleotide and said fluorophore is operatively coupled to the 5' flap of said third oligonucleotide.

34. The method of claim 32, wherein said detection of a signal comprises detecting a change in fluorescent between said first and second members of said pair of interactive labels upon cleavage of said third oligonucleotide.

35. A method of detecting a target nucleic acid, comprising
(a) providing:
a target nucleic acid, which comprises in 3' to 5' order a first region and a second region,
a template nucleic acid, which comprises in 3' to 5' order a first region and a second region,
a fast oligonucleotide that is at least partially complementary to said first region of said target nucleic acid,
a second oligonucleotide comprising a 5' region and a 3' region, wherein said 3' region is complementary to said second region of said target nucleic acid and wherein said 5' region is not complementary to said target nucleic acid but is at least partially complementary to said first region of said template nucleic acid,
a third oligonucleotide comprising a 5' region and a 3' region, wherein said 3' region is at least partially complementary to said second region of said template nucleic acid and said 5' region is not complementary to said template nucleic acid,
a cleavage agent, and
a polymerization agent;
(b) forming a reaction mixture by mixing said target nucleic acid, said first oligonucleotide, said second oligonucleotide, said cleavage agent and said polymerization agent under reaction conditions, wherein said reaction conditions permit:
forming of a fast duplex between said target nucleic acid and each of said first oligonucleotide and said second oligonucleotide, wherein the 5' region of the second oligonucleotide forms a first flap of a first non-invasive cleavage structure, and wherein the complementary portions of said fast oligonucleotide and said second oligonucleotide are separated by at least a nick when said fast duplex is formed,
cleavage of the first flap by said cleavage agent, thereby permitting release of the first flap,
(c) mixing the released first flap, said third oligonucleotide, and said template nucleic acid in said reaction mixture under reaction conditions, wherein said reaction conditions permit:
forming of a second duplex with the released first flap, said template nucleic acid, and said third oligonucleotide, wherein the 5' region of the third oligonucleotide forms a second flap of a second non-invasive cleavage structure, wherein the complementary portions of said first flap and said third oligonucleotide are separated by at least a nick when said second duplex is formed, and
cleaving of the second flap by said cleavage agent; and
(d) detecting the non-invasive cleavage of the second flap, wherein detection of said non-invasive cleavage of said second flap is indicative of the presence of said target nucleic acid.

36. A composition comprising:
a target nucleic acid, which comprises in 3' to 5' order a first region and a second region,
(ii) a template nucleic acid, which comprises in 3' to 5' order a first region and a second region,
(iii) a first oligonucleotide that is at least partially complementary to said first region of a said target nucleic acid;
(iv) a second oligonucleotide comprising a 5' flap region and a 3' region, wherein said 3' region is at least partially complementary to said second region of said target nucleic acid and wherein said 5' flap region is non-complementary to said target nucleic acid but is at least partially complementary to said fast region of said template nucleic acid; and
(v) a third oligonucleotide comprising a 5' flap region and a 3' region, wherein said 3' region is at least partially complementary to said second region of said template nucleic acid and said 5' flap region is non-complementary to said template nucleic acid, and wherein a first member of a pair of interactive labels is operatively coupled to said 5' flap region and wherein a second member of the pair of interactive labels is operatively coupled to the said 3' region.

37. A method of detecting a target nucleic acid, comprising
(a) providing:
a target nucleic acid, which comprises in 3' to 5' order a first region and a second region,
a fast oligonucleotide that is at least partially complementary to said fast region of said target nucleic acid,
a second oligonucleotide comprising a 5' region and a 3' region, wherein said 3' region is complementary to said second region of said target nucleic acid and wherein said 5' region is not complementary to said target nucleic acid,
a cleavage agent, and
a polymerization agent;
(b) mixing said target nucleic acid, said first oligonucleotide, said second oligonucleotide, said cleavage agent and said polymerization agent under reaction conditions, wherein said reaction conditions permit:

forming a duplex between said target nucleic acid and each of said first oligonucleotide and said second oligonucleotide, wherein the 5' region of the second oligonucleotide forms a flap of a non-invasive cleavage structure, wherein the complementary portions of said first oligonucleotide and said second oligonucleotide are separated by at least a nick when said duplex is formed, cleaving the flap by said cleavage agent, and (c) detecting the non-invasive cleavage of the flap, wherein detection of said non-invasive cleavage of said flap is indicative of the presence of said target nucleic acid.

* * * * *